United States Patent
Ebel et al.

(10) Patent No.: US 8,877,745 B2
(45) Date of Patent: Nov. 4, 2014

(54) CCR2 RECEPTOR ANTAGONISTS, METHOD FOR PRODUCING THE SAME, AND USE THEREOF AS MEDICAMENTS

(75) Inventors: Heiner Ebel, Biberach an der Riss (DE); Sara Frattini, Catelleone (IT); Riccardo Giovannini, Verona (IT); Christoph Hoenke, Biberach an der Riss (DE); Rocco Mazzaferro, San Giuliano Milanese (IT); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 120 days.

(21) Appl. No.: 13/696,859

(22) PCT Filed: May 10, 2011

(86) PCT No.: PCT/EP2011/057545
§ 371 (c)(1),
(2), (4) Date: Dec. 20, 2012

(87) PCT Pub. No.: WO2011/141474
PCT Pub. Date: Nov. 17, 2011

(65) Prior Publication Data
US 2013/0123241 A1 May 16, 2013

(30) Foreign Application Priority Data
May 12, 2010 (EP) .................... 10162629

(51) Int. Cl.
| C07D 471/04 | (2006.01) |
| A61K 31/506 | (2006.01) |
| C07D 495/04 | (2006.01) |
| C07D 491/10 | (2006.01) |
| C07D 413/14 | (2006.01) |
| C07D 401/14 | (2006.01) |
| C07D 487/04 | (2006.01) |
| C07D 405/14 | (2006.01) |
| C07D 491/107 | (2006.01) |

(52) U.S. Cl.
CPC ............ *C07D 405/14* (2013.01); *C07D 495/04* (2013.01); *C07D 491/10* (2013.01); *C07D 413/14* (2013.01); *C07D 401/14* (2013.01); *C07D 487/04* (2013.01); *C07D 491/107* (2013.01); *C07D 471/04* (2013.01)
USPC ................... 514/211.05; 514/218; 514/235.8; 514/252.14; 514/252.18; 514/256; 540/575; 540/583; 544/122; 544/295; 544/326; 544/327; 544/328; 544/329

(58) Field of Classification Search
USPC .......... 540/575, 583; 544/122, 295, 326, 327, 544/328, 329; 514/211.05, 218, 235.8, 514/252.14, 252.18, 256
See application file for complete search history.

(56) References Cited

U.S. PATENT DOCUMENTS

| 4,032,526 A | 6/1977 | Cross et al. |
| 5,631,269 A | 5/1997 | Broughton et al. |

(Continued)

FOREIGN PATENT DOCUMENTS

| CA | 2687931 A1 | 12/2008 |
| CA | 2704883 A1 | 5/2009 |

(Continued)

OTHER PUBLICATIONS

Barril, Xavier, et al; 4-Amino Derivates of the Hsp90 Inhibitor CCT018159; Bioorganic & Medicinal Chemistry Letters (2006) vol. 16 p. 2543-2548.

(Continued)

*Primary Examiner* — Deepak Rao
(74) *Attorney, Agent, or Firm* — Michael P. Morris; Edward S. Lazer

(57) ABSTRACT

The present invention relates to novel antagonists for CCR2 (CC chemokine receptor 2) of formula (I) wherein HET is a group selected from among formulas (IIa) (IIb) (IIc) (IId) and their use for providing medicaments for treating conditions and diseases, especially pulmonary diseases like asthma and COPD and pain diseases.

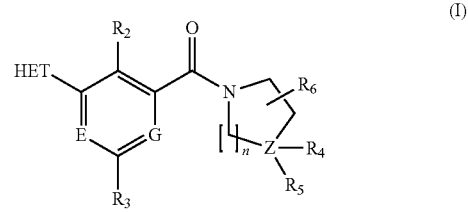

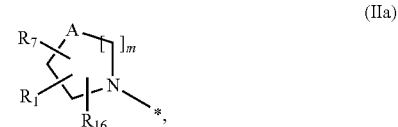

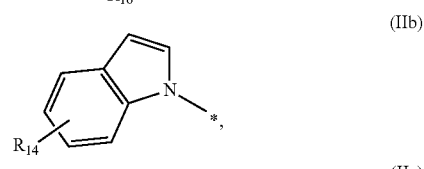

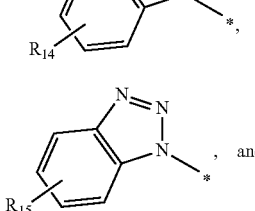

, and

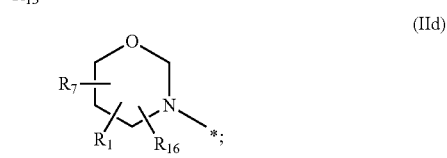

11 Claims, No Drawings

(56) References Cited

U.S. PATENT DOCUMENTS

| | | | |
|---|---|---|---|
| 6,127,386 A | 10/2000 | Lin et al. |
| 6,143,892 A | 11/2000 | Graneto et al. |
| 6,423,713 B1 | 7/2002 | Anantanarayan et al. |
| 6,514,977 B1 | 2/2003 | Anantanarayan et al. |
| 6,806,279 B2 | 10/2004 | Arkin et al. |
| 6,979,686 B1 | 12/2005 | Naraian et al. |
| 7,504,511 B2 | 3/2009 | Carayon et al. |
| 7,507,740 B2 | 3/2009 | Ishikawa et al. |
| 7,612,201 B2 | 11/2009 | Beswick et al. |
| 7,777,041 B2 | 8/2010 | Carayon et al. |
| 7,807,671 B2 | 10/2010 | Wang et al. |
| 7,915,261 B2 | 3/2011 | Ishii et al. |
| 7,919,494 B2 | 4/2011 | Ishii et al. |
| 7,919,495 B2 | 4/2011 | Ishii et al. |
| 8,110,575 B2 | 2/2012 | Gottschling et al. |
| 2004/0014744 A1 | 1/2004 | Haviv et al. |
| 2005/0192302 A1 | 9/2005 | Xue et al. |
| 2005/0222151 A1 | 10/2005 | Carruthers et al. |
| 2006/0004049 A1 | 1/2006 | Yao et al. |
| 2007/0032475 A1 | 2/2007 | Ye et al. |
| 2007/0244132 A1 | 10/2007 | Ishikawa et al. |
| 2008/0161280 A1 | 7/2008 | Gandhi et al. |
| 2008/0306046 A1 | 12/2008 | Ishii et al. |
| 2009/0048238 A1 | 2/2009 | Aebi et al. |
| 2009/0131417 A1 | 5/2009 | Letavic et al. |
| 2009/0318467 A1 | 12/2009 | Adam et al. |
| 2010/0009971 A1 | 1/2010 | Ishii et al. |
| 2010/0009972 A1 | 1/2010 | Ishii et al. |
| 2010/0204209 A1 | 8/2010 | Ebel et al. |
| 2010/0204230 A1 | 8/2010 | Blurton et al. |
| 2011/0021500 A1 | 1/2011 | Gottschling et al. |
| 2011/0183957 A1 | 7/2011 | Wityak et al. |
| 2011/0301143 A1 | 12/2011 | Isabel et al. |
| 2012/0004252 A1 | 1/2012 | Ebel et al. |
| 2012/0053164 A1 | 3/2012 | Ebel et al. |
| 2012/0088754 A1 | 4/2012 | Van Emelen et al. |
| 2012/0108572 A1 | 5/2012 | Wagner et al. |

FOREIGN PATENT DOCUMENTS

| | | | |
|---|---|---|---|
| CA | 2705405 A1 | 5/2009 |
| FR | 2854158 A1 | 10/2004 |
| GB | 2068961 A | 8/1981 |
| JP | 2008239617 A | 10/2008 |
| WO | 8606719 A1 | 11/1986 |
| WO | 9921834 A1 | 5/1999 |
| WO | 0059502 A1 | 10/2000 |
| WO | 0066558 A1 | 11/2000 |
| WO | 0190101 A1 | 11/2001 |
| WO | 03037271 A2 | 5/2003 |
| WO | 03051797 A2 | 6/2003 |
| WO | 03066604 A2 | 8/2003 |
| WO | 03074500 A2 | 9/2003 |
| WO | 03104223 A1 | 12/2003 |
| WO | 2004024710 A1 | 3/2004 |
| WO | 2004074438 A2 | 9/2004 |
| WO | 2004080976 A1 | 9/2004 |
| WO | 2004101546 A1 | 11/2004 |
| WO | 2005009976 A1 | 2/2005 |
| WO | 2005014571 A1 | 2/2005 |
| WO | 2005060665 A2 | 7/2005 |
| WO | 2005084667 A1 | 9/2005 |
| WO | 2005097751 A2 | 10/2005 |
| WO | 2005117909 A2 | 12/2005 |
| WO | 2005118588 A1 | 12/2005 |
| WO | 2006001958 A2 | 1/2006 |
| WO | 2006004741 A2 | 1/2006 |
| WO | 2006012135 A1 | 2/2006 |
| WO | 2006021801 A1 | 3/2006 |
| WO | 2006029906 A1 | 3/2006 |
| WO | 2006034833 A1 | 4/2006 |
| WO | 2006038734 A1 | 4/2006 |
| WO | 2006050389 A2 | 5/2006 |
| WO | 2006072350 A1 | 7/2006 |
| WO | 2006088075 A1 | 8/2006 |
| WO | 2006113704 A2 | 10/2006 |
| WO | 2007003604 A2 | 1/2007 |
| WO | 2007016496 A2 | 2/2007 |
| WO | 2007022937 A1 | 3/2007 |
| WO | 2007026959 A2 | 3/2007 |
| WO | 2007038669 A2 | 4/2007 |
| WO | 2007053495 A2 | 5/2007 |
| WO | 2007053498 A1 | 5/2007 |
| WO | 2007084786 A1 | 7/2007 |
| WO | 2007084868 A2 | 7/2007 |
| WO | 2007092065 A2 | 8/2007 |
| WO | 2007100851 A1 | 9/2007 |
| WO | 2007105058 A2 | 9/2007 |
| WO | 2007120574 A2 | 10/2007 |
| WO | 2007127448 A2 | 11/2007 |
| WO | 2007147874 A1 | 12/2007 |
| WO | 2008083027 A1 | 7/2008 |
| WO | 2008145681 A2 | 12/2008 |
| WO | 2009026204 A1 | 2/2009 |
| WO | 2009043747 A2 | 4/2009 |
| WO | 2009065919 A2 | 5/2009 |
| WO | 2009065920 A2 | 5/2009 |
| WO | 2010017179 A1 | 2/2010 |
| WO | 2010020432 A2 | 2/2010 |
| WO | 2010070032 A1 | 6/2010 |
| WO | 2011073154 A1 | 6/2011 |
| WO | 2011073155 A1 | 6/2011 |
| WO | 2011141474 A1 | 11/2011 |
| WO | 2011141477 A1 | 11/2011 |
| WO | 2011144501 A1 | 11/2011 |
| WO | 2011147772 A1 | 12/2011 |
| WO | 2011151251 A1 | 12/2011 |
| WO | 2012171863 A1 | 12/2012 |
| WO | 2013010839 A1 | 1/2013 |

OTHER PUBLICATIONS

Carter, Percy, H., et al; Advances in the Discovery of CC Chemokine Receptor 2 Antagonists; Annual Reports in Medicinal Chemistry (2007) vol. 42 pp. 211-228.

Chemical Abstracts Service, Columbus, OH, US, STN Database, accession No. 837395-83-2, compounds 837395-83-2 (2005).

Chemical Abstracts Service, Columbus, OH, US, STN Database, accession No. 837396-471 compounds 837396-471 (2005).

Donnelly, Louise, E., et al; Chemokine Receptors as Therapeutic Targets in Chronic Obstructive Pulmonary Disease; Trends in Pharmacological Sciences (2006) vol. 27, No. 10 pp. 546-553.

Hu, Wenhui, et al; Development of a Novel Therapeutic Suppressor of Brain Proinflammatory Cytokine Up-Regulation that Attenuates Synaptic Dysfunction and Behavioral Deficits; Science Direct; Bioorganic & Medicinal Chemistry Letters (2007) vol. 17 pp. 414-418.

International Preliminary Report on Patentability for PCT/EP2009/067378 Issued Jun. 21, 2011.

International Preliminary Report on Patentability for PCT/EP2010/069549 Issued Jun. 19, 2012.

International Search Report for PCT/EP2008/056573 mailed Jan. 14, 2009.

International Search Report for PCT/EP2009/067378 mailed Apr. 16, 2010.

International Search Report for PCT/EP2010/069549 mailed Feb. 23, 2011.

International Search Report for PCT/EP2010/069550 mailed Feb. 23, 2010.

International Search Report for PCT/EP2011/057539 mailed Jul. 20, 2011.

International Search Report for PCT/EP2011/057545 mailed Jul. 4, 2011.

International Search Report for PCT/EP2011/057550 mailed Jun. 28, 2011.

International Search Report for PCT/EP2011/058355 mailed Aug. 9, 2011.

International Search Report for PCT/EP2011/058668 mailed Jun. 28, 2011.

(56) References Cited

OTHER PUBLICATIONS

Kuettel, Sabine, et al; Synthesis and Evaluation of Antiparasitic Activities of New 4-[5-(4-Phenoxyphenyl)-2H-pyrazol-3-yl]morpholine Derivatives; Journal Med. Chem. (2007) vol. 50 pp. 5833-5839.
Lagu, Bharat, et al; Potent and Selective CC-Chemokine Receptor-2 (CCR2) Antagonists as a Potential Treatment for Asthma; Bioorganic and Medicinal Chemistry Letters (2007) vol. 17 pp. 4382-4386.
Rowley, Micheal, et al; 4-Heterocyclylpiperidines as Selective High-Affinity Ligands at the Human Dopamine D4 Receptor; J. Med. Chem (1997) vol. 40 pp. 2374-2385.
U.S. Appl. No. 13/523,220, filed Jun. 14, 2012.
U.S. Appl. No. 13/548,321, filed Jul. 13, 2012.
U.S. Appl. No. 13/696,860, filed Nov. 8, 2012.
Xu, Ping, et al; Synthesis and Anticonvulsant Activity of 3-(substituted piperazino)-6-(substituted phenyl) pyridazines; Chemical Abstracts Service (1991) vol. 23, No. 6, pp. 477-480.
Chabner, Bruce, A., et al; Chemotherapy of Neoplastic Diseases: Antineoplastic Agents: Goodman & Gilman's: The Pharmacological Basis of Therapeutics by Laurence L. Brunton et al (2006) 11th Ed. pp. 1315-1403.
Chemical Abstracts Service, Columbus, OH, US, Yamashita, Hiroshi et al: "Preparation of benzothiophenylpiperazine derivatives for treatment of central nervous system diseases", XP002528684 retrieved from STN. Database accession No. 2008:1217060, Compound RN: 928251-63-2 *abstract* & JP 2008 239617 A (Ohtsuka Pharmaceutical Co., Ltd, Japan) Oct. 9, 2008.
Chemical Abstracts Service, Columbus, OH; US; Ledeboer; Mark W. et al: "Pyrrolopyridines useful as inhibitors of protein kinase and their prepration, pharmaceutical compositions, and use in the treatment of various diseases", XP002528685 retrieved from STN, Database accession No. 2006:1252802 Compounds RN: 916172-93-5, 916172-95-7 *abstract* & WO 2006/127587 A1 (Vertex Pharmaceuticals Incorporated; USA) Nov. 30, 2006.
Cuzzocrea, Salvstore; Shock, Inflammation and PARP; Pharmacological Research (2005) vol. 52 pp. 72-82.
Poupaert, Jacques, H; Drug Design: Basic Principles and Applications; Encyclopedia of Pharmaceutical Technology (2007) 3rd edition pp. 1362-1369.
U.S. Appl. No. 13/698,065, filed Nov. 15, 2012.
U.S. Appl. No. 13/699,325, filed Nov. 21, 2012.
U.S. Appl. No. 13/700,752, filed Nov. 29, 2012.

CCR2 RECEPTOR ANTAGONISTS, METHOD FOR PRODUCING THE SAME, AND USE THEREOF AS MEDICAMENTS

FIELD OF INVENTION

The present invention relates to novel antagonists for CCR2 (CC chemokine receptor 2), the method for producing the same, and their use for providing medicaments for treating conditions and diseases where activation of CCR2 plays a causative role, especially pulmonary diseases like asthma and COPD, neurologic disease, especially of pain diseases, immune related diseases, especially diabetes mellitus including diabetes nephropathy, and cardiovascular diseases, especially atherosclerotic disease.

BACKGROUND OF THE INVENTION

The chemokines are a family of small, proinflammatory cytokines, with potent chemotatctic activities. Chemokines are chemotactic cytokines that are released by a wide variety of cells to attract various cells, such as monocytes, macrophages, T cells, eosinophils, basophils and neutrophils to sites of inflammation.

Chemokine receptors, such as CCR2 or CCR5 have been implicated as being important mediators of inflammatory and immunoregulatory disorders and diseases as well as autoimmune pathologies such as rheumatoid arthritis and atherosclerosis. Accordingly, agents which modulate chemokine receptors such as the CCR2 and CCR5 receptor would be useful in such disorders and diseases.

In particular it is widely accepted that numerous conditions and diseases involve inflammatory processes. Such inflammations are critically triggered and/or promoted by the activity of macrophages, which are formed by differentiation out of monocytes. It has further been found that monocytes are characterized by, e.g., a high expression of membrane-resident CCR2, whereas the CCR2 expression in macrophages is lower. CCR2 is a critical regulator of monocytes trafficking, which can be described as the movement of the monocytes towards an inflammation along a gradient of monocyte chemoattractant proteins (MCP-1, MCP-2, MCP-3, MCP-4).

Therefore, in order to reduce macrophage-induced inflammation, it would be desirable to block the monocyte CCR2 by an antagonist, so that the monocytes can be less triggered to move towards an inflammation area for conversion into macrophages.

Based on the aforesaid there is a need for providing effective antagonists for CCR2, which are pharmacologically acceptable.

DESCRIPTION OF THE INVENTION

It has now been found that such effective CCR2 inhibitors can be provided by compounds according to general formula (I),

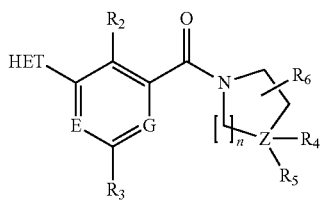

wherein HET is a group selected from among

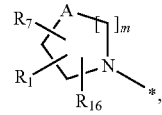

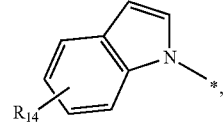

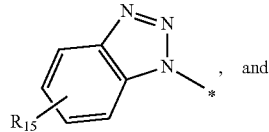

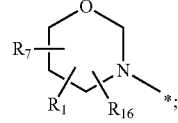

wherein the group of the structure (IIa) denotes saturated or unsaturated or partly unsaturated heterocyclyl, wherein A is a group selected from among C, N, NH, $NR_{12}$, O, and S, wherein m is 0, 1, 2 or 3, wherein $R_{12}$ is a group selected from among $-C_5-C_{10}$-aryl, and $-C_5-C_{10}$-heteroaryl,
wherein the ring $R_{12}$ is optionally substituted with one or more groups selected from among $-CF_3$, $-O-CF_3$, $-CN$, $-C_1-C_6$-alkyl, $-O-C_1-C_4$-alkyl, and -halogen,
or wherein $R_{12}$ is optionally substituted with a bivalent group of the structure $-C_3-C_4$-alkylene group, which is linked on two neighbouring ring atoms of the ring $R_{12}$ such that an annellated ring is formed, in which one or two carbon centers of the -alkylene group may optionally be replaced by 1 or 2 hetero atoms selected from N, O, and S,
wherein such annelated ring is optionally substituted with one or more groups selected from among -halogen, $-CF_3$, $-O-CF_3$, $-CN$, $-C_1-C_3$-alkyl,
or wherein $R_{12}$ is optionally substituted with a bivalent group of the structure $-C_3-C_4$-alkenylene group, which is linked on two neighbouring ring atoms of the ring $R_{12}$ such that an annellated aromatic ring is formed, in which one or two carbon centers of the -alkylene group may optionally be replaced by 1 or 2 hetero atoms selected from N, O, and S,
wherein such ring is optionally substituted with one or more groups selected from among -halogen, $-CF_3$, $-O-CF_3$, $-CN$, $-C_1-C_3$-alkyl;
wherein $R_1$ is a group selected from among $-H$, -halogen, $-CN$, $-O-C_1-C_4$-alkyl, $-C_1-C_4$-alkyl, $-CH=CH_2$, $-C\equiv CH$, $-CF_3$, $-OCF_3$, $-OCF_2H$, $=O$, and $-OCFH_2$,
and wherein $R_7$ is a ring selected from among $-C_5-C_{10}$-aryl, and $-C_5-C_{10}$-heteroaryl, and wherein the ring $R_7$ is optionally substituted with one or more groups selected from among $-CF_3$, $-O-CF_3$, $-CN$, $-C_1-C_6$-alkyl, $-O-C_1-C_6$-alkyl, and -halogen;
or wherein $R_7$ and $R_1$ on two neighbouring ring atoms together form a $-C_3-C_6$-alkenylene group, such that an annellated aromatic ring is formed, in which one or two or three carbon centers may optionally be replaced by 1 or 2 or 3 hetero atoms selected from N, O, and S, wherein the resulting annelated ring being optionally substituted by one or more groups selected from among —OH, —NH$_2$, —C$_1$-C$_3$-alkyl, —O—C$_1$-C$_6$-alkyl, —CN, —CF$_3$, —OCF$_3$, halogen, —C$_6$-aryl, and =O;

or wherein R$_7$ and R$_1$ on two neighbouring ring atoms together form a —C$_1$-C$_6$-alkylene group such that an annellated ring is formed, in which one or two or three carbon centers may optionally be replaced by 1 or 2 or 3 hetero atoms selected from N, O, and S, wherein the resulting annelated ring being optionally substituted by one or more groups selected from —OH, —NH$_2$, —C$_1$-C$_3$-alkyl, —O—C$_1$-C$_6$-alkyl, —CN, —CF$_3$, —OCF$_3$, -halogen, =O, and a group of the structure —C$_5$-C$_{10}$-aryl, wherein such —C$_5$-C$_{10}$-aryl ring is optionally substituted by one or more groups selected from among —OH, —NH$_2$, —C$_1$-C$_3$-alkyl, —O—C$_1$-C$_6$-alkyl, —CN, —CF$_3$, —OCF$_3$, halogen, and =O;

or wherein R$_7$ is a group selected from among spiro-C$_3$-C$_8$-cycloalkyl, spiro-C$_3$-C$_8$-cycloalkenyl, and spiro-C$_3$-C$_8$-heterocyclyl, wherein said spirocyclic ring being optionally substituted with one or more groups selected from among -halogen, —CF$_3$, —O—CF$_3$, —CN, —C$_1$-C$_3$-alkyl, and =O, and wherein said spirocyclic ring being optionally substituted on two neighbouring ring atoms by a —C$_3$-C$_6$-alkenylene group, such that an annellated aromatic ring is formed, wherein the aromatic ring being optionally substituted by one or more groups selected from among —OH, —NH$_2$, —C$_1$-C$_3$-alkyl, —O—C$_1$-C$_6$-alkyl, —CN, —CF$_3$, —OCF$_3$, -halogen, —C$_5$-C$_{10}$-aryl, and =O, and wherein R$_1$ is a group selected from among —H, -halogen, —CN, —O—C$_1$-C$_4$-alkyl, —C$_1$-C$_4$-alkyl, —CH=CH$_2$, —C≡CH, —CF$_3$, —OCF$_3$, —OCF$_2$H, =O, and —OCFH$_2$;

wherein R$_{16}$ is a group selected from among -hydrogen, and =O;

wherein R$_{14}$ is a group selected from among —H, -halogen, —CN, —O—C$_1$-C$_4$-alkyl, —C$_1$-C$_4$-alkyl, —CH=CH$_2$, —C≡CH, —CF$_3$, —OCF$_3$, —OCF$_2$H, and —OCFH$_2$;

wherein R$_{15}$ is a group selected from among —H, -halogen, —CN, —O—C$_1$-C$_4$-alkyl, —C$_1$-C$_4$-alkyl, —CH=CH$_2$, —C≡CH, —CF$_3$, —OCF$_3$, —OCF$_2$H, and —OCFH$_2$;

wherein R$_2$ is selected from among —H, -halogen, —CN, —O—C$_1$-C$_4$-alkyl, —C$_1$-C$_4$-alkyl, -cyclopropyl, —CH=CH$_2$, —C≡CH, —CF$_3$, —OCF$_3$, —OCF$_2$H, and —OCFH$_2$;

wherein R$_3$ is selected from among —H, -methyl, -ethyl, -propyl, -i-propyl, -cyclopropyl, —OCH$_3$, and —CN;

wherein n is 1, 2 or 3;

wherein G and E are N, or wherein G is N and E is C, or wherein G is C and E is N;

wherein Z is C or N;

wherein R$_4$ and R$_5$ are independently selected from among an electron pair, —H, and a group of the structure —C$_1$-C$_6$-alkyl, and wherein R$_4$ and R$_5$ if different from an electron pair or —H are optionally independently substituted with one or more groups selected from among -halogen, —OH, —CF$_3$, and —CN;

or wherein R$_4$ and R$_5$ are independently selected from among an electron pair, —H, and a group of the structure -L$_1$-R$_{13}$, wherein L$_1$ is selected from among —NH— and —N(C$_1$-C$_4$-alkyl)-, wherein R$_{13}$ is —C$_3$-C$_8$-heterocyclyl, wherein R$_{13}$ is optionally substituted by one or more groups selected from among halogen, —CF$_3$, —OCF$_3$, —CN, —OH, —O—C$_1$-C$_4$-alkyl, —C$_1$-C$_6$-alkyl;

or wherein R$_4$ and R$_5$ are independently selected from among an electron pair, —H, —CONH$_2$, and a group selected from among —NR$_8$R$_9$, and —N(R$_{10}$,R$_{10'}$), wherein R$_8$, R$_9$, are independently selected from among —H, —C$_1$-C$_6$-alkyl, and a group of the structure —C$_3$-C$_6$-cycloalkyl, wherein such ring is optionally substituted by one or more groups selected from among —F, and —OCH$_3$, and wherein R$_{10}$ and R$_{10'}$ together form a —C$_2$-C$_6$-alkylene group such that a ring is formed, wherein such ring is optionally substituted with one or more groups selected from among —OH, —OCH$_3$, —CF$_3$, —OCF$_3$, —CN, -halogen, —C$_1$-C$_4$-alkyl, =O, and —N(C$_0$-C$_3$-alkyl)-SO$_2$—C$_1$-C$_3$-alkyl, or wherein R$_{10}$ and R$_{10'}$ together form a —C$_2$-C$_6$-alkylene group such that a ring is formed, wherein such ring is optionally substituted by the group —C$_5$-C$_{10}$-aryl, whereas this group is optionally substituted by a group of the structure —C$_0$-C$_4$-alkylene-COOH;

or wherein R$_4$ and R$_5$ are independently selected from among an electron pair, —H, and a group selected from among —N(R$_{11}$,R$_{11'}$), and wherein R$_{11}$ and R$_{11'}$ together form a —C$_2$-C$_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —OH, —NH$_2$, —C$_1$-C$_3$-alkyl, —O—C$_1$-C$_6$-alkyl, —CN, —CF$_3$, —OCF$_3$, =O, and halogen;

wherein R$_6$ is selected from among —H, —C$_1$-C$_4$-alkyl, —OH, —O—C$_1$-C$_4$-alkyl, -halogen, —CN, —CF$_3$, and —OCF$_3$;

as well as in form of their acid addition salts with pharmacologically acceptable acids, as well as in form of their solvates and/or hydrates.

Preferred compounds of the invention are compounds according to formula (I)

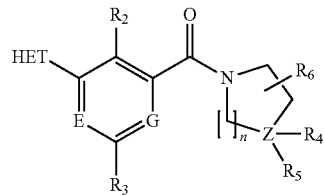

wherein HET is a group selected from among

(IIa)

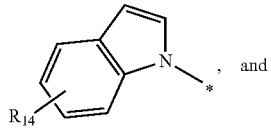
(IIb), and

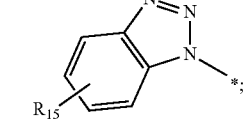
(IIc);

wherein the group of the structure (IIa) denotes saturated or unsaturated or partly unsaturated heterocyclyl, wherein A is a group selected from among C, N, NH, $NR_{12}$, O, and S, wherein m is 0, 1, 2 or 3, wherein $R_{12}$ is a group selected from among —$C_5$-$C_{10}$-aryl, and —$C_5$-$C_{10}$-hetero aryl, wherein the ring $R_{12}$ is optionally substituted with one or more groups selected from among —$CF_3$, —O—$CF_3$, —CN, —$C_1$-$C_6$-alkyl, —O—$C_1$-$C_4$-alkyl, and -halogen, or wherein $R_{12}$ is optionally substituted with a bivalent group of the structure —$C_3$-$C_4$-alkylene group, which is linked on two neighbouring ring atoms of the ring $R_{12}$ such that an annellated ring is formed, in which one or two carbon centers of the -alkylene group may optionally be replaced by 1 or 2 hetero atoms selected from N, O, and S, wherein such annelated ring is optionally substituted with one or more groups selected from among -halogen, —$CF_3$, —O—$CF_3$, —CN, —$C_1$-$C_3$-alkyl, or wherein $R_{12}$ is optionally substituted with a bivalent group of the structure —$C_3$-$C_4$-alkenylene group, which is linked on two neighbouring ring atoms of the ring $R_{12}$ such that an annellated aromatic ring is formed, in which one or two carbon centers of the -alkylene group may optionally be replaced by 1 or 2 hetero atoms selected from N, O, and S, wherein such ring is optionally substituted with one or more groups selected from among -halogen, —$CF_3$, —O—$CF_3$, —CN, —$C_1$-$C_3$-alkyl;

wherein $R_1$ is a group selected from among —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2$H, =O, and —$OCFH_2$, and wherein $R_7$ is a ring selected from among —$C_5$-$C_{10}$-aryl, and —$C_5$-$C_{10}$-heteroaryl, and wherein the ring $R_7$ is optionally substituted with one or more groups selected from among —$CF_3$, —O—$CF_3$, —CN, —$C_1$-$C_6$-alkyl, —O—$C_1$-$C_6$-alkyl, and -halogen;

or wherein $R_7$ and $R_1$ on two neighbouring ring atoms together form a —$C_3$-$C_6$-alkenylene group, such that an annellated aromatic ring is formed, in which one or two or three carbon centers may optionally be replaced by 1 or 2 or 3 hetero atoms selected from N, O, and S, wherein the resulting annelated ring being optionally substituted by one or more groups selected from among —OH, —$NH_2$, —$C_1$-$C_3$-alkyl, —O—$C_1$-$C_6$-alkyl, —CN, —$CF_3$, —$OCF_3$, halogen, —$C_6$-aryl, and =O;

or wherein $R_7$ and $R_1$ on two neighbouring ring atoms together form a —$C_1$-$C_6$-alkylene group such that an annellated ring is formed, in which one or two or three carbon centers may optionally be replaced by 1 or 2 or 3 hetero atoms selected from N, O, and S, wherein the resulting annelated ring being optionally substituted by one or more groups selected from —OH, —$NH_2$, —$C_1$-$C_3$-alkyl, —O—$C_1$-$C_6$-alkyl, —CN, —$CF_3$, —$OCF_3$, -halogen, =O, and a group of the structure —$C_5$-$C_{10}$-aryl, wherein such —$C_5$-$C_{10}$-aryl ring is optionally substituted by one or more groups selected from among —OH, —$NH_2$, —$C_1$-$C_3$-alkyl, —O—$C_1$-$C_6$-alkyl, —CN, —$CF_3$, —$OCF_3$, halogen, and =O;

or wherein $R_7$ is a group selected from among spiro-$C_3$-$C_8$-cycloalkyl, spiro-$C_3$-$C_8$-cycloalkenyl, and spiro-$C_3$-$C_8$-heterocyclyl, wherein said spirocyclic ring being optionally substituted with one or more groups selected from among -halogen, —$CF_3$, —O—$CF_3$, —CN, —$C_1$-$C_3$-alkyl, and =O, and wherein said spirocyclic ring being optionally substituted on two neighbouring ring atoms by a —$C_3$-$C_6$-alkenylene group, such that an annellated aromatic ring is formed, wherein the aromatic ring being optionally substituted by one or more groups selected from among —OH, —$NH_2$, —$C_1$-$C_3$-alkyl, —O—$C_1$-$C_6$-alkyl, —CN, —$CF_3$, —$OCF_3$, -halogen, —$C_5$-$C_{10}$-aryl, and =O, and wherein $R_1$ is a group selected from among —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2$H, =O, and —$OCFH_2$;

wherein $R_{16}$ is a group selected from among -hydrogen, and =O;

wherein $R_{14}$ is a group selected from among —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2$H, and —$OCFH_2$;

wherein $R_{15}$ is a group selected from among —H, -halogen, —CN, —O—$C_1$-$C_4$-alkyl, —$C_1$-$C_4$-alkyl, —CH=$CH_2$, —C≡CH, —$CF_3$, —$OCF_3$, —$OCF_2$H, and —$OCFH_2$;

wherein $R_2$ is selected from among —H, -halogen, —CN, —O—$C_1$-$C_4$-alkyl, —$C_1$-$C_4$-alkyl, -cyclopropyl, —CH=$CH_2$, —C≡CH, —$CF_3$, —$OCF_3$, —$OCF_2$H, and —$OCFH_2$;

wherein $R_3$ is selected from among —H, -methyl, -ethyl, -propyl, -i-propyl, -cyclopropyl, —$OCH_3$, and —CN;

wherein n is 1, 2 or 3;

wherein G and E are N, or wherein G is N and E is C, or wherein G is C and E is N;

wherein Z is C or N;

wherein $R_4$ and $R_5$ are independently selected from among an electron pair, —H, and a group of the structure —$C_1$-$C_6$-alkyl, and wherein $R_4$ and $R_5$ if different from an electron pair or —H are optionally independently substituted with one or more groups selected from among -halogen, —OH, —$CF_3$, and —CN;

or wherein $R_4$ and $R_5$ are independently selected from among an electron pair, —H, and a group of the structure -$L_1$-$R_{13}$, wherein $L_1$ is selected from among —NH— and —N($C_1$-$C_4$-alkyl)-, wherein $R_{13}$ is —$C_3$-$C_8$-heterocyclyl, wherein $R_{13}$ is optionally substituted by one or more groups selected from among halogen, —$CF_3$, —$OCF_3$, —CN, —OH, —O—$C_1$-$C_4$-alkyl, —$C_1$-$C_6$-alkyl;

or wherein $R_4$ and $R_5$ are independently selected from among an electron pair, —H, —$CONH_2$, and a group selected from among —$NR_8R_9$, and —N($R_{10}$,$R_{10'}$), wherein $R_8$, $R_9$, are independently selected from among —H, —$C_1$-$C_6$-alkyl, and a group of the structure —$C_3$-$C_6$-cycloalkyl, wherein such ring is optionally substituted by one or more groups selected from among —F, and —$OCH_3$, and wherein $R_{10}$ and $R_{10'}$, together form a —$C_2$-$C_6$-alkylene group such that a ring is formed, wherein such ring is optionally substituted with one or more groups selected from among —OH, —$OCH_3$, —$CF_3$, —$OCF_3$, —CN, -halogen, —$C_1$-$C_4$-alkyl, =O, and —N($C_0$-$C_3$-alkyl)-$SO_2$—$C_1$-$C_3$-alkyl, or wherein $R_{10}$ and $R_{10'}$ together form a —$C_2$-$C_6$-alkylene group such that a ring is formed, wherein such ring is optionally substituted by the group —$C_5$-$C_{10}$-aryl, whereas this group is optionally substituted by a group of the structure —$C_0$-$C_4$-alkylene-COOH;

or wherein $R_4$ and $R_5$ are independently selected from among an electron pair, —H, and a group selected from among —N($R_{11}$,$R_{11'}$), and wherein $R_{11}$ and $R_{11'}$ together form a —$C_2$-$C_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —OH, —$NH_2$, —$C_1$-$C_3$-alkyl, —O—$C_1$-$C_6$-alkyl, —CN, —$CF_3$, —$OCF_3$, =O, and halogen;

wherein $R_6$ is selected from among —H, —$C_1$-$C_4$-alkyl, —OH, —O—$C_1$-$C_4$-alkyl, -halogen, —CN, —$CF_3$, and —$OCF_3$.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IIa) and $R_{16}$ denotes -hydrogen, and m is 0, 1, 2 or 3, and wherein A is a group selected from among C, $NR_{12}$, and O, and wherein $R_{12}$ is a group selected from among —$C_6$-aryl, and —$C_6$-heteroaryl, wherein the ring $R_{12}$ is optionally substituted by —$CF_3$;

wherein $R_1$ is —H, and wherein $R_7$ is —$C_6$-aryl, and wherein the ring $R_7$ is optionally substituted with one or more groups selected from among —$CF_3$, —$C_1$-$C_6$-alkyl, —O—$C_1$-$C_6$-alkyl, and -halogen;

or wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from among —$C_1$-$C_3$-alkyl, —CN, —$CF_3$, —$OCF_3$, and -halogen, or wherein $R_7$ and $R_1$ on two neighbouring ring atoms together form a —$C_1$-alkylene group such that an annellated ring is formed, wherein the resulting annelated ring being optionally substituted by a group of the structure —$C_5$-$C_{10}$-aryl, or wherein $R_7$ is a group selected from among spiro —$C_5$-cycloalkenyl, and
spiro-$C_5$-heterocyclyl, wherein said spirocyclic ring being optionally substituted on two neighbouring ring atoms by a —$C_4$-alkenylene group, such that an annellated aromatic ring is formed, wherein the aromatic ring being optionally substituted by one or more groups selected from among —OH, —$NH_2$, —$C_1$-$C_3$-alkyl, —O—$C_1$-$C_6$-alkyl, —CN, —$CF_3$, —$OCF_3$, halogen, —$C_5$-$C_{10}$-aryl, and =O, and wherein $R_1$ denotes —H.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IIa) and $R_{16}$ denotes -hydrogen, and m is 0, 1, 2 or 3, and wherein A is a group selected from among C, $NR_{12}$, and O, and wherein $R_{12}$ is a group selected from among —$C_6$-aryl, and —$C_6$-heteroaryl, wherein the ring $R_{12}$ is optionally substituted by —$CF_3$;

wherein $R_1$ is —H, and wherein $R_7$ is —$C_6$-aryl, and wherein the ring $R_7$ is optionally substituted with one or more groups selected from among —$CF_3$, —$C_1$-$C_6$-alkyl, and -halogen;

or wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from among —$C_1$-$C_3$-alkyl, —CN, —$CF_3$, and -halogen, or wherein $R_7$ and $R_1$ on two neighbouring ring atoms together form a —$C_1$-alkylene group such that an annellated ring is formed, wherein the resulting annelated ring being optionally substituted by a group of the structure —$C_5$-$C_{10}$-aryl, or wherein $R_7$ is a group selected from among spiro —$C_5$-cycloalkenyl, and
spiro —$C_5$-heterocyclyl, wherein said spirocyclic ring being optionally substituted on two neighbouring ring atoms by a —$C_4$-alkenylene group, such that an annellated aromatic ring is formed, wherein the aromatic ring being optionally substituted by a group selected from among —OH, —$NH_2$, —$C_1$-$C_3$-alkyl, —O—$C_1$-$C_6$-alkyl, —CN, —$CF_3$, —$OCF_3$, halogen, —$C_5$-$C_{10}$-aryl, and =O, and wherein $R_1$ denotes —H.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, A, m, and n as herein before or below defined, wherein HET is a group according to formula (IIa), wherein $R_1$ is —H, wherein $R_7$ is —$C_6$-aryl, wherein the ring $R_7$ is optionally substituted with one or more groups selected from among —$CF_3$, and —Cl, wherein $R_{16}$ denotes -hydrogen, wherein A is C or $NR_{12}$, and wherein $R_{12}$ is a group of the structure —$C_6$-aryl, wherein the ring $R_{12}$ is optionally substituted by —$CF_3$.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, A, m, and n as herein before or below defined, wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from $C_1$-$C_3$-alkyl, —CN, —$CF_3$, —$OCF_3$, —Cl, —F, and, —Br, and wherein $R_{16}$ denotes -hydrogen, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, m, and n as herein before or below defined, wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$C_1$-$C_3$-alkyl, —$CF_3$, —$OCF_3$, —Cl, —F, and, —Br, and wherein $R_{16}$ denotes -hydrogen, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, m, and n as herein before or below defined, wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$CF_3$, —Cl, and, —Br, and wherein $R_{16}$ denotes -hydrogen, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, m, and n as herein before or below defined, wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$C_1$-$C_3$-alkyl, —$CF_3$, —$OCF_3$, —Cl, —F, and, —Br, and wherein $R_{16}$ denotes -hydrogen, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, m, and n as herein before or wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$CF_3$, —Cl, and, —Br, and wherein $R_{16}$ denotes -hydrogen, and wherein A denotes O.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, and n as herein before or below defined,
wherein HET is a group according to formula (IIb), wherein $R_{14}$ is a group selected from among —H, and —$CF_3$.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, and n as herein before or below defined,
wherein HET is a group according to formula (IIc), wherein $R_{15}$ is a group selected from among —H, and —$CF_3$.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IIa) and wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by a group selected from —$CF_3$, and wherein $R_{16}$ denotes —H, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IIa) and wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by a group selected from -halogen, and wherein $R_{16}$ denotes —H, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IId) and
wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$C_1$-$C_3$-alkyl, —CN, —$CF_3$, —$OCF_3$, —Cl, —F, and, —Br, and wherein $R_{16}$ denotes -hydrogen, and wherein A denotes O.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group according to formula (IId) and wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by a group selected from —$CF_3$, and wherein $R_{16}$ denotes —H, and wherein A denotes O.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{12}$, $R_{13}$, $L_1$, E, G, Z, A, m, and n as herein before or below defined,
wherein HET is a group according to formula (IIa), wherein $R_7$ and $R_1$ on two neighbouring ring atoms together form a —$C_4$-alkenylene group, such that an annellated aromatic ring is formed, in which one carbon center may optionally be replaced by 1 nitrogen atom, wherein the resulting annelated ring being optionally substituted by one or more groups selected from —$C_1$-$C_3$-alkyl, —CN, —$CF_3$, —$OCF_3$, —Cl, —F, and, —Br, and wherein $R_{16}$ denotes -hydrogen, and wherein A denotes C.

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group selected from among

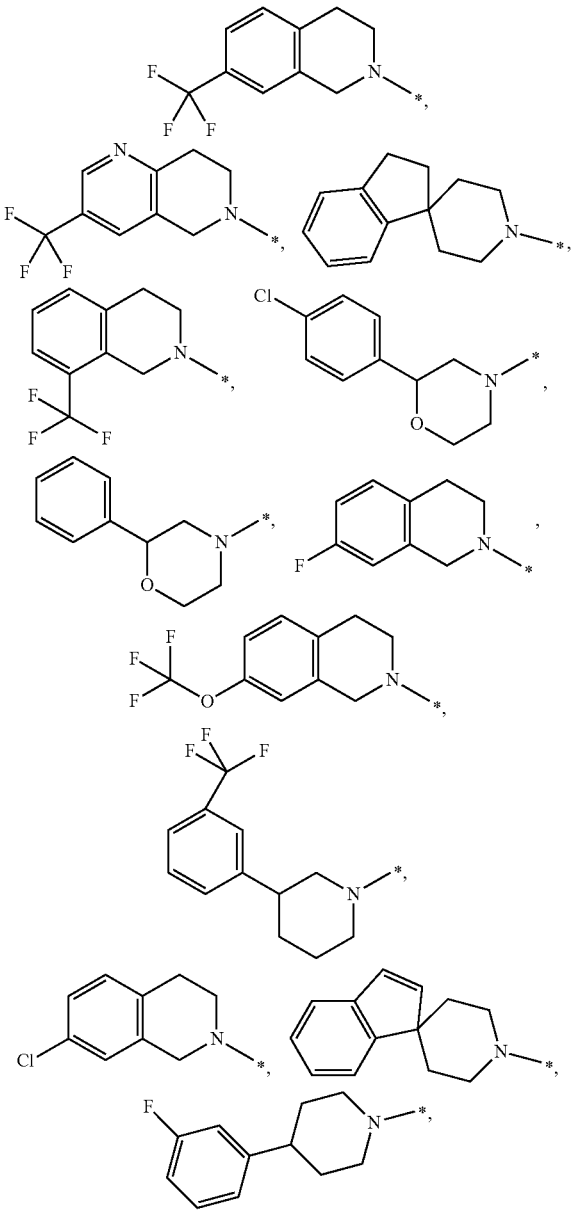

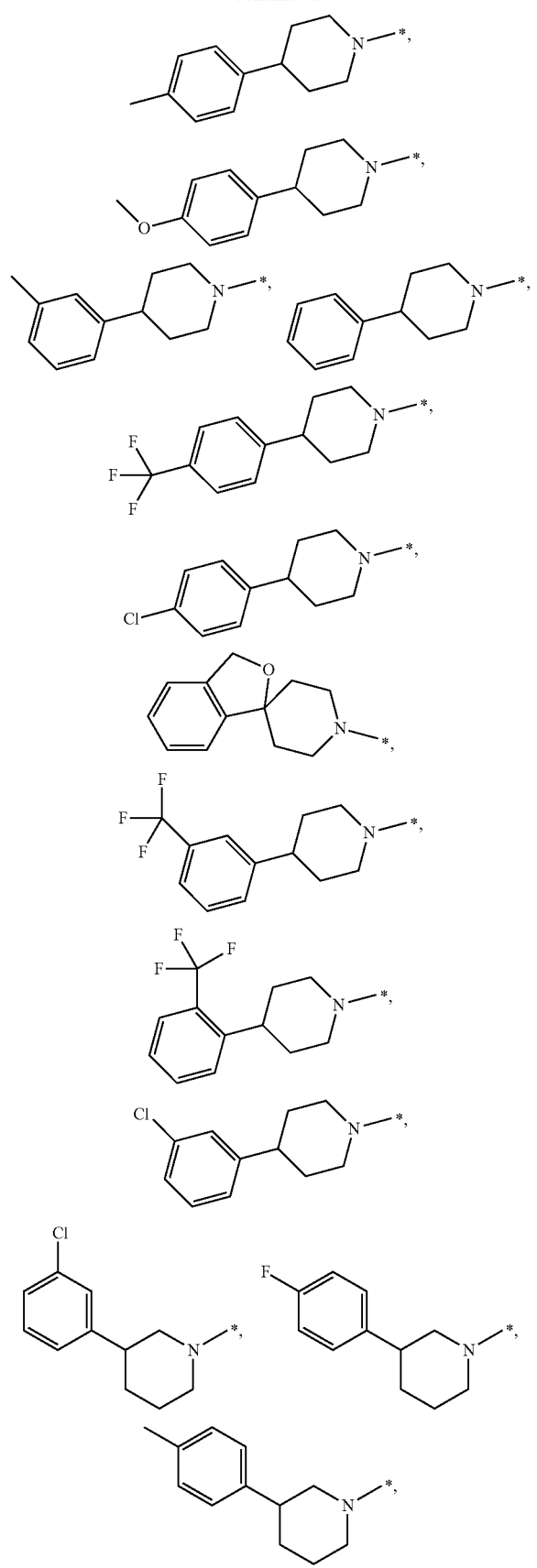
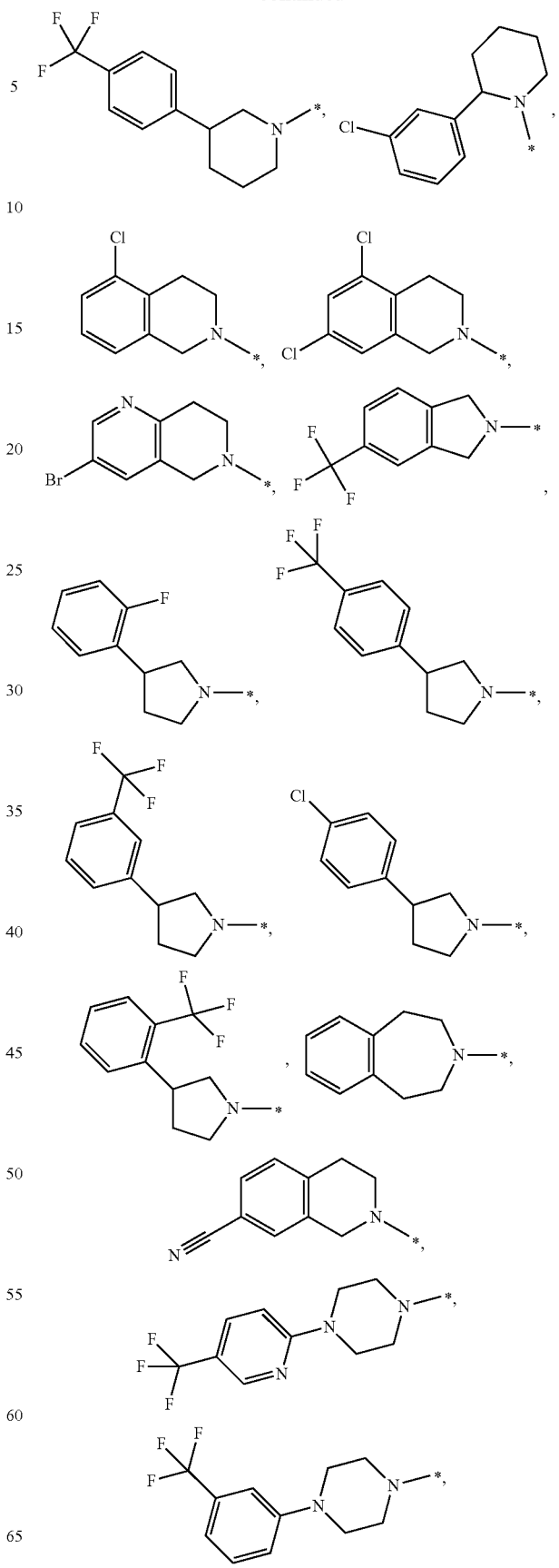

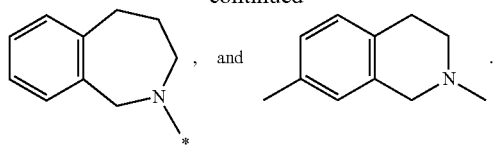, 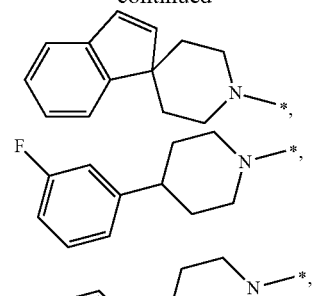
Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group selected from among
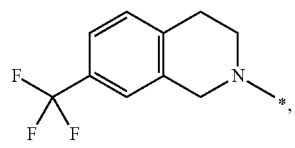
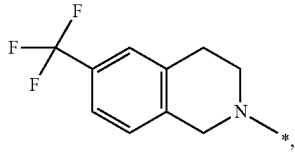
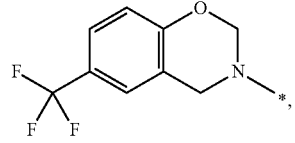
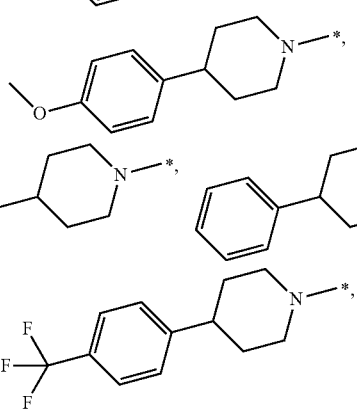
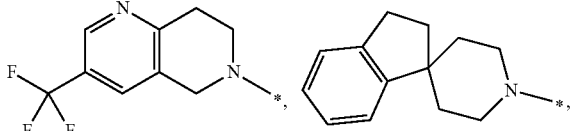
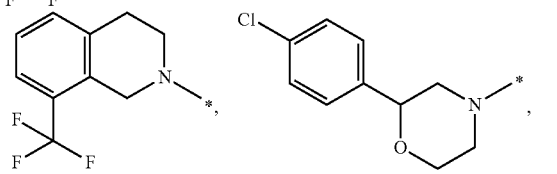
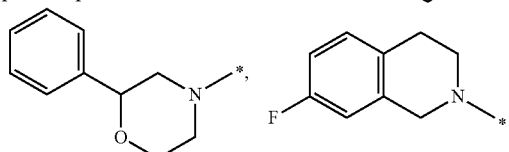
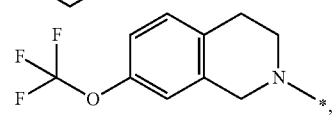
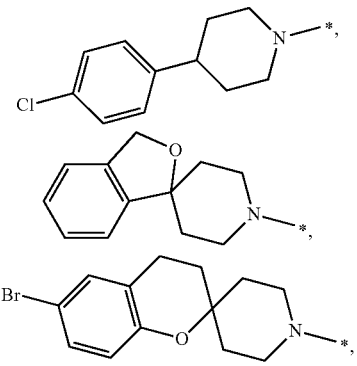
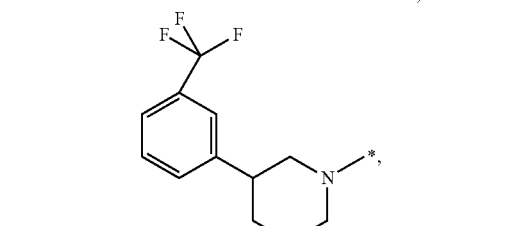
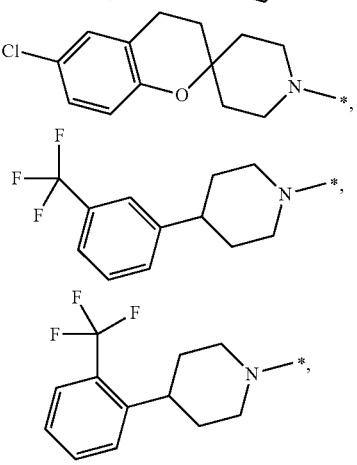
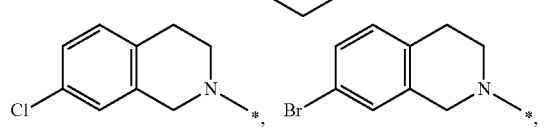

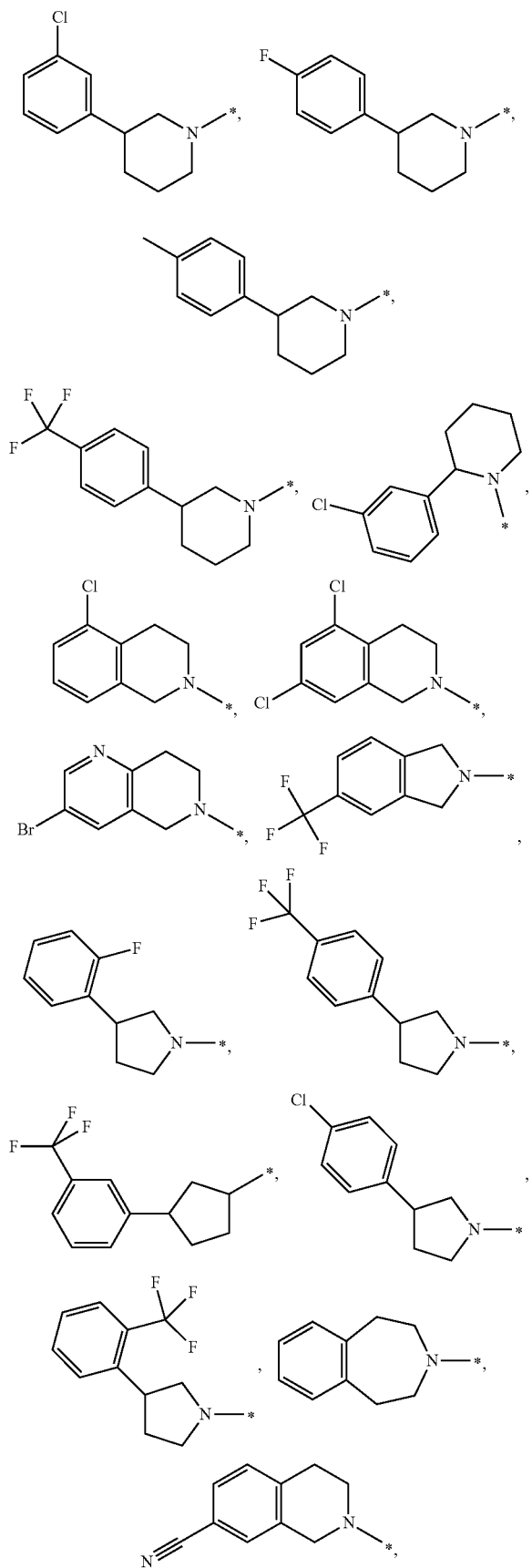

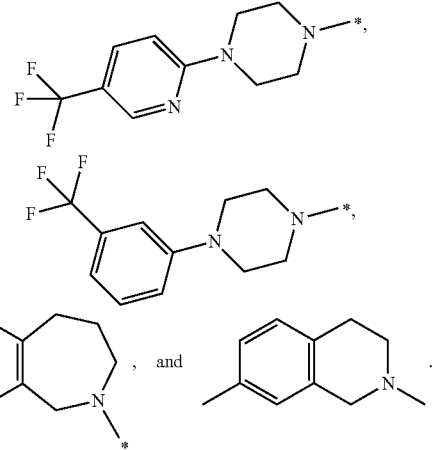

Preferred compounds of formula (I) according to the invention are compounds with $R_2$, $R_3$, $R_4$, $R_5$, $R_6$, $R_8$, $R_9$, $R_{10}$, $R_{10'}$, $R_{11}$, $R_{11'}$, $R_{13}$, $L_1$, E, G, Z, and n as herein before or below defined, wherein HET is a group selected from among

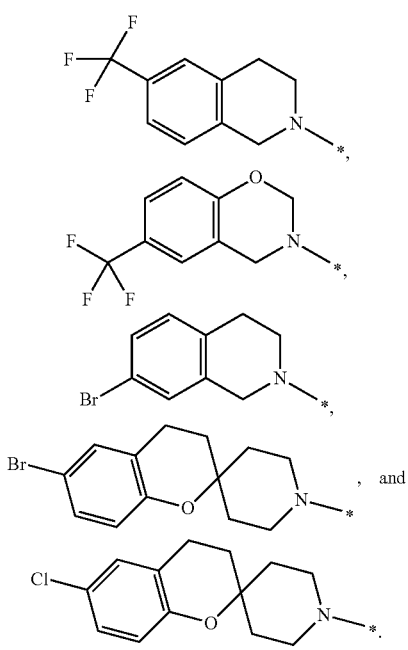

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_2$ is selected from among —H, —$C_1$-$C_4$-alkyl, and —O—$C_1$-$C_4$-alkyl.

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_2$ is selected from among —H, —$CH_3$, -cyclopropyl, and —O—$CH_3$.

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined, wherein $R_2$ denotes —H.

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_2$ denotes —$CH_3$.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, Z, A, m, and n as herein before or below defined,
wherein G and E are N or wherein G is N and E is C.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, Z, A, m, and n as herein before or below defined,
wherein G and E are N.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, Z, A, m, and n as herein before or below defined,
wherein G is N and E is C.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, Z, A, m, and n as herein before or below defined,
wherein G is C and E is N.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, A, m, and n as herein before or below defined,
wherein Z is selected from among C and N.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, A, m, and n as herein before or below defined,
wherein Z denotes C.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_4$ and $R_5$ are independently selected from among an electron pair, —H, and a group of the structure —$C_1$-$C_6$-alkyl,
and wherein $R_4$ and $R_5$ if different from an electron pair or —H are optionally independently substituted with one or more groups selected from among -halogen, —OH, —$CF_3$, and —CN.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_4$ and $R_5$ are independently selected from among an electron pair, —H, and a group of the structure —$C_1$-$C_3$-alkyl, wherein $R_4$ and $R_5$ if different from an electron pair or —H are optionally independently substituted with one or more groups selected from —OH.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, A, m, and n as herein before or below defined,
wherein Z denotes N, wherein $R_4$ denotes an electron pair, and wherein $R_5$ is selected from among, —H, and a group of the structure —$C_1$-$C_6$-alkyl, and wherein $R_5$ if different from —H is optionally substituted with one or more groups selected from among -halogen, —OH, —$CF_3$, and —CN.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, A, m, and n as herein before or below defined,
wherein Z denotes N, wherein $R_4$ denotes an electron pair, and wherein $R_5$ denotes a group of the structure —$C_1$-$C_3$-alkyl, and wherein $R_5$ is optionally independently substituted with one or more groups selected from —OH.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ and $R_5$ are independently selected from among an electron pair, —H, and a group of the structure -$L_1$-$R_{13}$, wherein $L_1$ is selected from among —NH— and —N($C_1$-$C_4$-alkyl)-, wherein $R_{13}$ is —$C_3$-$C_8$-heterocyclyl, wherein $R_{13}$ is optionally substituted by one or more groups selected from among halogen, —$CF_3$, —$OCF_3$, —CN, —OH, —O—$C_1$-$C_4$-alkyl, —$C_1$-$C_6$-alkyl.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ and $R_5$ are independently selected from among an electron pair, —H, and a group of the structure -$L_1$-$R_{13}$, wherein $L_1$ is selected from among —NH— and —N($C_1$-$C_4$-alkyl)-, wherein $R_{13}$ is —$C_3$-$C_8$-heterocyclyl, wherein $R_{13}$ is optionally substituted by one or more groups selected from among halogen, —$CF_3$, —CN, and —$C_1$-$C_6$-alkyl.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ and $R_5$ are independently selected from among —H, and a group of the structure -$L_1$-$R_{13}$, wherein $L_1$ is selected from among —NH—, and —N($C_1$-$C_3$-alkyl)-, wherein $R_{13}$ is —$C_6$-heterocyclyl comprising 1 hetero atom selected from O, wherein $R_{13}$ is optionally substituted by one or more groups selected from among halogen, —$CF_3$, —$OCF_3$, —CN, —OH, and —O—$C_1$-$C_4$-alkyl.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ and $R_5$ are independently selected from among —H, and a group of the structure -$L_1$-$R_{13}$, wherein $L_1$ is selected from among —NH—, and —N($C_1$-$C_3$-alkyl)-, wherein $R_{13}$ is —$C_6$-heterocyclyl comprising 1 hetero atom selected from O, wherein $R_{13}$ is optionally substituted by one or more groups selected from among halogen, —$CF_3$, —CN, and —$C_1$-$C_4$-alkyl.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ denotes —H, and wherein $R_5$ denotes a group of the structure -$L_1$-$R_{13}$, wherein $L_1$ is a group selected from among —NH—, and —N($CH_3$)—, wherein $R_{13}$ is a group of the structure —$C_6$-heterocyclyl comprising 1 hetero atom selected from 0, wherein $R_{13}$ is optionally substituted by —O—$CH_3$.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{11}$, $R_{11'}$, $R_{12}$, $R_{14}$, $R_{15}$, $R_{16}$, E, G, Z, A, m, and n as herein before or below defined,
wherein $R_4$ denotes —H, and wherein $R_5$ denotes a group of the structure -$L_1$-$R_{13}$, wherein $L_1$ is a group selected from among —NH—, and —N(CH$_3$)—, wherein R$_{13}$ is a group of the structure —C$_6$-heterocyclyl comprising 1 hetero atom selected from O.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, Z, A, m, and n as herein before or below defined,
wherein R$_4$ denotes —H, and wherein R$_5$ denotes a group of the structure -L$_1$-R$_{13}$, wherein L$_1$ is a group selected from among —NH—, and —N(CH$_3$)—, wherein R$_{13}$ is a group of the structure —C$_6$-heterocyclyl comprising 1 hetero atom selected from O, wherein R$_{13}$ is optionally substituted by —F.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ is a group of the structure -L$_1$-R$_{13}$, wherein L$_1$ is selected from among —NH— and —N(C$_1$-C$_4$-alkyl)-, wherein R$_{13}$ is —C$_3$-C$_8$-heterocyclyl, wherein R$_{13}$ is optionally substituted by one or more groups selected from among halogen, —CF$_3$, —OCF$_3$, —CN, —OH, —O—C$_1$-C$_4$-alkyl, —C$_1$-C$_6$-alkyl.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ is a group of the structure -L$_1$-R$_{13}$, wherein L$_1$ is selected from among —NH— and —N(C$_1$-C$_4$-alkyl)-, wherein R$_{13}$ is —C$_3$-C$_8$-heterocyclyl, wherein R$_{13}$ is optionally substituted by one or more groups selected from among halogen, —CF$_3$, —CN, and —C$_1$-C$_6$-alkyl.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ is a group of the structure -L$_1$-R$_{13}$, wherein L$_1$ is selected from among —NH—, and —N(C$_1$-C$_3$-alkyl)-, wherein R$_{13}$ is —C$_6$-heterocyclyl comprising 1 hetero atom selected from O, wherein R$_{13}$ is optionally substituted by one or more groups selected from among halogen, —CF$_3$, —OCF$_3$, —CN, —OH, and —O—C$_1$-C$_4$-alkyl.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ is a group of the structure -L$_1$-R$_{13}$, wherein L$_1$ is selected from among —NH—, and —N(C$_1$-C$_3$-alkyl)-, wherein R$_{13}$ is —C$_6$-heterocyclyl comprising 1 hetero atom selected from O, wherein R$_{13}$ is optionally substituted by one or more groups selected from among halogen.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ is a group of the structure -L$_1$-R$_{13}$, wherein L$_1$ is selected from among —NH—, and —N(C$_1$-C$_3$-alkyl)-, wherein R$_{13}$ is —C$_6$-heterocyclyl comprising 1 hetero atom selected from O, wherein R$_{13}$ is optionally substituted by one or more groups selected from among halogen, —CF$_3$, —CN, and —C$_1$-C$_4$-alkyl.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ denotes a group of the structure -L$_1$-R$_{13}$, wherein L$_1$ is a group selected from among —NH—, and —N(CH$_3$)—, wherein R$_{13}$ is a group of the structure —C$_6$-heterocyclyl comprising 1 hetero atom selected from O, wherein R$_{13}$ is optionally substituted by —O—CH$_3$.

Preferred compounds of formula (I) according to the invention are compounds with HET, R$_1$, R$_2$, R$_3$, R$_6$, R$_7$, R$_8$, R$_9$, R$_{10}$, R$_{10'}$, R$_{11}$, R$_{11'}$, R$_{12}$, R$_{14}$, R$_{15}$, R$_{16}$, E, G, A, m, and n as herein before or below defined,
wherein Z denotes C, wherein R$_4$ denotes —H, and wherein R$_5$ denotes a group of the structure -L$_1$-R$_{13}$, wherein L$_1$ is a group selected from among —NH—, and —N(CH$_3$)—, wherein R$_{13}$ is a group of the structure —C$_6$-heterocyclyl comprising 1 hetero atom selected from O, wherein R$_{13}$ is optionally substituted by —F.

Preferred compounds of formula (I) according to the invention are compounds with HET, R$_1$, R$_2$, R$_3$, R$_6$, R$_7$, R$_{11}$, R$_{11'}$, R$_{12}$, R$_{13}$, R$_{14}$, R$_{15}$, R$_{16}$, L$_1$, E, G, Z, A, m, and n as herein before or below defined,
wherein R$_4$ and R$_5$ are independently selected from among an electron pair, —H, —CONH$_2$, and a group selected from among —NR$_8$R$_9$, and —N(R$_{10}$,R$_{10'}$), wherein R$_8$, R$_9$, are independently selected from among —H, —C$_1$-C$_6$-alkyl, and a group of the structure —C$_3$-C$_6$-cycloalkyl, wherein such ring is optionally substituted by one or more groups selected from among —F, and —OCH$_3$, and wherein R$_{10}$ and R$_{10'}$ together form a —C$_2$-C$_6$-alkylene group such that a ring is formed, wherein such ring is optionally substituted with one or more groups selected from among —OH, —OCH$_3$, —CF$_3$, —OCF$_3$, —CN, -halogen, —C$_1$-C$_4$-alkyl, =O, and —N(C$_0$-C$_3$-alkyl)-SO$_2$—C$_1$-C$_3$-alkyl, or wherein R$_{10}$ and R$_{10'}$ together form a —C$_2$-C$_6$-alkylene group such that a ring is formed, wherein such ring is optionally substituted by the group —C$_5$-C$_{10}$-aryl, whereas this group is optionally substituted by a group of the structure —C$_0$-C$_4$-alkylene-COOH.

Preferred compounds of formula (I) according to the invention are compounds with HET, R$_1$, R$_2$, R$_3$, R$_6$, R$_7$, R$_{11}$, R$_{11'}$, R$_{12}$, R$_{13}$, R$_{14}$, R$_{15}$, R$_{16}$, L$_1$, E, G, Z, A, m, and n as herein before or below defined,
wherein R$_4$ and R$_5$ are independently selected from among an electron pair, —H, —CONH$_2$, and a group selected from among —NR$_8$R$_9$, and —N(R$_{10}$,R$_{10'}$), wherein R$_8$, R$_9$, are independently selected from among —H, —C$_1$-C$_6$-alkyl, and a group of the structure —C$_3$-C$_6$-cycloalkyl, wherein such ring is optionally substituted by one or more groups selected from among —F, and —OCH$_3$, and wherein R$_{10}$ and R$_{10'}$ together form a —C$_2$-C$_6$-alkylene group such that a ring is formed, wherein such ring is optionally substituted with one or more groups selected from among —CF$_3$, —CN, -halogen, —C$_1$-C$_4$-alkyl, =O, and —N(C$_0$-C$_3$-alkyl)-SO$_2$—C$_1$-C$_3$-alkyl, or wherein R$_{10}$ and R$_{10'}$ together form a —C$_2$-C$_6$-alkylene group such that a ring is formed, wherein such ring is optionally substituted by the group —C$_5$-C$_{10}$-aryl, whereas this group is optionally substituted by a group of the structure —C$_0$-C$_4$-alkylene-COOH.

Preferred compounds of formula (I) according to the invention are compounds with HET, R$_1$, R$_2$, R$_3$, R$_6$, R$_7$, R$_{11}$, R$_{11'}$, R$_{12}$, R$_{13}$, R$_{14}$, R$_{15}$, R$_{16}$, L$_1$, E, G, Z, A, m, and n as herein before or below defined,
wherein R$_4$ and R$_5$ are independently selected from among —H, —CONH$_2$, and a group selected from among —NR$_8$R$_9$, and —N(R$_{10}$,R$_{10'}$), wherein R$_8$, R$_9$, are independently selected from among —H, and —$C_1$-$C_6$-alkyl, wherein $R_{10}$ and $R_{10'}$ together form a —$C_4$-$C_5$-alkylene group such that a ring is formed, wherein such ring is optionally substituted with one or more groups selected from among —OH, and —N($C_0$-$C_3$-alkyl)-$SO_2$—$C_1$-$C_3$-alkyl, or wherein $R_{10}$ and $R_{10'}$ together form a —$C_4$-$C_5$-alkylene group such that a ring is formed, wherein such ring is optionally substituted by the group —$C_6$-aryl, whereas this group is optionally substituted by —COOH.

Preferred compounds of formula (I) according to the invention are compounds with HET, $R_1$, $R_2$, $R_3$, $R_6$, $R_7$, $R_8$, $R_9$, $R_{11}$, $R_{11'}$, $R_{12}$, $R_{13}$, $R_{14}$, $R_{15}$, $R_{16}$, $L_1$, E, G, Z, A, m, and n as hereinbefore or below defined,
wherein $R_4$ denotes —H, and wherein $R_5$ denotes a group of the structure —N($R_{10}$,$R_{10'}$), wherein $R_{10}$ and $R_{10'}$ together form a —$C_4$-$C_5$-alkylene group such that a ring is formed, wherein such ring is optionally substituted with one or more groups selected from among —OH, and —N($C_0$-$C_1$-alkyl)-$SO_2$—$CH_3$.

Preferred compounds of formula (I) according to the invention are compounds with HET, $R_1$, $R_2$, $R_3$, $R_6$, $R_7$, $R_{11}$, $R_{11'}$, $R_{12}$, $R_{13}$, $R_{14}$, $R_{15}$, $R_{16}$, $L_1$, E, G, A, m, and n as hereinbefore or below defined,
wherein Z denotes C, wherein $R_4$ is a group selected from among —H, and —$CONH_2$, wherein $R_5$ is selected from among —$NR_8R_9$, and —N($R_{10}$,$R_{10'}$), wherein $R_8$, $R_9$, are independently selected from among —H, —$C_1$-$C_6$-alkyl, and a group of the structure —$C_3$-$C_6$-cycloalkyl, wherein such ring is optionally substituted by one or more groups selected from among —F, and —$OCH_3$, and wherein $R_{10}$ and $R_{10'}$ together form a —$C_2$-$C_6$-alkylene group such that a ring is formed, wherein such ring is optionally substituted with one or more groups selected from among —OH, —$OCH_3$, —$CF_3$, —$OCF_3$, —CN, -halogen, —$C_1$-$C_4$-alkyl, =O, and —N($C_0$-$C_3$-alkyl)-$SO_2$—$C_1$-$C_3$-alkyl, or wherein $R_{10}$ and $R_{10'}$ together form a —$C_2$-$C_6$-alkylene group such that a ring is formed, wherein such ring is optionally substituted by the group —$C_5$-$C_{10}$-aryl, whereas this group is optionally substituted by a group of the structure —$C_0$-$C_4$-alkylene-COOH.

Preferred compounds of formula (I) according to the invention are compounds with HET, $R_1$, $R_2$, $R_3$, $R_6$, $R_7$, $R_{11}$, $R_{11'}$, $R_{12}$, $R_{13}$, $R_{14}$, $R_{15}$, $R_{16}$, $L_1$, E, G, A, m, and n as hereinbefore or below defined,
wherein Z denotes C, wherein $R_4$ is a group selected from among —H, and —$CONH_2$, wherein $R_5$ is selected from among —$NR_8R_9$, and —N($R_{10}$,$R_{10'}$), wherein $R_8$, $R_9$, are independently selected from among —H, —$C_1$-$C_6$-alkyl, and a group of the structure —$C_3$-$C_6$-cycloalkyl, wherein such ring is optionally substituted by one or more groups selected from among —F, and —$OCH_3$, and wherein $R_{10}$ and $R_{10'}$ together form a —$C_2$-$C_6$-alkylene group such that a ring is formed, wherein such ring is optionally substituted with one or more groups selected from among —$CF_3$, —CN, -halogen, —$C_1$-$C_4$-alkyl, =O, and —N($C_0$-$C_3$-alkyl)-$SO_2$—$C_1$-$C_3$-alkyl, or wherein $R_{10}$ and $R_{10'}$ together form a —$C_2$-$C_6$-alkylene group such that a ring is formed, wherein such ring is optionally substituted by the group —$C_5$-$C_{10}$-aryl, whereas this group is optionally substituted by a group of the structure —$C_0$-$C_4$-alkylene-COOH.

Preferred compounds of formula (I) according to the invention are compounds with HET, $R_1$, $R_2$, $R_3$, $R_6$, $R_7$, $R_{11}$, $R_{11'}$, $R_{12}$, $R_{13}$, $R_{14}$, $R_{15}$, $R_{16}$, $L_1$, E, G, A, m, and n as hereinbefore or below defined,
wherein Z denotes C, wherein $R_4$ is a group selected from among —H, and —$CONH_2$, wherein $R_5$ is selected from among —$NR_8R_9$, and —N($R_{10}$,$R_{10'}$), wherein $R_8$, $R_9$, are independently selected from among —H, and —$C_1$-$C_6$-alkyl, and wherein $R_{10}$ and $R_{10'}$ together form a —$C_4$-$C_5$-alkylene group such that a ring is formed, wherein such ring is optionally substituted with one or more groups selected from among —OH, and —N($C_0$-$C_3$-alkyl)-$SO_2$—$C_1$-$C_3$-alkyl, or wherein $R_{10}$ and $R_{10'}$ together form a —$C_4$-$C_5$-alkylene group such that a ring is formed, wherein such ring is optionally substituted by the group —$C_6$-aryl, whereas this group is optionally substituted by —COOH.

Preferred compounds of formula (I) according to the invention are compounds with HET, $R_1$, $R_2$, $R_3$, $R_6$, $R_7$, $R_8$, $R_9$, $R_{11}$, $R_{11'}$, $R_{12}$, $R_{13}$, $R_{14}$, $R_{15}$, $R_{16}$, $L_1$, E, G, A, m, and n as hereinbefore or below defined,
wherein Z denotes C, wherein $R_4$ denotes —H, and wherein $R_5$ denotes a group of the structure —N($R_{10}$,$R_{10'}$), wherein $R_{10}$ and $R_{10'}$, together form a —$C_4$-$C_5$-alkylene group such that a ring is formed, wherein such ring is optionally substituted with one or more groups selected from among —OH, and —N($C_0$-$C_1$-alkyl)-$SO_2$—$CH_3$.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, Z, A, m, and n as hereinbefore or below defined,
wherein $R_4$ and $R_5$ are independently selected from among an electron pair, —H, and a group selected from among —N($R_{11}$,$R_{11'}$), wherein $R_{11}$ and $R_{11'}$ together form a —$C_2$-$C_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —OH, —$NH_2$, —$C_1$-$C_3$-alkyl, —O—$C_1$-$C_6$-alkyl, —CN, —$CF_3$, —$OCF_3$, =O, and halogen.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, Z, A, m, and n as hereinbefore or below defined,
wherein $R_4$ and $R_5$ are independently selected from among an electron pair, —H, and a group selected from among —N($R_{11}$,$R_{11'}$), wherein $R_{11}$ and $R_{11'}$ together form a —$C_2$-$C_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —$C_1$-$C_3$-alkyl, —CN, —$CF_3$, =O, and halogen.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, Z, A, m, and n as hereinbefore or below defined,
wherein $R_4$ and $R_5$ are independently selected from among —H, and a group of the structure —N($R_{11}$,$R_{11'}$), wherein $R_{11}$ and $R_{11'}$ together form a —$C_4$-$C_5$-alkylene group such that a ring is formed, in which one ore two carbon centers may optionally be replaced by one or two hetero atoms selected from among N, and O, wherein such ring is optionally substituted by —$C_1$-$C_3$-alkyl on one ring atom.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, Z, A, m, and n as hereinbefore or below defined,
wherein $R_4$ denotes —H, and wherein $R_5$ denotes a group of the structure —N($R_{11}$,$R_{11'}$), wherein $R_{11}$ and $R_{11'}$ together form a —$C_5$-alkylene group such that a ring is formed, in which one carbon center is replaced by one hetero atom selected from O.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, A, m, and n as herein before or below defined,
wherein Z denotes C, wherein $R_4$ denotes —H, wherein $R_5$ denotes —N($R_{11}$,$R_{11'}$), wherein $R_{11}$ and $R_{11'}$ together form a —$C_2$-$C_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —OH, —$NH_2$, —$C_1$-$C_3$-alkyl, —O—$C_1$-$C_6$-alkyl, —CN, —$CF_3$, —$OCF_3$, =O, and halogen.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, A, m, and n as herein before or below defined,
wherein Z denotes C, wherein $R_4$ denotes —H, wherein $R_5$ denotes —N($R_{11}$,$R_{11'}$), wherein $R_{11}$ and $R_{11'}$ together form a —$C_2$-$C_6$-alkylene group such that a ring is formed, in which one ore two carbon centers may optionally be replaced by one or two hetero atoms selected from among N, O, and S, wherein such ring is optionally be substituted by one or more groups on one ring atom or on two neighbouring ring atoms selected from among —$C_1$-$C_3$-alkyl, —CN, —$CF_3$, =O, and halogen.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, A, m, and n as herein before or below defined,
wherein Z denotes C, wherein $R_4$ denotes —H, wherein $R_5$ denotes —N($R_{11}$,$R_{11'}$), wherein $R_{11}$ and $R_{11'}$ together form a —$C_4$-$C_5$-alkylene group such that a ring is formed, in which one ore two carbon centers may optionally be replaced by one or two hetero atoms selected from among N, and O, wherein such ring is optionally substituted by —$C_1$-$C_3$-alkyl on one ring atom.

Preferred compounds of formula (I) according to the invention are compounds with HET, $R_1$, $R_2$, $R_3$, $R_6$, $R_7$, $R_8$, $R_9$, $R_{10}$, $R_{10'}$, $R_{12}$, $R_{13}$, $R_{14}$, $R_{15}$, $R_{16}$, $L_1$, E, G, A, m, and n as herein before or below defined,
wherein Z denotes C, wherein $R_4$ denotes —H, wherein $R_5$ denotes a group of the structure —N($R_{11}$,$R_{11'}$), wherein $R_{11}$ and $R_{11'}$ together form a —$C_5$-alkylene group such that a ring is formed, in which one carbon center is replaced by one hetero atom selected from O.

Preferred compounds of formula (I) according to the invention are compounds with HET, $R_1$, $R_2$, $R_3$, $R_6$, $R_7$, $R_8$, $R_9$, $R_{12}$, $R_{13}$, $R_{14}$, $R_{15}$, $R_{16}$, $L_1$, E, G, A, m, and n as herein before or below defined,
wherein Z denotes C, wherein $R_4$ denotes —H, and wherein $R_5$ denotes a group of the structure -$L_1$-$R_{13}$, wherein $L_1$ is a group selected from among —NH—, and —N($CH_3$)—, wherein $R_{13}$ is a group of the structure

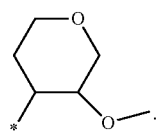 [SMILES: *C1CCOCC1OC]

Preferred compounds of formula (I) according to the invention are compounds with HET, $R_1$, $R_2$, $R_3$, $R_6$, $R_7$, $R_8$, $R_9$, $R_{12}$, $R_{13}$, $R_{14}$, $R_{15}$, $R_{16}$, $L_1$, E, G, A, m, and n as herein before or below defined,
wherein Z denotes C, wherein $R_4$ is a group selected from among —H, and —CO—$NH_2$, and wherein $R_5$ is a group selected from among

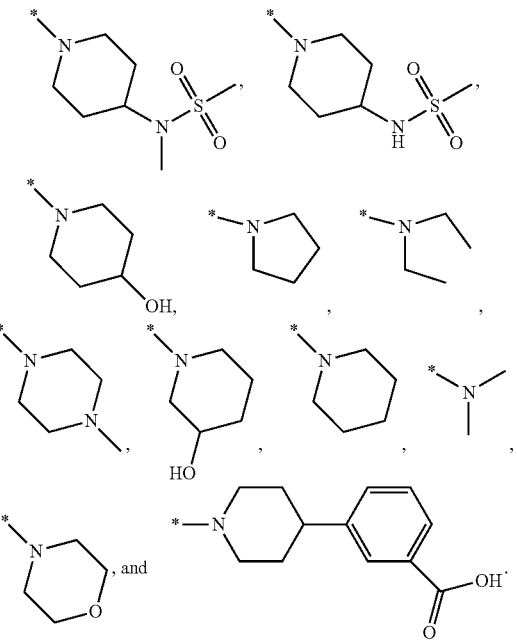

Preferred compounds of formula (I) according to the invention are compounds with HET, $R_1$, $R_2$, $R_3$, $R_6$, $R_7$, $R_8$, $R_9$, $R_{12}$, $R_{13}$, $R_{14}$, $R_{15}$, $R_{16}$, $L_1$, E, G, A, m, and n as herein before or below defined,
wherein Z denotes N, wherein $R_4$ denotes an electron pair, and wherein $R_5$ is a group selected from among

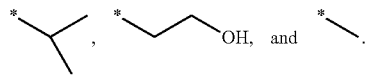

Preferred compounds of formula (I) according to the invention are compounds with HET, $R_1$, $R_2$, $R_3$, $R_4$, $R_5$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_6$ is —H.

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_2$ is selected from among —$CH_3$, -cyclopropyl, and —$OCH_3$.

Preferred compounds of formula (I) according to the invention are compounds with HET, $R_1$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_2$ is selected from among —$CH_3$, and —$OCH_3$.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_3$ denotes -hydrogen.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_3$ denotes -cyclopropyl.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n as herein before or below defined,
wherein $R_3$ denotes —$OCH_3$.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, A, m, and n as herein before or below defined,
wherein Z denotes C.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, and n as herein before or below defined,
wherein m is 1 or 2.

Preferred compounds of formula (I) according to the invention are compounds with HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, and, m as herein before or below defined,
wherein n is 2.

All of the above embodiments under formula (I) have to be understood to optionally be present in form of their individual optical isomers, mixtures of their individual optical isomers, or racemates, as well as in form of their acid addition salts with pharmacologically acceptable acids, as well as in form of their solvates and/or hydrates.

It has now been found that such compounds as herein before or below defined could be used as a medicament.

It has been found that such compounds as herein before or below defined could be used for making a medicament for the treatment of inflammatory diseases. It has been found that such compounds as herein before or below defined could be used for making a medicament for the treatment of inflammatory diseases, wherein the inflammatory diseases are selected from inflammatory diseases of the respiratory tract. It has been found that such compounds as herein before or below defined could be used for making a medicament for the treatment of inflammatory diseases, wherein the inflammatory diseases are selected from chronic obstructive pulmonary disease, asthma, and cystic fibrosis. It has been found that such compounds as herein before or below defined could be used for making a medicament for the treatment of neurologic diseases, preferably for the treatment of pain diseases especially for the treatment of inflammatory and neuropathic pain disease, especially for the treatment of chronic pain. It has been found that such compounds as herein before or below defined could be used for making a medicament for the treatment of immune related diseases, preferably for the treatment of diabetes mellitus. It has been found that such compounds as herein before or below defined could be used for making a medicament for the treatment of cardiovascular diseases, preferably for the treatment of peripheral atherosclerotic disease. It has been found that such compounds as herein before or below defined could be used for making a medicament for the treatment of diabetic nephropathy.

Present invention encloses compounds as herein before or below defined as medicaments. Present invention encloses compounds as herein before or below defined as medicaments for the treatment of inflammatory diseases. Present invention encloses compounds as herein before or below defined as medicaments for the treatment of inflammatory diseases, wherein the inflammatory diseases are selected from inflammatory diseases of the respiratory tract. Present invention encloses compounds as herein before or below defined as medicaments for the treatment of inflammatory diseases, wherein the inflammatory diseases are selected from chronic obstructive pulmonary disease, asthma, and cystic fibrosis. Present invention encloses compounds as herein before or below defined as medicaments for the treatment of neurologic diseases, preferably for the treatment of pain diseases especially for the treatment of inflammatory and neuropathic pain disease, especially for the treatment of chronic pain. Present invention encloses compounds as herein before or below defined as medicaments for the treatment of immune related diseases, preferably for the treatment of diabetes mellitus. Present invention encloses compounds as herein before or below defined as medicaments for the treatment of cardiovascular diseases, preferably for the treatment of peripheral atherosclerotic disease. Present invention encloses compounds as herein before or below defined as medicaments for the treatment of diabetic nephropathy.

It has been found that such compounds as herein before or below defined could be used for the treatment of inflammatory diseases. It has been found that such compounds as herein before or below defined could be used for the treatment of inflammatory diseases, wherein the inflammatory diseases are selected from inflammatory diseases of the respiratory tract. It has been found that such compounds as herein before or below defined could be used for the treatment of inflammatory diseases, wherein the inflammatory diseases are selected from chronic obstructive pulmonary disease, asthma, and cystic fibrosis. It has been found that such compounds as herein before or below defined could be used for the treatment of neurologic diseases, preferably for the treatment of pain diseases especially for the treatment of inflammatory and neuropathic pain disease, especially for the treatment of chronic pain. It has been found that such compounds as herein before or below defined could be used for the treatment of immune related diseases, preferably for the treatment of diabetes mellitus. It has been found that such compounds as herein before or below defined could be used for the treatment of cardiovascular diseases, preferably for the treatment of peripheral atherosclerotic disease. It has been found that such compounds as herein before or below defined could be used for the treatment of diabetic nephropathy.

DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_1$-$C_6$-alkyl means an alkyl group or radical having 1 to 6 carbon atoms. In general, for groups comprising two or more subgroups, the last named subgroup is the radical attachment point, for example, the substituent "aryl-$C_1$-$C_3$-alkyl-" means an aryl group which is bound to a $C_1$-$C_3$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

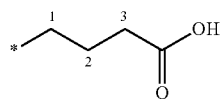

wherein the carboxy group is attached to the third carbon atom of the propyl group. The terms "1-methylpropyl-", "2,2-dimethylpropyl-" or "cyclopropylmethyl-" group represent the following groups:

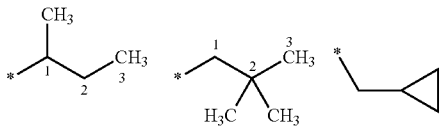

The asterisk may be used in sub-formulas to indicate the bond which is connected to the core molecule as defined.

Many of the followings terms may be used repeatedly in the definition of a formula or group and in each case have one of the meanings given above, independently of one another.

Unless otherwise stated, all the substituents are independent of one another. If for example there might be a plurality of $C_1$-$C_6$-alkyl groups as substituents in one group, in the case of three substituents $C_1$-$C_6$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (Piperidin-A), 4-piperidinyl (Piperidin-B), 2-tolyl (Tolyl-C), 3-tolyl (Tolyl-D), and 4-tolyl (Tolyl-E) are shown as follows:

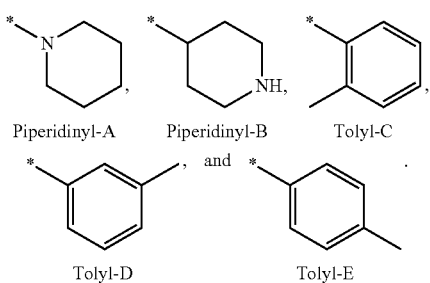

If there is no asterisk (*) in the structural formula of the substituent, each hydrogen atom may be removed from the substituent and the valency thus freed may act as a binding site to the rest of a molecule. Thus, for example, (Tolyl-F) may represent 2-tolyl, 3-tolyl, 4-tolyl, and benzyl

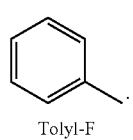

Tolyl-F

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

By the term "branched or unbranched, saturated or unsaturated $C_1$-$C_6$-carbon chain" it is meant a chain of carbon atoms, which is constituted by 1 to 6 carbon atoms arranged in a row and which can optionally further comprise branches or one or more hetero atoms selected from N, O or S. Said carbon chain can be saturated or unsaturated by comprising double or triple bonds.

If the carbon chain is to be substituted by a group which together with one or two carbon atoms of an alkylene chain forms a carbocyclic ring with 3, 5 or 6 carbon atoms, this includes the following examples of the rings:

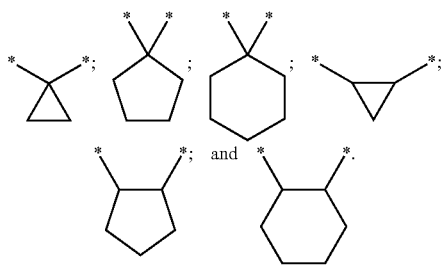

The term "$C_1$-$C_n$-alkyl", wherein n is an integer from 2 to n, either alone or in combination with another radical denotes an acyclic, saturated, branched or linear hydrocarbon radical with 1 to n C atoms. For example the term $C_1$-$C_5$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

By the term "$C_1$-$C_6$-alkyl" (including those which are part of other groups) are meant branched and unbranched alkyl groups with 1 to 6 carbon atoms and by the term "$C_1$-$C_4$-alkyl" are meant branched and unbranched alkyl groups with 1 to 4 carbon atoms. Alkyl groups with 1 to 4 carbon atoms are preferred. By the term "$C_1$-$C_3$-alkyl" are meant branched and unbranched alkyl groups with 1 to 3 carbon atoms and by the term "$C_2$-$C_4$-alkyl" are meant branched and unbranched alkyl groups with 2 to 4 carbon atoms. Examples for alkyl groups with 1-6 carbon atoms include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

The term "$C_1$-$C_n$-alkylene" wherein n is an integer 2 to n, either alone or in combination with another radical, denotes an acyclic, straight or branched chain divalent alkyl radical containing from 1 to n carbon atoms. For example the term $C_1$-$C_4$-alkylene includes —$CH_2$—, —$CH_2$—$CH_2$—, —CH($CH_3$)—, —$CH_2$—$CH_2$—$CH_2$—, —C($CH_3$)$_2$—, —CH($CH_2CH_3$)—, —CH($CH_3$)—$CH_2$—, —$CH_2$—CH($CH_3$)—, —$CH_2$—$CH_2$—$CH_2$—$CH_2$—, —$CH_2$—$CH_2$—CH($CH_3$)—, —CH($CH_3$)—$CH_2$—$CH_2$—, —$CH_2$—CH($CH_3$)—$CH_2$—, —$CH_2$—C($CH_3$)$_2$—, —C($CH_3$)$_2$—$CH_2$—, —CH($CH_3$)—CH($CH_3$)—, —$CH_2$—CH($CH_2CH_3$)—, —CH($CH_2CH_3$)—$CH_2$—, —CH($CH_2CH_2CH_3$)—, —CH(CH($CH_3$))$_2$— and —C($CH_3$)($CH_2CH_3$)—.

By the term "$C_1$-$C_8$-alkylene" (including those which are part of other groups) are meant branched and unbranched alkylene groups with 1 to 8 carbon atoms. By the term "$C_1$-$C_6$-alkylene" are meant branched and unbranched alkylene groups with 1 to 6 carbon atoms. By the term "$C_2$-$C_8$-alkylene" are meant branched and unbranched alkylene groups with 2 to 8 carbon atoms. By the term "$C_2$-$C_6$-alkylene" are meant branched and unbranched alkylene groups with 2 to 6 carbon atoms. By the term "$C_4$-$C_5$-alkylene" are meant branched and unbranched alkylene groups with 4 to 5 carbon atoms. By the term "$C_2$-$C_6$-alkylene" are meant branched and unbranched alkylene groups with 2 to 6 carbon atoms. By the term "$C_1$-$C_4$-alkylene" are meant branched and unbranched alkylene groups with 1 to 4 carbon atoms. By the term "$C_1$-$C_2$-alkylene" are meant branched and unbranched alkylene groups with 1 to 2 carbon atoms. By the term "$C_1$-alkylene" are meant an alkylene groups with 1 carbon atom. By the term "$C_5$-alkylene" are meant branched and unbranched alkylene groups with 5 carbon atoms. By the term "$C_0$-$C_4$-alkylene" are meant branched and unbranched alkylene groups with 0 to 4 carbon atoms, thus also a single bond is encompassed. By the term "$C_0$-$C_3$-alkylene" are meant branched and unbranched alkylene groups with 0 to 3 carbon atoms, thus also a single bond is encompassed. By the term "$C_1$-$C_3$-alkylene" are meant branched and unbranched alkylene groups with 1 to 3 carbon atoms. Examples for $C_1$-$C_8$-alkylene include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene, heptylene or octylene. Unless stated otherwise, the definitions propylene, butylene, pentylene, hexylene, heptylene and octylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

A —$C_1$-alkylene group, which is linked to a structure on two neighbouring ring atoms such that an annellated ring is formed, results to a $C_3$-carbocycle. A —$C_2$-alkylene group, which is linked to a structure on two neighbouring ring atoms such that an annellated ring is formed, results to a $C_4$-carbocycle. A —$C_3$-alkylene group, which is linked to a structure on two neighbouring ring atoms such that an annellated ring is formed, results to a $C_5$-carbocycle. A —$C_4$-alkylene group, which is linked to a structure on two neighbouring ring atoms such that an annellated ring is formed, results to a $C_6$-carbocycle. A —$C_5$-alkylene group, which is linked to a structure on two neighbouring ring atoms such that an annellated ring is formed, results to a $C_7$-carbocycle. A —$C_6$-alkylene group, which is linked to a structure on two neighbouring ring atoms such that an annellated ring is formed, results to a $C_8$-carbocycle.

In the definition of possible substituents, which are linked to such $C_1$-$C_6$-alkylene groups forming a $C_3$-$C_8$-carbocycle, it is to be understood that any of the atoms of the resulting $C_3$-$C_8$-carbocycles could be the linking point for such a substituent.

If the carbon chain is to be substituted by a group which together with one or two carbon atoms of the alkylene chain forms a carbocyclic ring with 3, 5 or 6 carbon atoms, this includes the following examples of the rings:

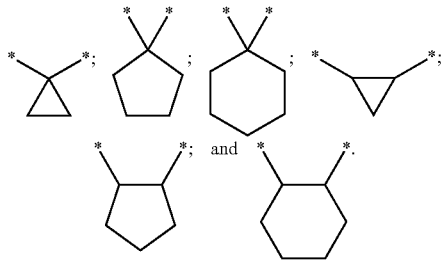

The term "$C_2$-$C_n$-alkenyl", is used for a group as defined in the definition for "$C_1$-$C_n$-alkyl" with at least two carbon atoms, if at least two of those carbon atoms of said group are bonded to each other by a double bond.

By the term "$C_2$-$C_6$-alkenyl" (including those which are part of other groups) are meant branched and unbranched alkenyl groups with 2 to 6 carbon atoms and by the term "$C_2$-$C_4$-alkenyl" are meant branched and unbranched alkenyl groups with 2 to 4 carbon atoms, provided that they have at least one double bond. Alkenyl groups with 2 to 4 carbon atoms are preferred. Examples for $C_2$-$C_6$-alkenyls include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "methenylene" is meant a group with 1 carbon atom, provided that it is linked by a single bond as well as on the other side by a double bond. The asterisks (*) in the structural formula is to be understood as being the linking points to the rest of the molecule, whereas the valency of the rest of the molecule be freed thus a single and a double bond can be formed by replacement of further hydrogens at the binding site if applicable:

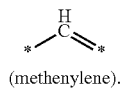

(methenylene).

The term "$C_2$-$C_n$-alkenylene" is used for a group as defined in the definition for "$C_1$-$C_n$-alkylene" with at least two carbon atoms, if at least two of those carbon atoms of said group are bonded to each other by a double bond.

By the term "$C_2$-$C_8$-alkenylene" (including those which are part of other groups) are meant branched and unbranched alkenylene groups with 2 to 8 carbon atoms and by the term "$C_2$-$C_6$-alkenylene" are meant branched and unbranched alkenylene groups with 2 to 6 carbon atoms, provided that they have at least one double bond. By the term "$C_3$-$C_6$-alkenylene" are meant branched and unbranched alkenylene groups with 3 to 6 carbon atoms, provided that they have at least one double bond. By the term "$C_4$-alkenylene" are meant branched and unbranched alkenylene groups with 4 carbon atoms, provided that they have at least one double bond. By the term "$C_1$-$C_2$-alkenylene" are meant alkenylene groups with 1 to 2 carbon atoms, provided that they have at least one double bond, whereas by the term "$C_1$-alkenylene" is meant "methenylene". Examples for $C_2$-$C_8$-alkenylenes include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene, heptenylene or octenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

A —$C_3$-alkenylene group, which is linked to a structure on two neighbouring ring atoms such that an annellated ring is formed, results to a $C_5$-carbocycle. A —$C_4$-alkenylene group, which is linked to a structure on two neighbouring ring atoms such that an annellated ring is formed, results to a $C_6$-carbocycle. A —$C_5$-alkenylene group, which is linked to a structure on two neighbouring ring atoms such that an annellated ring is formed, results to a $C_7$-carbocycle. A —$C_6$-alkenylene group, which is linked to a structure on two neighbouring ring atoms such that an annellated ring is formed, results to a $C_8$-carbocycle.

In the definition of possible substituents, which are linked to such $C_3$-$C_6$-alkenylene groups forming a $C_5$-$C_8$-carbocycle, it is to be understood that any of the atoms of the resulting $C_5$-$C_8$-carbocycles could be the linking point for such a substituent.

The term "$C_2$-$C_n$-alkynyl", is used for a group as defined in the definition for "$C_1$-$C_n$-alkyl" with at least two carbon atoms, if at least two of those carbon atoms of said group are bonded to each other by a triple bond.

By the term "$C_2$-$C_6$-alkynyl" (including those which are part of other groups) are meant branched and unbranched alkynyl groups with 2 to 6 carbon atoms and by the term "$C_2$-$C_4$-alkynyl" are meant branched and unbranched alkynyl groups with 2 to 4 carbon atoms, provided that they have at least one triple bond. Examples for $C_2$-$C_6$-alkynyls include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1-, 2-, and 3-butynyl, 1-methyl-1-propynyl, 1-methyl-2-propynyl etc.

The term "$C_2$-$C_n$-alkynylene" is used for a group as defined in the definition for "$C_1$-$C_n$-alkylene" with at least two carbon atoms, if at least two of those carbon atoms of said group are bonded to each other by a triple bond.

By the term "$C_2$-$C_8$-alkynylene" (including those which are part of other groups) are meant branched and unbranched alkynylene groups with 2 to 8 carbon atoms and by the term "$C_2$-$C_6$-alkynylene" are meant branched and unbranched alkynylene groups with 2 to 6 carbon atoms, provided that they have at least one triple bond. Examples of $C_2$-$C_8$-alkynylenes include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene, heptynylene or octynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems:

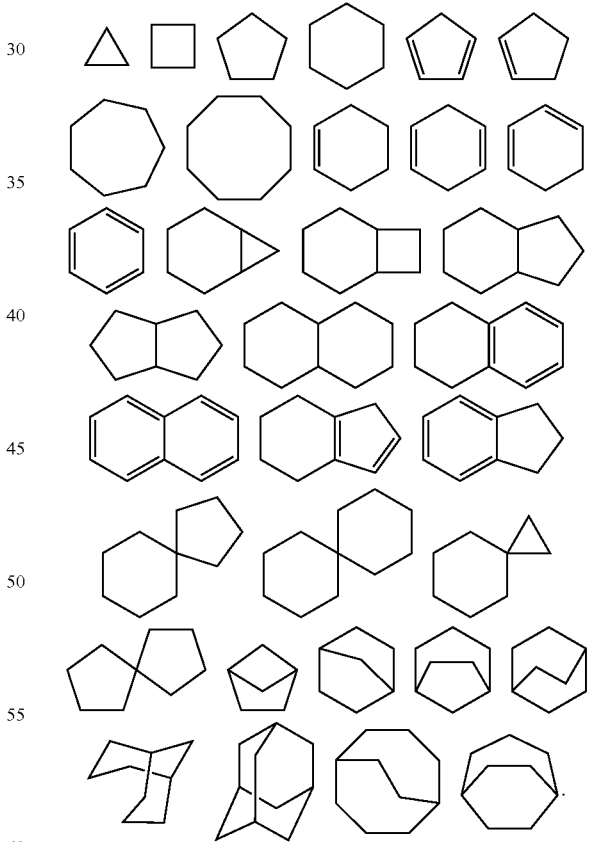

By the term "ring" are meant carbocycles, which can be saturated, unsaturated or aromatic and which optionally can comprise one or more hetero atoms selected from N, O or S.

The term "heterocyclyl" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

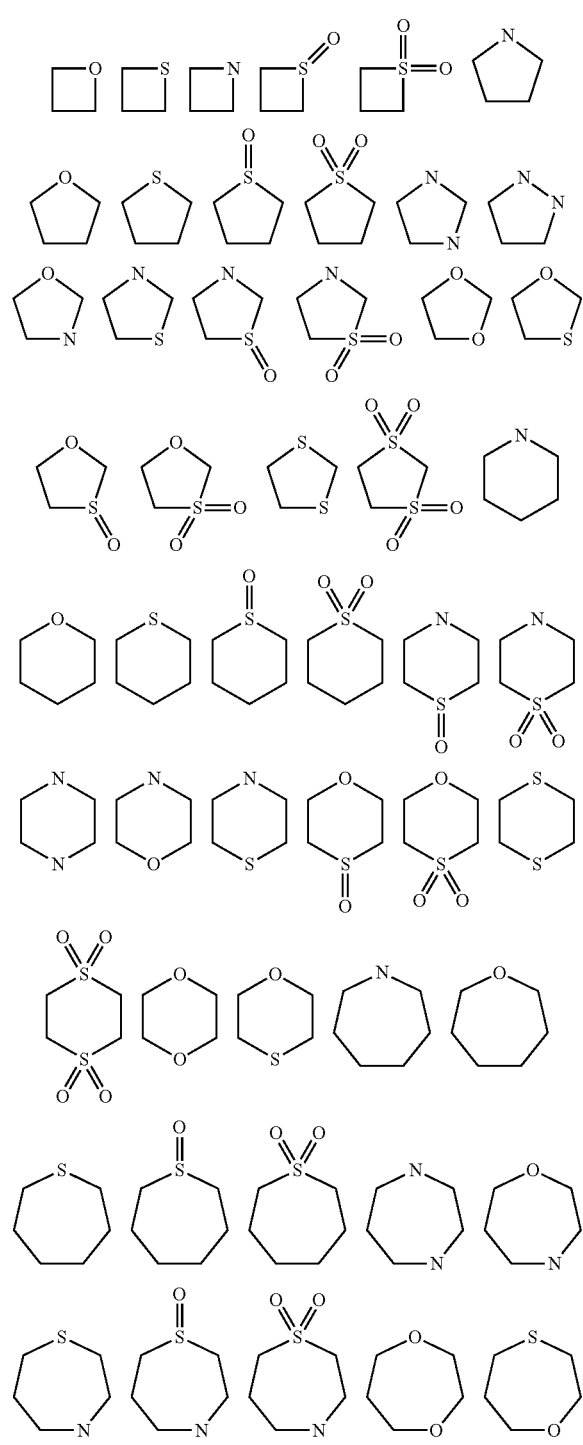
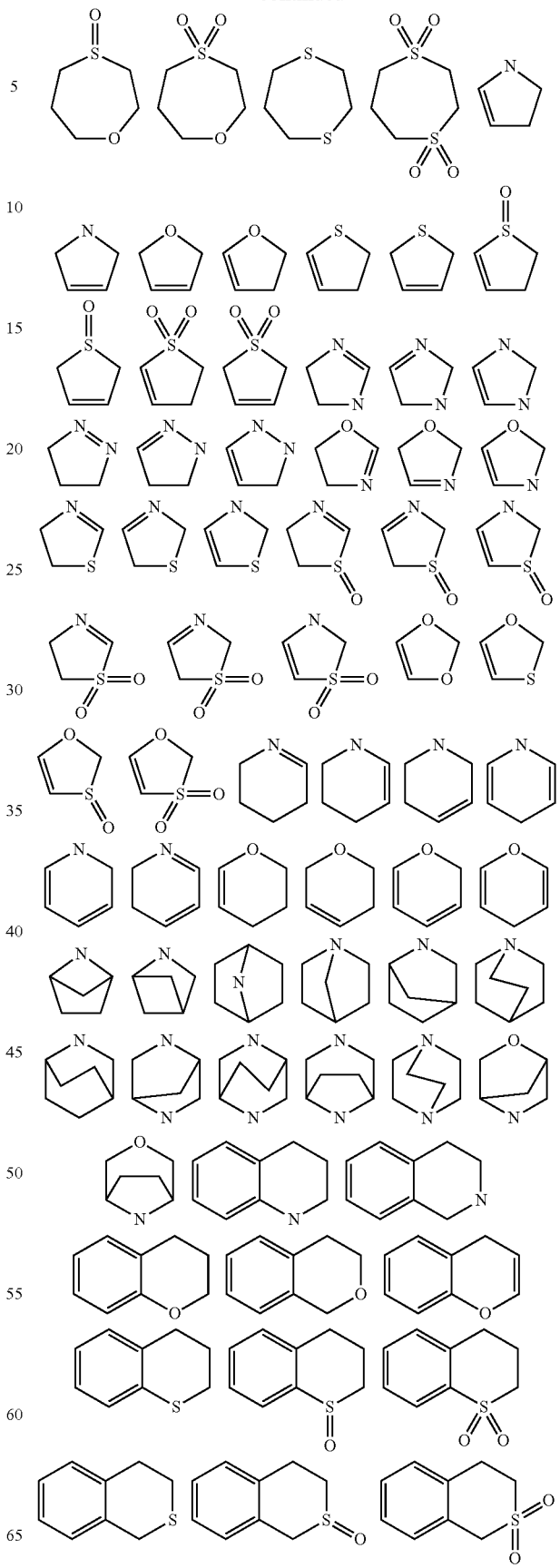

-continued

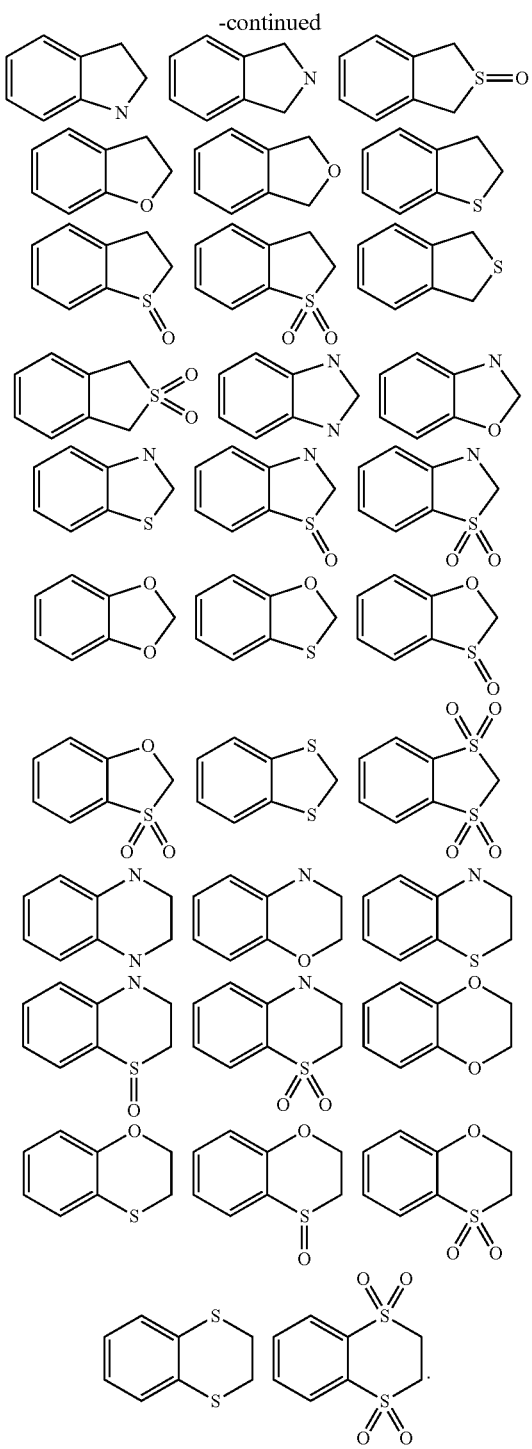

By the term "—C$_3$-C$_8$-heterocyclyl" are meant three-, four-, five-, six-, seven-, or eight-membered, saturated or unsaturated heterocyclic rings which may contain one, two, or three heteroatoms, selected from among oxygen, sulfur, and nitrogen, whereas carbon atoms be replaced by such heteroatoms. The ring may be linked to the molecule through a carbon atom or through a nitrogen atom, if there is one. By the term "—C$_5$-C$_8$-heterocyclyl" are meant five-, six-, seven-, or eight-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. By the term "—C$_5$-heterocyclyl" are meant five-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one. By the term "—C$_6$-heterocyclyl" are meant six-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one.

Examples for C$_5$-heterocyclyl include:

Examples for C$_6$-heterocyclyl include:

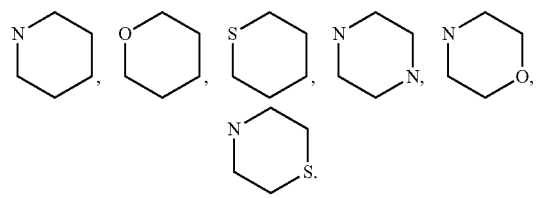

Examples for C$_7$-heterocyclyl include:

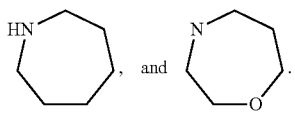

Unless otherwise mentioned, a heterocyclic ring (or "heterocycle") may be provided with a keto group. Examples include:

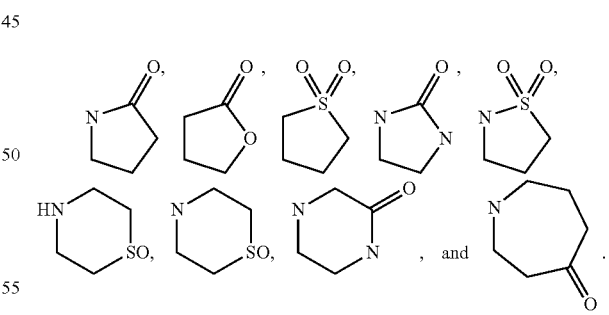

The term "C$_3$-C$_n$-cycloalkyl", wherein n is an integer from 3 to n, either alone or in combination with another radical denotes a cyclic, saturated, unbranched hydrocarbon radical with 3 to n C atoms. For example the term C$_3$-C$_7$-cycloalkyl includes cyclopropyl, cyclobutyl, cyclopentyl, cyclohexyl and cycloheptyl.

By the term "C$_3$-C$_8$-cycloalkyl" (including those which are part of other groups) are meant cyclic alkyl groups with 3 to 8 carbon atoms. Likewise, by the term "C$_3$-C$_6$-cycloalkyl" are meant cyclic alkyl groups with 3 to 6 carbon atoms.

Examples of $C_3$-$C_8$-cycloalkyls include: cyclopropyl, cyclobutyl, cyclopentyl, cyclohexyl, cycloheptyl or cyclooctyl. Unless otherwise stated, the cyclic alkyl groups may be substituted by one or more groups selected from among methyl, ethyl, isopropyl, tert-butyl, hydroxy, fluorine, chlorine, bromine, and iodine.

The term "$C_3$-$C_n$-cycloalkenyl", wherein n is an integer from 3 to n, either alone or in combination with another radical, denotes an cyclic, unsaturated but nonaromatic, unbranched hydrocarbon radical with 3 to n C atoms, at least two of which are bonded to each other by a double bond. For example the term $C_3$-$C_7$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

By the term "aryl" (including those which are part of other groups) are meant aromatic ring systems. By the term "$C_5$-$C_{10}$-aryl" (including those which are part of other groups) are meant aromatic ring systems with 5 to 10 carbon atoms. Preferred are "$C_6$-$C_{10}$-aryl" groups whereas aromatic rings are meant with 6 to 10 carbon atoms. Examples include: phenyl or naphthyl. Also preferred are "$C_5$-$C_6$-aryl" groups whereas aromatic rings are meant with 5 to 6 carbon atoms Unless otherwise stated, the aromatic ring systems may be substituted by one or more groups selected from among methyl, ethyl, iso-propyl, tert-butyl, hydroxy, fluorine, chlorine, bromine and iodine.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

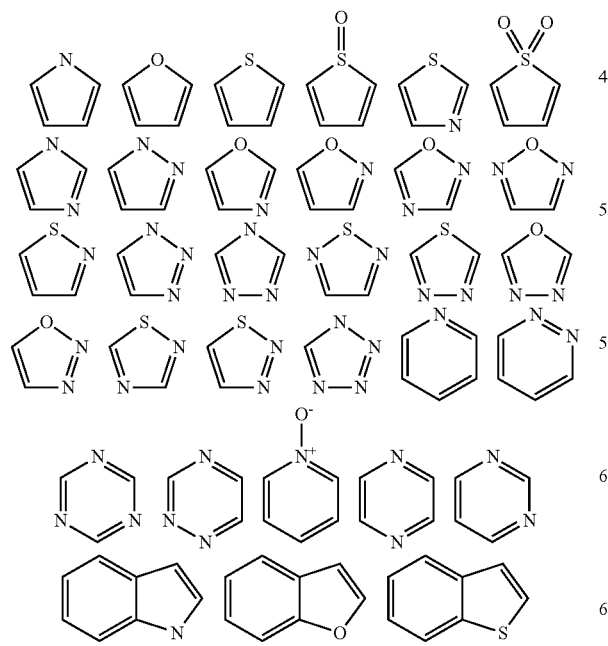

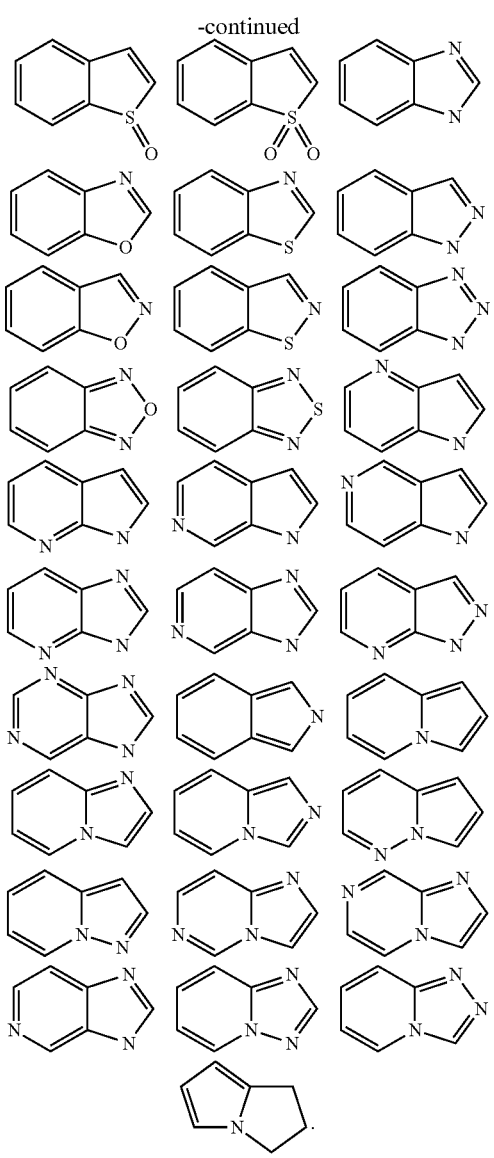

By the term "$C_5$-$C_{10}$-heteroaryl" (including those which are part of other groups) are meant five- or six-membered heterocyclic aromatic groups or 5-10-membered, bicyclic heteroaryl rings which may contain one, two, or three heteroatoms selected from among oxygen, sulfur, and nitrogen, and contain so many conjugated double bonds that an aromatic system is formed. The following are examples of five- or six- or nine-membered heterocyclic aromatic groups:

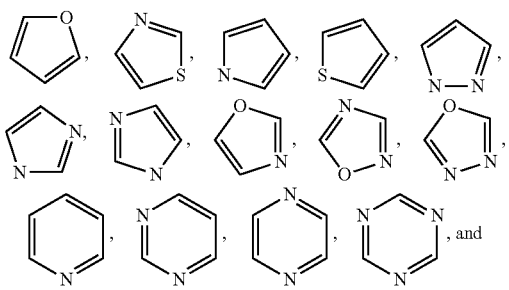

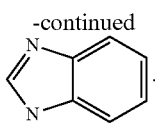

Preferred are "$C_5$-$C_6$-heteroaryl" groups whereas aromatic rings are meant five- or six-membered heterocyclic aromatic groups. Unless otherwise stated, these heteroaryls may be substituted by one or more groups selected from among methyl, ethyl, isopropyl, tert-butyl, hydroxy, fluorine, chlorine, bromine, and iodine.

When a generic combined groups are used, for example —X—$C_1$-$C_4$-alkyl- with X being a functional group such as —CO—, —NH—, —C(OH)— and the like, the functional group X can be located at either of the ends of the —$C_1$-$C_4$-alkyl chain.

By the term "spiro-$C_3$-$C_8$-cycloalkyl" (spiro) are meant 3-8 membered, spirocyclic rings while the ring is linked to the molecule through a carbon atom, and whereas the resulting 3-8 membered carbocycle is formed by alkylene groups with 2 to 7 carbon atoms. By the term "spiro —$C_5$-cycloalkyl" (spiro) are meant 5 membered, spirocyclic rings while the ring is linked to the molecule through a carbon atom, whereas the resulting 5 membered carbocycle is formed by an alkylene group with 4 carbon atoms. By the term "spiro-$C_3$-$C_8$-cycloalkenyl" (spiro) are meant 3-8 membered, spirocyclic rings while the ring is linked to the molecule through a carbon atom, whereas the resulting 3-8 membered carbocycle is formed by alkenylene groups with 2 to 7 carbon atoms. By the term "spiro —$C_5$-cycloalkenyl" (spiro) are meant 5 membered, spirocyclic rings while the ring is linked to the molecule through a carbon atom, whereas the resulting 5 membered carbocycle is formed by alkenylene groups with 4 carbon atoms.

By the term "spiro-$C_3$-$C_8$-heterocyclyl" (spiro) are meant 3-8 membered, saturated or unsaturated, spirocyclic rings which may contain one, two, or three heteroatoms selected from among oxygen, sulfur, and nitrogen, while the ring may be linked to the molecule through a carbon atom or through a nitrogen atom, if there is one. By the term "spiro-$C_5$-heterocyclyl" (spiro) are meant 5 membered, saturated or unsaturated, spirocyclic rings which may contain one, two, or three heteroatoms selected from among oxygen, sulfur, and nitrogen, while the ring may be linked to the molecule through a carbon atom or through a nitrogen atom, if there is one.

Unless otherwise mentioned, a spirocyclic ring may be provided with an oxo, methyl, or ethyl group. Examples include:

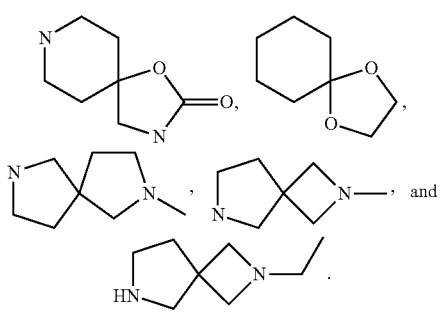

"Halogen" within the scope of the present invention denotes fluorine, chlorine, bromine or iodine. Unless stated to the contrary, fluorine, chlorine and bromine are regarded as preferred halogens.

"Linker" within the scope of the present invention denominates a bivalent group or a bond.

The above listed groups and residues can be combined to form more complex structures composed from carbon chains and rings or the like.

Compounds of general formula (I) may have acid groups, chiefly carboxyl groups, and/or basic groups such as e.g. amino functions. Compounds of general formula (I) may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alklaline earth metal hydroxides or carbonates, zinc or ammonium hydroxides or organic amines such as e.g. diethylamine, triethylamine, triethanolamine inter alia.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19). The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

As mentioned hereinbefore, the compounds of formula (I) may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula (I) with inorganic or organic acids. On the other hand the compound of formula (I) may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula (I) are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (I) may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Hence the invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may optionally occur as racemates, but they may also be obtained as pure enantiomers/diastereomers.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to formula (I) according to the invention have the meanings hereinbefore whereas in particular the preferred embodiments defined by HET, $R_1$, $R_2$, $R_3$, $R_4$, $R_5$, $R_6$, $R_7$, $R_8$, $R_9$, $R_{10}$, $R_{10'}$, $R_{11}$, $R_{11'}$, $R_{12}$, $R_{13}$, $R_{14}$, $R_{15}$, $R_{16}$, $L_1$, E, G, Z, A, m, and n in each case are independently selected of one another.

Therapeutic Applications

The above exemplary substances have been tested for binding to CCR2 using a binding assay as outlined herein below:

Cell Culture:

THP-1 cells (human acute monocytic leukaemia cells) were cultured under standardized conditions at 37° C. and 5% CO2 in a humidified incubator. THP-1 cells were cultivated in RPMI 1640 medium (Gibco 21875) containing 1% MEM-NEAA (Gibso 11140) 2 mM L-glutamine, 1.5 g/L sodium bicarbonate, 4.5 g/L glucose, 10 mM HEPES and 1.0 mM sodium pyruvate, 90%; 10% fetal calf serum (FCS Gibco 10500-064).

Membranes were prepared from THP-1 cells. THP-1 cells were centrifuged at 300×g at 4° C. for 10 min. The cell pellet was resuspended in Phosphate Buffer Saline (PBS, including 10 µM Pefabloc and a protease inhibitor mix 'complete', Boehringer Mannheim (1 tablet/50 ml)), to a concentration of 80 cells/ml. The membrane preparation was performed by disrupting the cells by nitrogen decomposition (at 50 bar, for 1 h) in a "Nitrogen Bombe" (Parr Instrument). Cell debris was removed by centrifugation (800×g at 4° C., 1 min). The supernatant was centrifuged at 80000×g, 4° C. for 30 min to sediment the cell membranes. Usually 50 mg of protein (Bradford assay) were yielded from 1×10E9 cells. The membranes were resuspended in 25 mM HEPES, 25 mM $MgCl_2$, 1 mM $CaCl_2$, 10% Glycerine for storage in aliquots at −80° C. in 25 mM HEPES, 25 mM $MgCl_2$, 1 mM $CaCl_2$, 10% Glycerine and stored at −80° C.

Receptor Membrane Binding Assay:

Perkin Elmer NEX 332 Jod 125 MCP-1, Stock: 2200 Ci/mmol solved in 2000 µA assay buffer, stored at −20° C. THP-1 membrane were adjusted with 25 mM HEPES, pH 7.2; 5 mM $MgCl_2$; 0.5 mM $CaCl_2$; 0.2% BSA assay buffer to a concentration of 2.5 µg/15 µl. Amersham Biosciences PVT-WGA Beads (RPNQ0001) were adjusted with assay buffer to a concentration of 0.24 mg/30 µl. For preparation of the membrane-bead-suspension membranes and beads were incubated for 30 min at RT under rotation (60 rpm) with a ratio of 1:2. Test compounds dissolved in 100% DMSO to a concentration of 10 mM and are further diluted with 100% DMSO to 1 mM. All additional compound dilutions were obtained with assay buffer, final 1% DMSO. Compounds, membrane-bead-suspension and [$^{125}$I]MCP-1 (ca. 25000 cpm/10 µl) were incubated. Bound radioactivity was determined by scintillation counter after 8 h. Determination of affinity of test compounds (dissociation constant hKi) is calculated by iterative fitting of experimental data using the "easy sys" program, which is based on law of mass action (Schittkowski K. (1994), Numerische Mathematik, Vol. 68, 129-142).

All of the referenced examples have been found to have an activity in this assay of 10 µM or less.

| Example | hKi [nM] |
|---------|----------|
| 1 | 15 |
| 2 | 507 |
| 3 | 3693 |
| 4 | 1088 |
| 5 | 4170 |

| Example | hKi [nM] |
|---|---|
| 6 | 1642 |
| 7 | 27 |
| 8 | 11 |
| 9 | 2155 |
| 10 | 14 |
| 11 | 2156 |
| 12 | 1102 |
| 13 | 739 |
| 14 | 1613 |
| 15 | 732 |
| 16 | 1513 |
| 17 | 1049 |
| 18 | 331 |
| 19 | 3617 |
| 20 | 480 |
| 21 | 4414 |
| 22 | 3790 |
| 23 | 455 |
| 24 | 1299 |
| 25 | 657 |
| 26 | 1968 |
| 27 | 661 |
| 28 | 3685 |
| 29 | 241 |
| 30 | 1360 |
| 31 | 1712 |
| 32 | 3605 |
| 33 | 2106 |
| 34 | 4252 |
| 35 | 2859 |
| 36 | 1273 |
| 37 | 18 |
| 38 | 168 |
| 39 | 49 |
| 40 | 304 |
| 41 | 432 |
| 42 | 230 |
| 43 | 49 |
| 44 | 3920 |
| 45 | 1171 |
| 46 | 1174 |
| 47 | 1096 |
| 48 | 159 |
| 49 | 161 |
| 50 | 451 |
| 51 | 405 |
| 52 | 270 |
| 53 | 172 |
| 54 | 636 |
| 55 | 235 |
| 56 | 1022 |
| 57 | 189 |
| 58 | 4242 |
| 59 | 42 |
| 60 | 5 |
| 61 | 309 |
| 62 | 590 |
| 63 | 4 |
| 64 | 13 |
| 65 | 16 |
| 66 | 22 |
| 67 | 21 |
| 68 | 50 |
| 69 | 62 |
| 70 | 3564 |
| 71 | 2098 |
| 72 | 104 |
| 73 | 52 |
| 74 | 552 |
| 75 | 657 |
| 76 | 3403 |
| 77 | 410 |
| 78 | 1251 |
| 79 | 925 |
| 80 | 101 |
| 81 | 2324 |
| 82 | 203 |
| 83 | 698 |
| 84 | 41 |
| 85 | 5 |
| 62a | 566 |
| 62b | 357 |
| 62c | 351 |
| 62d | 305 |
| 62e | 419 |
| 62f | 9558 |
| 62g | 538 |
| 62h | 983 |
| 62i | 184 |
| 62j | 516 |
| 62k | 12 |
| 62l | 1382 |
| 62m | 300 |
| 62n | 192 |
| 62o | 1078 |
| 62p | 119 |
| 62q | 780 |
| 62r | 411 |
| 62s | 5144 |
| 62t | 17 |
| 62u | 114 |
| 62w | 54 |
| 62y | 12 |
| 62z | 30 |
| 62aa | 89 |
| 62ab | 16 |
| 62ac | 1000 |
| 62ad | 336 |
| 62ae | 49 |
| 62af | 257 |
| 62ag | 40 |
| 62ah | 41 |
| 62ai | 34 |
| 62aj | 35 |
| 62ak | 145 |
| 62al | 128 |
| 69a | 30 |
| 69b | 9 |
| 69c | 28 |
| 69d | 11 |
| 69e | 1 |
| 69f | 17 |
| 69g | 1300 |
| 69h | 39 |
| 62x | 18 |
| 62am | 12 |
| 62an | 12 |
| 69i | 4 |
| 69j | 1 |
| 69k | 29 |
| 69l | 14 |
| 69m | 16 |
| 69n | 24 |
| 69o | 10 |
| 69p | 6 |
| 69q | 0.7 |
| 69r | 7 |
| 69s | 8 |
| 69t | 2 |
| 69u | 3 |
| 69w | 5 |
| 69x | 0.7 |
| 69y | 7 |
| 69z | 13 |
| 69ab | 37 |
| 69ac | 96 |

Based on the ability of the substances described by formula (I) to effectively bind to CCR2 a range of therapeutic applications can be envisaged. The present invention provides a method for modulating or treating at least one MCP-1 related disease, in a cell, tissue, organ, animal, or patient, as known in the art or as described herein, using at least one CCR2 antagonist of the present invention. The present invention also provides a method for modulating or treating at least one MCP-1 related disease, in a cell, tissue, organ, animal, or patient including, but not limited to, at least one of malignant disease, metabolic disease, an immune or inflammatory related disease, a cardiovascular disease, an infectious disease, or a neurologic disease. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the CCR2 antagonists are useful for the treatment of diseases that involve inflammation such as COPD, angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The antagonists may also be useful in the treatment of various fibrotic diseases such as idiopathic pulmonary fibrosis, diabetic nephropathy, hepatitis, and cirrhosis. Thus, the present invention provides a method for modulating or treating at least one CCR2 related disease, in a cell, tissue, organ, animal, or patient, as known in the art or as described herein, using at least one CCR2 antagonist of the present invention. Particular indications are discussed below:

Pulmonary Diseases

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs iricludeing hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar, proteinosis, bronchiectasis, pleural disorders, atelectasis, cystic fibrosis, and tumors of the lung, and pulmonary embolism.

Malignant Diseases

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Diseases

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitisluveitisloptic neuritis, idiopathic pulmonary fibrosis, systemic vasculitis/wegener's granulomatosis, sarcoidosis, orchitislvasectomy reversal procedures, allergiclatopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, traumalhemo~~hage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic diseases, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type IU hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal garnrnopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like.

Cardiovascular Diseases

The present invention also provides a method for modulating or treating at least one cardiovascular disease in a cell, tissue, organ, animal, or patient, including, but not limited to, at least one of cardiac 25 stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythrnias, ventricular fibrillation, H is bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one CCR2 antagonist to a cell, tissue, organ, animal or patient in need of such modulation, treatment or therapy.

Neurologic Diseases

The present invention also provides a method for modulating or treating at least one neurologic disease in a cell, tissue, organ, animal or patient, including, but not limited to, at least one of: Inflammatory pain, chronic pain, Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain; neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi. system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like.

Fibrotic Conditions

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoirnrnune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one wound, trauma or tissue injury or chronic condition resulting from or related thereto, in a cell, tissue, organ, animal or patient, including, but not limited to, at least one of: bodily injury or a trauma associated with surgery including thoracic, abdominal, cranial, or oral surgery; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is also amenable to CCR2 antagonist therapy as the first cells to invade the wound area are neutrophils followed by monocytes which are activated by macrophages. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen. Almost all tissue repair processes include the early connective tissue formation, a stimulation of this and the subsequent processes improve tissue healing, however, overproduction of connective tissue and collegen can lead to a fibrotic tissue characterized as inelastic and hypoxic. The CCR2 antagonist of the invention can be used in methods for modulating, treating or preventing such sequelae of wound healing.

Other Therapeutic Uses of CCR2 Antagonists

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection, HIV neuropathy, meningitis, hepatitis (A, B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitislepidydimitis, *legionella*, lyme disease, influenza a, epstein-barr virus, vital-associated hemaphagocytic syndrome, vital encephalitisiaseptic meningitis, and the like.

Any method of the present invention can comprise administering an effective amount of a composition or pharmaceutical composition comprising at least one CCR2 antagonist to a cell, tissue, organ, animal or patient in need of such modulation, treatment or therapy. Besides being useful for human treatment, these compounds are also useful for veterinary treatment of companion animals, exotic animals and farm animals, including mammals, rodents, and the like.

Combinations

The compounds of formula (I) may be used on their own or in conjunction with other active substances of formula (I) according to the invention. If desired the compounds of formula (I) may also be used in combination with other pharmacologically active substances. It is preferable to use for this purpose active substances selected for example from among β2-adrenoceptor-agonists (short and lon-acting betamimetics), anti-cholinergics (short and lon-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, JNK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinflammatory drugs (NSAIDs) including COX-2 inhibitors, CRTH2 antagonists, DP1-receptor modulators, Thromboxane receptor antagonists, CCR1 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR1 antagonists, CXCR2 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, antiviral drugs, opiate receptor agonists, cannabionoid agonists, sodium channel blockers, N-type calcium channel blockers, serotonergic and noradrenergic modulators, proton pump inhibitors, local anesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

The betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy- 3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the beta mimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the acid addition salts of the betamimetics are preferably selected from among hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonat, preferably hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl-cyclopropyltropine 4,4'-difluorobenzilate methobromide, tropenol 9-hydroxy-xanthene-9-carboxylate-methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, $(-)_p$-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl [4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

The PDE4-inhibitor used are preferably compounds selected from among enprofyllin, roflumilast, ariflo (cilomilast), arofyllin, atizoram, AWD-12-281 (GW-842470), T-440, T-2585, PD-168787, V-11294A, Cl-1018, CDC-801, D-22888, YM-58997, Z-15370, N-(3,5-dichloro-1-oxo-pyridin-4-yl)-4-difluoromethoxy-3-cyclopropylmethoxybenzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-4(R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2- buten-1-yl]amino}-7-[(tetrahydro furan-2-yl)methoxy]-quinazoline, 4-[(3-chloro-4-fluorophenyl)amino]-6-({[4N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxy-carbonyl)-piperidin-4-yloxy]-7-methoxy-quinazoline, 4-[(3-chloro-4-fluoro-phenyl)amino]-6-(trans-4-amino-cyclo-hexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methane-sulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2.6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)

amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, Cetuximab, Trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quino line, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydro furan-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydro furan-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3- chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2.6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydro furan-2-yl) methoxy]-quinazoline, 4-[(3-chloro-4-fluoro-phenyl) amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and Cetuximab, optionally in the form of the racemates, enantiomers or diastereomers thereof, optionally in the form of the pharmacologically acceptable acid addition salts, the solvates and/or hydrates thereof.

Preferable the EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl) amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydro furan-2-yl)methoxy]-quinazoline, 4-[(3-ethynyl-phenyl)amino]-6,7-bis-(2-methoxy-ethoxy)-quinazoline, 4-[(R)-(1-phenyl-ethyl) amino]-6-(4-hydroxy-phenyl)-7H-pyrrolo[2,3-d] pyrimidine, 3-cyano-4-[(3-chloro-4-fluorophenyl)amino]-6-{[4-(N,N-dimethylamino)-1-oxo-2-buten-1-yl]amino}-7-ethoxy-quino line, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-ethynyl-phenyl)amino]-6-{[4-(5.5-dimethyl-2-oxo-morpholin-4-yl)-1-oxo-2-buten-1-yl] amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl) amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro- 4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

EGFR-inhibitors are preferably selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-β-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

MRP4-inhibitors are preferably selected from among N-acetyl-dinitrophenyl-cysteine, dehydroepiandrosterone 3-sulphate, dilazep, dinitrophenyl-5-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof. Particularly preferred MRP4-inhibitors are selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydrop-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the CCR2 inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline, L-NA ($N^{\omega}$-nitro-L-arginine), L-NAME ($N^{\omega}$-nitro-L-arginine methylester), L-NMMA ($N^{G}$-monomethyl-L-arginine), L-NIO ($N^{\omega}$-iminoethyl-L-ornithine), L-NIL ($N^{\omega}$-iminoethyl-lysine), (S)-6-acetimidoylamino-2-aminohexanoic acid (1H-tetrazol-5-yl)-amide (SC-51) (J. Med. Chem. 2002, 45, 1686-1689), 1400W, (S)-4-(2-acetimidoylamino-ethylsulphanyl)-2-amino-butyric acid (GW274150) (Bioorg. Med. Chem. Lett. 2000, 10, 597-600), 2-[2-(4-methoxy-pyridin-2-yl)-ethyl]-3H-imidazo[4,5-b]pyridine (BYK191023)(Mol. Pharmacol. 2006, 69, 328-337), 2-((R)-3-amino-1-phenyl-propoxy)-4-chloro-5-fluorobenzonitrile (WO 01/62704), 2-((1R.3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamines such as e.g. AR-C102222 (J. Med. Chem. 2003, 46, 913-916), (1S,5S,6R)-7-chloro-5-methyl-2-aza-bicyclo[4.1.0]hept-2-en-3-ylamine (ONO-1714) (Biochem. Biophys. Res. Commun. 2000, 270, 663-667), (4R.5R)-5-ethyl-4-methyl-thiazolidin-2-ylideneamine (Bioorg. Med. Chem. 2004, 12, 4101), (4R.5R)-5-ethyl-4-methyl-selenazolidin-2-ylideneamine (Bioorg. Med. Chem. Lett. 2005, 15, 1361), 4-aminotetrahydrobiopterine (Curr. Drug Metabol. 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330)(Eur. J. Pharmacol. 2005, 509, 71-76), 3-(2,4-difluoro-phenyl)-6-[2-(4-imidazol-1-ylmethyl-phenoxy)-ethoxy]-2-phenyl-pyridine (PPA250) (J. Pharmacol. Exp. Ther. 2002, 303, 52-57), methyl 3-{[(benzo[1.3]dioxol-5-ylmethyl)-carbamoyl]-methyl}-4-(2-imidazol-1-yl-pyrimidin-4-yl)-piperazin-1-carboxylate (BBS-1) (Drugs Future 2004, 29, 45-52), (R)-1-(2-imidazol-1-yl-6-methyl-pyrimidin-4-yl)-pyrrolidine-2-carboxylic acid (2-benzo[1.3]dioxol-5-yl-ethyl)-amide (BBS-2) (Drugs Future 2004, 29, 45-52) and the pharmaceutical salts, prodrugs or solvates thereof.

Compounds which may be used as SYK-inhibitors are preferably compounds selected from among: R343 or R788.

Examples of preferred MAP kinase inhibitors, as for example p38, ERK1, ERK2, JNK1, JNK2, JNK3 or SAP, which may be mentioned include SCIO-323, SX-011, SD-282, SD-169, NPC-037282, SX-004, VX-702, GSK-681323, GSK-856553, ARRY-614, ARRY-797, ARRY-438162, ARRY-p38-002, ARRY-371797, AS-602801, AS-601245, AS-602183, CEP-1347, KC706, TA-5493, RO-6226, Ro-1487, SC-409, CBS-3595, VGX-1027, PH-797804, BMS-582949, TA-5493 and BIRB-796 optionally in racemic form, as enantiomers, diastereomeres or as pharmacologically acceptable salts, solvates or hydrates.

Examples of preferred inhibitors of the NF-κB signalling pathway including IKK2 kinase inhibitors which may be mentioned include: MD-1041, MLN-041 und AVE-0547 optionally in racemic form, as enantiomers, diastereomeres or as pharmacologically acceptable salts, solvates or hydrates.

Examples of preferred Leukotriene biosynthesis inhibitors, as for example 5-Lipoxygenase (5-LO) inhibitors, cPLA2 inhibitors, Leukotriene A4 hydrolase inhibitors oder FLAP inhibitors, which may be mentioned include zileuton, tipelukast, licofelone, darapladib, TA-270, IDEA-033, IDEA-070, NIK-639, ABT-761, fenleuton, tepoxalin, AM-103, AM-803, Abbott-79175, Abbott-85761, PLT-3514, CMI-903, PEP-03, CMI-977, MLN-977, CMI-947, LDP-977, efipladib, PLA-695, veliflapon, MK-591, MK-886 und BAYx1005 optionally in racemic form, as enantiomers, diastereomeres or as pharmacologically acceptable salts, solvates or hydrates.

Examples of preferred non-steroidal anti-inflammatory agents (NSAIDs) which may be mentioned include COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) optionally in racemic form, as enantiomers, diastereomeres or as pharmacologically acceptable salts, solvates or hydrates.

Examples of preferred CCR1 antagonists which may be mentioned include AZD-4818, CCX-354, MLN-3701, MLN-3897, optionally in racemic form, as enantiomers, diastereomeres or as pharmacologically acceptable salts, solvates or hydrates.

Examples of preferred CCR5 antagonists which may be mentioned include maraviroc, INCB-15050. CCR5mAb004, GSK-706769, PRO-140, SCH-532706, vicriviroc and nifeviroc optionally in racemic form, as enantiomers, diastereomeres or as pharmacologically acceptable salts, solvates or hydrates.

Examples of preferred CXCR1 or CXCR2 antagonists which may be mentioned include SCH-527123 and SB-656933 optionally in racemic form, as enantiomers, diastereomeres or as pharmacologically acceptable salts, solvates or hydrates.

Examples of preferred Neurokinin (NK1 or NK2) antagonists which may be mentioned include Saredutant, Nepadutant, PRX-96026 and Figopitant optionally in racemic form, as enantiomers, diastereomeres or as pharmacologically acceptable salts, solvates or hydrates.

Examples of preferred purinergic receptor modulators, including P2X7 inhibitors, which may be mentioned include AZD-9056 optionally in racemic form, as enantiomers, diastereomeres or as pharmacologically acceptable salts, solvates or hydrates.

Examples of preferred PPAR gamma modulators which may be mentioned include Rosiglitazone, Ciglitazone, Pioglitazone and SMP-028 optionally in racemic form, as enantiomers, diastereomeres or as pharmacologically acceptable salts, solvates or hydrates.

Examples of preferred Interleukin 1-beta converting enzyme (ICE) inhibitors which may be mentioned include Pralnacasan, VRT-18858, RU-36384, VX-765 and VRT-43198 optionally in racemic form, as enantiomers, diastereomeres or as pharmacologically acceptable salts, solvates or hydrates.

Examples of preferred Toll-like receptor (TLR) modulators which may be mentioned include Resiquimod, PF-3512676, AVE-0675, Heplisav, IMO-2055, CpG-28, TAK-242, SAR-21609, RC-52743198 and 852A optionally in racemic form, as enantiomers, diastereomeres or as pharmacologically acceptable salts, solvates or hydrates.

Examples of preferred VLA4 antagonists which may be mentioned include Natalizumab, Valategrast, TBC-4746, CDP-323 and TL-1102 optionally in racemic form, as enantiomers, diastereomeres or as pharmacologically acceptable salts, solvates or hydrates.

Examples of preferred ICAM-1 inhibitors which may be mentioned include BIRT-2584 optionally in racemic form, as enantiomers, diastereomeres or as pharmacologically acceptable salts, solvates or hydrates.

Examples of preferred anti-TNF antibodies which may be mentioned include Infliximab, Adalimumab, Golimumab. CytoFab and Etanercept.

Examples of preferred mucoregulators which may be mentioned include MSI-2216, Erdosteine, Fluorovent, Talniflumate, INO-4995, BIO-11006, VR-496 and fudosteine optionally in racemic form, as enantiomers, diastereomeres or as pharmacologically acceptable salts, solvates or hydrates.

Examples of preferred Antiviral drugs which may be mentioned include acyclovir, tenovir, pleconaril, peramivir, pocosanol.

Examples of preferred Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol.

Examples of preferred opiate receptor agonists are selected from among morphine, propoxyphene (Darvon), tramadol, buprenorphin.

Examples of preferred anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab.

Examples of preferred IL-1 receptor antagonists such as but not limited to Kineret; Sodium channel blockers: carbamazepine, mexiletine, lamotrigine, tectin, lacosamide Examples of preferred N-type calcium channel blockers are selected from among Ziconotide.

Examples of preferred Serotonergic and noradrenergic modulators such as but not limited to paroxetine, duloxetine, clonidine, amitriptyline, citalopram;

Examples of preferred Histamine H1 receptor antagonists such as but not limited to bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, desloratadine, fexofenadine and levocetirizine.

Examples of preferred Histamine H2 receptor antagonists such as but not limited to cimetidine, famotidine and ranitidine.

Examples of preferred proton pump inhibitors such as but not limited to omeprazole, pantoprazole and esomeprazole.

Examples of preferred Leukotriene antagonists and 5-lipoxygenase inhibitors such as but not limited to zafirlukast, montelukast, pranlukast and zileuton.

Examples of preferred local anesthetics such as but not limited to ambroxol, lidocaine.

Examples of preferred potassium channel modulators such as but not limited to retigabine.

Examples of preferred GABA modulators such as but not limited to lacosamide, pregabalin, gabapentin.

Examples of preferred anti-migraine drugs such as but not limited to sumatriptan, zolmitriptan, naratriptan, eletriptan, telcegepant.

Examples of preferred NGF antibodies such as but not limited to RI-724.

Combination therapy is also possible with new principles for the treatment of pain e.g. P2X3 antagonists, VR1 antagonists, NK1 and NK2 antagonists, NMDA antagonists, mGluR antagonists and the like.

Pharmaceutical Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (I) according to the preferred embodiments above.

It is particularly preferable if the compounds of formula (I) are administered orally, and it is also particularly preferable if they are administered once or twice a day. Suitable tablets may be obtained, for example, by mixing the active substance (s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the active substances of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH. Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. For the treatment forms described above, ready-to-use packs of a medicament for the treatment of respiratory complaints are provided, containing an enclosed description including for example the words respiratory disease, COPD or asthma, a pteridine and one or more combination partners selected from those described above.

Experimental Procedures and Synthetic Examples

LIST OF ABBREVIATIONS

ACN acetonitrile
APCI atmospheric pressure chemical ionization (in MS)
Ctrl control
DAD diode array detector
DMA N,N-dimethylacetamide'
DMF N,N-dimethylformamide
DMSO dimethyl sulfoxide
EI electron impact (in MS)
ESI electrospray ionization (in MS)
ex example
GC/MS gas chromatography with mass spectrometric detection
h hour(s)
HATU O-(7-azabenzotriazol-1-yl)-N,N,N',N'-tetramethyluronium hexafluoro-phosphate
HPLC high performance liquid chromatography
HPLC/MS coupled high performance liquid chromatography-mass spectrometry
min minutes
MS mass spectrometry
NMR nuclear magnetic resonance
NMP N-Methyl-2-pyrrolidinone
$R_t$ retention time (in HPLC)
sec secondary
TBTU O-(1H-benzo-1,2,3-triazol-1-yl)-N,N,N',N'-tetramethyluronium tetrafluoroborate
tert tertiary
TFA trifluoroacetic acid
THF tetrahydrofurane
TLC thin-layer chromatography
UV ultraviolet absorption
Analytical Methods
HPLC Methods
Methods:
  1E
  Column: Symmetry C8, 5 µm, 3×150 mm
  Mobile phase: A=(10 mM aqueous solution of NH$_4$COOH)+10% ACN;
  B=ACN+10% (10 mM aqueous solution of NH$_4$COOH).
  Flow rate: 1200 µL/min
  Gradient: A (100%) for 1.5 min then to B (100%) in 10 min for 3 min
  1E (Hydro)
  Column: Synergy Hydro RP80A, 4 µm, 4.6×100 mm
  Mobile phase: A=(10 mM aqueous solution of NH$_4$COOH)+10% ACN;
  B=ACN+10% (10 mM aqueous solution of NH$_4$COOH).
  Flow rate: 1200 µL/min Gradient: A (100%) for 1.5 min then to B (100%) in 10 min for 3 min
1E f
Column: Synergi Fusion RP80A, 4 μm, 4,6×100 mm
Mobile phase: A=(10 mM aqueous solution of NH₄COOH)+10% ACN;
B=ACN+10% (10 mM aqueous solution of NH₄COOH).
Flow rate: 1200 μL/min
Gradient: A (100%) for 1.5 min then to B (100%) in 10 min for 3 min
Equipment:
Instrument: HPLC/MS ThermoFinnigan HPLC Surveyor DAD,
Detection: UV @ 254 nm
Detection: Finnigan MSQ, quadrupole
Ion source: APCI
Method:
2F
Column: Symmetry Shield RP8, 5 μm, 4.6×150 mm
Mobile phase: A=(H₂O+HCOOH 0.1%)+10% ACN
B=ACN+10% (H₂O+0.1% HCOOH)
Flow rate: 1000 μL/min
Gradient: A/B (95/5%) for 1.5 min then to A/B (5/95%) in 10 min for 1.5 min
Equipment:
Instrument: HPLC/MS ThermoFinnigan HPLC Surveyor DAD,
LCQDuo Ion Trap
Detection: UV λ 254 nm
Detection: Finnigan LCQDuo Ion Trap
Ion source: ESI
UV 220-300 nm
Method:
2FF
Column: Symmetry Shield RP8, 5 μm, 4.6×150 mm
Mobile phase: A=(H₂O+HCOOH 0.1%)+10% ACN
B=ACN+10% (H₂O+0.1% HCOOH)
Flow rate: 1000 μL/min
Gradient: A/B (95/5%) for 1.5 min then to A/B (5/95%) in 10 min for 1.5 min
Equipment:
Instrument: HPLC/MS ThermoFinnigan HPLC Surveyor DAD,
LCQFLEET Ion Trap
Detection: UV λ 254 nm
Detection: Finnigan LCQDuo Ion Trap
Ion source: ESI
Method:
2G
Column: BEH C18, 1.7 um, 2.1×100 mm
Mobile phase: A=(NH4COOH 5 mM)+10% ACN
B=ACN+10% (NH4COOH 5 mM)
Flow rate: 450 μL/min
Gradient: A/B (100/0%) for 0.67 min, then to A/B (0/100%) in 3.70 min, then A/B (0/100%) for 0.47 min
2Ga
Column: ACQUITY UPLC BEH C18, 1.7 um, 2.1×50 mm
Mobile phase: A=(NH4COOH 5 mM)+10% ACN
B=ACN+10% (NH4COOH 5 mM)
Flow rate: 700 μL/min
Gradient: from A/B (100/0%) to A/B (0/100%) in 2.4 min, then A/B (0/100%) for 0.3 min
Equipment:
Instrument: Acquity UPLC/MS WATERS
Detection: Waters PDA (total scan)
Detection: Waters ELSD
Detection: Waters SQD
Ion source: ESI
Method:
2Ha

| Column: | MERCK; Chromolith Flash; RP18e; 25 × 4.6 mm |
| --- | --- |
| Mobile phase: | A = Water + 0.1% HCOOH; B = ACN + 0.1% HCOOH |
| Flow rate: | 1.6 μL/min |

|  | % FM B | Minutes |
| --- | --- | --- |
| Gradient: | 10 | 0.00 |
|  | 90 | 2.70 |
|  | 90 | 3.00 |
|  | 10 | 3.30 |

Equipment
Instrument: Agilent Technology; HP 1100 Series, DAD
Detection: UV 190-400 nm
Detection: Agilent Technology; HP 1100 MSD
Ion source: ESI+
Method:
2Hb

| Column: | MERCK; Chromolith Flash; RP18e; 25 × 4.6 mm; column heated to 60° C. |
| --- | --- |
| Mobile phase: | A = Water + 0.1% HCOOH; B = Methanol |
| Flow rate: | 2.5 μL/min |

|  | % FM B | Minutes |
| --- | --- | --- |
| Gradient: | 10 | 0.00 |
|  | 100 | 1.61 |
|  | 100 | 2.25 |

Equipment
Instrument: Agilent Technology; HP 1200 Series, DAD
Detection: UV 190-400 nm
Detection: Agilent Technology; 1200 MSD
Ion source: ESI+
Method:
Z1 2

| Column: | Waters; XBridge C18, 3 × 30 mm, 2.5 μm, at 60° C. |
| --- | --- |
| Mobile: | A = water + 0.2% TFA; B = MeOH |
| Flow rate: | 2.2 ml/min |

|  | A % | B % | Time [min] |
| --- | --- | --- | --- |
| Gradient: | 95 | 5 | 0.00 |
|  | 95 | 5 | 0.05 |
|  | 0 | 100 | 1.40 |
|  | 0 | 100 | 1.80 |

Equipment:
Instrument: Agilent Technology; 1200 Series, DAD
Detection: UV 210-400 nm
Detection: Agilent Technology; 1200 MSD
Ion source: ESI+
Method:
Z1 5

| Column: | Waters; XBridge C18, 3 × 30 mm, 2.5 μm, at 60° C. |
| --- | --- |
| Mobile: | A = water + 0.1% TFA; B = MeOH |

|  | A % | B % | Time [min] | Flow rate [ml/min] |
| --- | --- | --- | --- | --- |
| Gradient: | 95 | 5 | 0.00 | 1.9 |
|  | 95 | 5 | 0.20 | 1.9 |
|  | 0 | 100 | 1.55 | 1.9 |
|  | 0 | 100 | 1.60 | 2.4 |
|  | 0 | 100 | 1.80 | 2.4 |

Equipment:
Instrument: Agilent Technology; 1200 Series, DAD
Detection: UV 210-400 nm
Detection: Agilent Technology; 1200 MSD
Ion source: ESI+
Method:
2Ja (isocratic)
Column: DAICEL Chiralpack AD-H 5 µm, 4.6×250 mm
Mobile phase: A=Hexane; B=Isopropanol
A/B=80/20%
Flow rate: 1 ml/min
Equipment
Instrument: LC Agilent Technologies. HPLC 1100 Serie, DAD Version A.
Detection: UV 220-300 nm
GC-MS Methods:
Method:
  3A
  Column: Agilent DB-5MS, 25 m×0.25 mm×0.25 µm
  Carrier gas: Helium, 1 ml/min costant flow
  Oven Program: 50° C. (hold 1 min.), to 100° C. in 10° C./min, to 200° C. in 20° C./min, to 300° C. in 30° C./min
  3B
  Column: Agilent DB-5MS, 25 m×0.25 mm×0.25 µm
  Carrier gas: Helium, 1 ml/min costant flow
  Oven Program: 80° C. to 110° C. in 10° C./min (hold 40 min), to 280° C. in 30° C./min
Equipment
Instrument: GC/MS Finnigan TRACE GC, TRACE MS quadrupole
Detection: TRACE MS quadrupole
Ion source: EI
Microwave Heating:
  Discover® CEM instruments, equipped with 10 and 35 mL vessels.

Synthesis of Intermediates

Intermediate 1

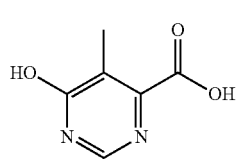

Potassium hydroxide (37.9 g, 0.67 mol) was suspended in 200 ml of dry ethanol, formamidine acetate (28.1 g, 0.27 mol) and diethyl oxalpropionate (50 ml, 0.27 mol) were added and the reaction mixture was stirred under reflux overnight. The reaction mixture was cooled to room temperature and the precipitate formed was filtered, washed with ethanol and diethyl ether, dissolved in 200 ml of water and the solution obtained acidified by a 37% aqueous solution of hydrochloric acid until pH=2. The acidic aqueous solution was concentrated under vacuum and the residue obtained was suspended and stirred in 100 ml of methanol. The insoluble inorganic salts were filtered off. The solution was concentrated. 15 g (97.4 mmol) of the desired compound were obtained.

Intermediate 1b

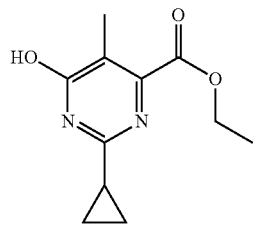 [SMILES: CCOC(=O)c1nc(C2CC2)nc(O)c1C]

Commercially available cyclopropancarboxyamidine (10 g, 83 mmol), diethyloxalpropionate (15.63 ml, 83 mmol) and potassium carbonate (26.6 g, 207 mmol) were suspended in 160 ml of ethanol and the reaction mixture was stirred under reflux for 4 h. The reaction mixture was filtered over a celite pad and the filtrate solution was evaporated. The crude product was purified by flash chromatography (BIOTAGE SP1; silica gel cartridge: SNAP 100 g; eluent: dichloromethane) to give the desired compound (4.6 g, 18.6 mmol).

Intermediate 1c

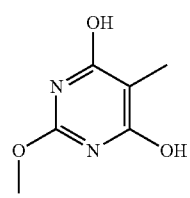

Diethylmethyl malonate (17 ml, 107 mmol) was added to sodium methoxide (30% in methanol, 101 ml, 547 mmol) and stirred for 15 min at 0° C. A solution of commercially available O-methylisourea hydrochloride (14.5 g, 131 mmol) in 20 ml MeOH was added dropwise to the reaction mixture. The reaction mixture was stirred for 1 h at 0° C. Then, the reaction was heated for 2 h at 65° C. The solvent was removed under vacuum. Water was added to the residue and heated for 10 min at 50° C. The mixture was acidified by addition of acetic acid until pH 4 and then cooled in an ice bath. The formed precipitate was filtered and washed with ice water to give the desired product (13.8 g).

Intermediate 2

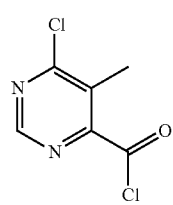

Intermediate 1 (7.0 g, 45.4 mmol) was suspended in 35 ml of thionyl chloride (0.45 mol), 0.10 ml of DMF was added and the reaction mixture was refluxed for 1 h. The reaction mixture was concentrated in vacuum. 8.6 g (45 mmol) of the desired product were obtained and used in the next steps without further purification.

Intermediate 2b

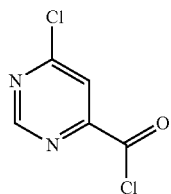

was synthesized in analogy to intermediate 2 starting from 6-hydroxypyrimidine-4-carboxylic acid.

Intermediate 2c

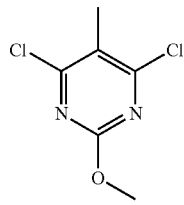

Intermediate 1c (1.9 g, 12.2 mmol) was added to phosphoryl chloride (17 ml) and the reaction mixture was stirred overnight at 60° C. The reaction mixture was cooled to 0° C. and quenched with 4 N NaOH. Then, the crude mixture was extracted with dichloromethane. The combined organic layers were concentrated under vacuum. The residue was purified by reversed phase HPLC to give the desired product.

Intermediate 3

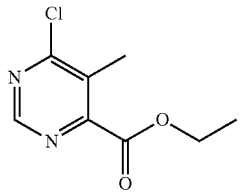

Potassium carbonate (43.34 g, 0.31 mol) was suspended in 350 ml of dry ethanol. A solution of intermediate 2 (20 g, 0.10 mol) in 10 ml of dichloromethane was added slowly at 0° C. The reaction mixture was allowed to reach room temperature and stirred for 1 h. Potassium carbonate was filtered off and the solvent was removed under vacuum. The crude product was purified by flash chromathography (BIOTAGE SP1; silica gel cartridge: 65i; eluent: dichloromethane/ethyl acetate=95/5%). 5.3 g (26 mmol) of the desired compound were obtained.

Intermediate 3

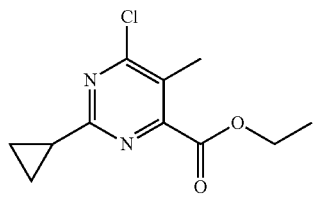 [SMILES: CCOC(=O)c1nc(C2CC2)nc(Cl)c1C]

Intermediate 1b (4.6 g, 18.6 mmol) and phosphorus oxychloride (16.8 ml, 180 mmol) was refluxed at 130° C. for 18 h. The reaction mixture was concentrated under vacuum, the crude product was diluted with toluene and the organic phase was concentrated under vacuum. The residue was diluted with 100 ml of ethyl acetate and the organic phase was washed with 100 ml of a cooled aqueous saturated sodium carbonate solution. The organic phase was concentrated under vacuum to yield the desired product (4.1 g) which was used in the next step without further purification.

Intermediate 3b

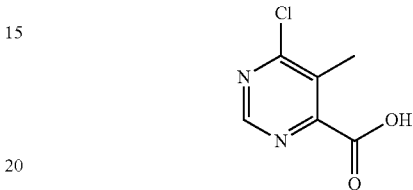

Intermediate 3 (1 g, 5 mmol) was diluted in 5 ml of tetrahydrofurane and 5 ml of water, lithium hydroxide (313 mg, 7.5 mmol) was added and the reaction mixture was stirred at room temperature for 1 h. The reaction mixture was concentrated under vacuum The residue was dissolved in 10 ml of a 4 M solution of hydrochloric acid in 1,4-dioxane, the solution was stirred at room temperature for 10 minutes and then concentrated under vacuum. The crude product was dissolved in dichlorometane and filtered. The filtrate was concentrated under vacuum giving the desired product (880 mg, 5.1 mmol).

Intermediate 3c

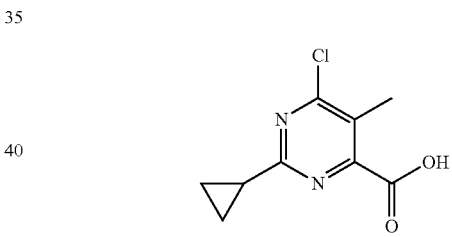

was prepared in analogy to Intermediate 3b starting from Intermediate 3a.

Intermediate 3d

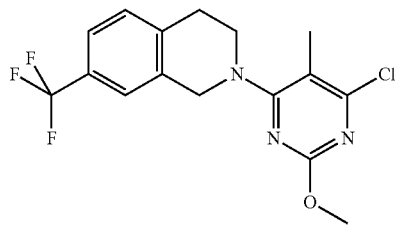 [SMILES: COc1nc(Cl)c(C)c(N2CCc3ccc(C(F)(F)F)cc3C2)n1]

Intermediate 2c (200 mg, 0.98 mmol) and commercially available 7-trifluoromethyl-1,2,3,4-tetrahydro-isoquinoline hydrochloride (234 mg, 0.98 mmol) were dissolved in 2 ml N-methyl-2-pyrrolidine. N,N-diisopropylethylamine (0.45 ml, 2.5 mmol) was added and the reaction mixture was stirred at 120° C. for 1 h. The mixture was filtered and purified by reversed phase HPLC to give the desired product (300 mg, 0.84 mmol).

Intermediate 4a

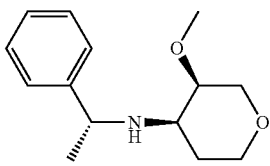 [SMILES: CO[C@H]1COCC[C@H]1N[C@H](C)c1ccccc1]

3-Methoxy-tetrahydro-pyran-4-one* (1 g, 7.68 mmol), commercially available (R)-(+)-1-phenylethylamine (0.99 ml, 7.68 mmol) and Raney-Nickel (200 mg) in 10 ml of dry ethanol were stirred under a hydrogen atmosphere (5 bar) for 15 days. The reaction mixture was diluted with 20 ml of methanol and 20 ml of tetrahydrofurane, stirred for 15 minutes, filtered on a celite pad and concentrated under vacuum. The crude product was loaded on a SCX cartridge (50 g). The cartridge was washed with methanol and the desired product was eluted with a 7 M solution of ammonia in methanol. The basic organic phase was concentrated under vacuum and the crude product was purified by flash chromatography (dichloromethane/methanol=98/2%) to obtain 710 mg (3.02 mmol) of the desired product as single stereoisomer (diastereoisomeric purity confirmed and relative cis stereochemistry assigned by NMR).

GC/MS (method 3B) $R_t$=35.04 min

* Tetrahedron Letters, 2005, 447-450

Intermediate 4b

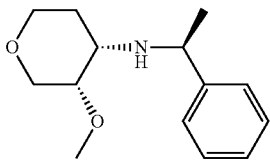 [SMILES: CO[C@@H]1COCC[C@@H]1N[C@@H](C)c1ccccc1]

was synthesised in analogy to Intermediate 4a, starting from 3-Methoxy-tetrahydro-pyran-4-one and commercially available (S)-(−)-1-phenylethylamine (diastereoisomeric purity confirmed and relative cis configuration assigned by NMR).

GC/MS (method 3B) $R_t$=35.04 min

Intermediate 5a

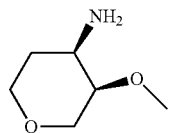

Intermediate 4a (1.18 g, 5.01 mmol), Pd/C 10% (200 mg) and acetic acid (0.3 ml, 5.01 mmol) in 20 ml of methanol were stirred under a hydrogen atmosphere (5 bar) for 18 h. The reaction mixture was diluted with 20 ml of methanol, stirred for 15 minutes, filtered on a celite pad and concentrated under vacuum. The crude product was loaded on a SCX cartridge (50 g). The cartridge was washed with methanol and the desired product was eluted with a 7 M solution of ammonia in methanol. The basic organic phase was concentrated under vacuum and 513 mg (3.91 mmol) of the desired product were obtained as single stereoisomer Intermediate 5b

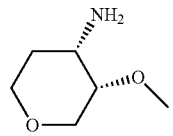

was synthesised in analogy to Intermediate 5a, starting from Intermediate 4b.

Intermediate 5c

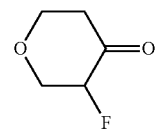

Commercially available 5,6-dihydro-4-methoxy-2H-pyran (5 g, 43.8 mmol) was dissolved in 70 ml acetonitrile and 70 ml water. Commercially available Selectfluor™-fluorinating reagent (17 g, 48.2 mmol) was added and the reaction mixture was stirred at room temperature for 2 h. NaCl (2 g) was added and the reaction mixture was extracted with diethyl ether. The organic phase was dried over sodium sulfate and concentrated under vacuum to give the desired product (4 g). The crude product was used in the next step without purification.

Intermediate 6a

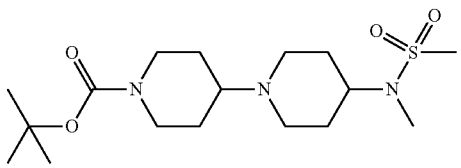 [SMILES: CN(C1CCN(C2CCN(C(=O)OC(C)(C)C)CC2)CC1)S(C)(=O)=O]

N-methyl-N-piperidin-4-yl-methanesulfonamide hydrochloride (11 g, 47.91 mmol; WO2009/47161) was suspended in 200 ml of 1,2-dichloroethane, N,N-diisopropylethylamine (17.12 ml, 96.17 mmol) and commercially available 1-(tert-butoxycarbonyl)-piperidin-4-one (9.58 g, 48.08 mmol) were added and the reaction mixture was stirred at room temperature for 30 min. Sodium triacetoxyborohydride (12.23 g, 57.50 mmol) was added and the reaction mixture was stirred at room temperature for 72 h. The reaction mixture was diluted with dichloromethane and washed with an aqueous saturated sodium bicarbonate solution. The organic phase was dried over sodium sulfate and concentrated under vacuum. The crude product was purified by flash chromatography (Biotage SP1; silica gel cartridge: 65i; eluent: ethyl acetate/methanol=50/50%) to obtain 7.2 g (19.2 mmol) of the desired compound.

Intermediate 7a

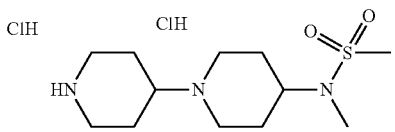 [SMILES: Cl ; CN(C1CCN(C2CCNCC2)CC1)S(C)(=O)=O ; Cl]

Intermediate 6a (7.2 g, 19.2 mmol) was suspended in 20 ml of 1,4-dioxane, a 4M solution of hydrochloric acid (48 ml, 192 mmol) in 1,4-dioxane was added dropwise. The reaction mixture was stirred at room temperature overnight. The reaction mixture was concentrated under vacuum. 6.3 g (18 mmol) of the desired compound were obtained.

The following intermediates were synthesized in analogy to Intermediates 6a and 7a.

| Starting ketone | Starting amine | Carbamate Intermediate | STRUCTURE | Diamino Intermediate | STRUCTURE |
|---|---|---|---|---|---|
| 3-Methoxy-tetrahydro-pyran-4-one (commercially available) | 4-amino-piperidine-1-carboxylic acid tert-butyl-ester (commercially available) | 6b | 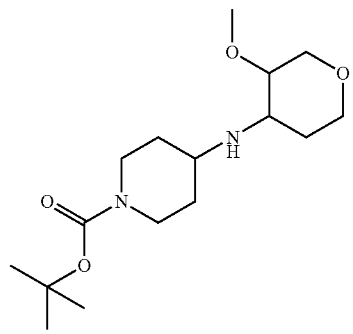 [SMILES: COC1COCCC1NC1CCN(C(=O)OC(C)(C)C)CC1] | 7b | 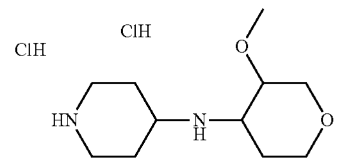 |
| 1-(tert-butoxy-carbonyl)-4-oxopiperidine (commercially available) | 5a | 6c | | 7c | |
| 1-(tert-butoxy-carbonyl)-4-oxopiperidine (commercially available) | 5b | 6d | | 7d | |
| 5c | 4-amino-piperidine-1-carboxylic acid tert-butyl-ester (commercially available) | 6e | 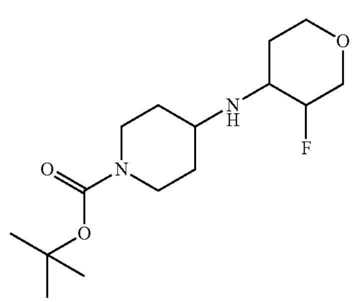 [SMILES: CC(C)(C)OC(=O)N1CCC(NC2CCOCC2F)CC1] | 7e | 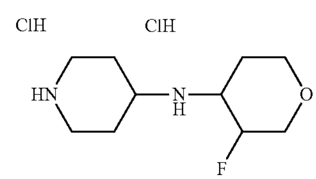 [SMILES: Cl ; Cl ; FC1COCCC1NC1CCNCC1] |

| Starting ketone | Starting amine | Carbamate Intermediate | STRUCTURE | Diamino Intermediate | STRUCTURE |
|---|---|---|---|---|---|
| | protocol see below | 6f | | 7f | ClH ClH |
| | protocol see below | 6g | | 7g | ClH ClH |
| Tetrahydro-pyran-4-one (commercially available) | 4-amino-piperidine-1-carboxylic acid tert-butyl-ester (commercially available) | 6h | 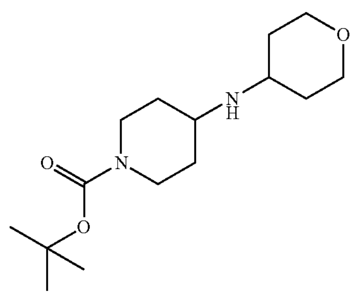 [SMILES: CC(C)(C)OC(=O)N1CCC(NC2CCOCC2)CC1] | 7h | ClH ClH |

Intermediate 6f

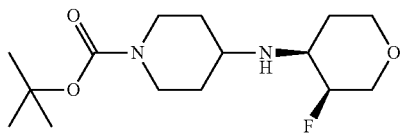 [SMILES: CC(C)(C)OC(=O)N1CCC(N[C@H]2CCOC[C@H]2F)CC1]

Preparative Chiral HPLC Separation of Intermediate 6e (360 mg, 1.19 mmol) gave 163 mg (0.54 mmol) of the isomerically pure cis-intermediate (first eluted cis-enantiomer, relative stereochemistry assigned by NMR).

Chiral HPLC (method 2Ja isocratic): $R_t$=5.197 min

Intermediate 6g

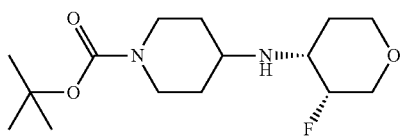 [SMILES: CC(C)(C)OC(=O)N1CCC(N[C@@H]2CCOC[C@@H]2F)CC1]

Further elution of the column gave 164 mg (0.54 mmol) of the second eluted cis-enantiomer (relative stereochemistry assigned by NMR).

Chiral HPLC (method 2Ja isocratic): $R_t$=6.012 min

Intermediate 8

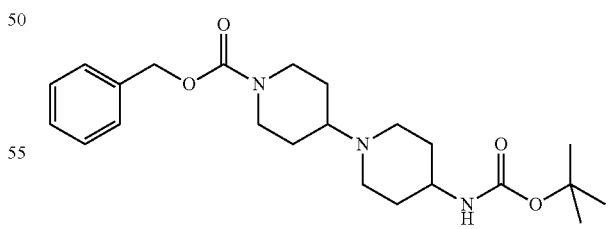

Commercially available piperidin-4-yl-carbamic acid tert-butyl ester (6 g, 30 mmol) and commercially available 1-(benzyloxycarbonyl)-4-oxopiperidine (9.6 g, 48 mmol) were dissolved in 50 ml of dichloromethane and the reaction mixture was stirred at room temperature for 30 min; sodium triacetoxyborohydride (12.23 g, 57.5 mmol) was added and the reaction mixture was stirred at room temperature overnight. The reaction mixture was diluted with dichloromethane and washed with an aqueous saturated sodium bicarbonate solution. The organic phase was dried over sodium sulfate and concentrated under vacuum. The crude product was treated with acetone/isopropyl ether and the precipitate obtained was filtered off. 8.4 g (20 mmol) of the desired product were obtained.

Intermediate 9

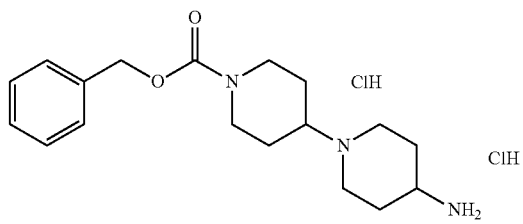 [SMILES: NC1CCN(C2CCN(C(=O)OCc3ccccc3)CC2)CC1 ; Cl ; Cl]

A solution of intermediate 8 (8.4 g, 20 mmol) in 150 ml of 1,4-dioxane was cooled to 0° C. Then, 12.6 ml (50 mmol) of a 4M solution of hydrochloric acid in 1,4-dioxane were added dropwise; the reaction mixture was allowed to warm to room temperature and stirred overnight. The precipitate was filtered off and dried at 50° C. under vacuum to give the desired product (6 g, 15 mmol).

Intermediate 10

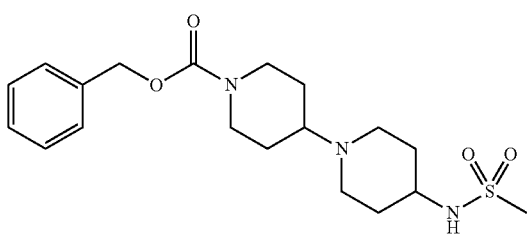 [SMILES: CS(=O)(=O)NC1CCN(C2CCN(C(=O)OCc3ccccc3)CC2)CC1]

Intermediate 9 (6.0 g, 15 mmol) was suspended in 55 ml of dichloromethane; triethylamine (6.43 ml, 46 mmol) was added and the reaction mixture was cooled to 0° C. and stirred for 30 min. Methanesulfonyl chloride (1.43 ml, 18 mmol) in 5 ml of dichloromethane was added dropwise. The reaction mixture was stirred at 0° C. for 1 h; then water was added and the reaction mixture was extracted with dichloromethane. The organic phase was washed with an aqueous saturated sodium bicarbonate solution, with brine, dried over sodium sulfate and concentrated under vacuum. The crude product was treated with diisopropyl ether, the precipitate was filtered off and dried. 5 g (13 mmol) of the desired product were obtained.

Intermediate 11

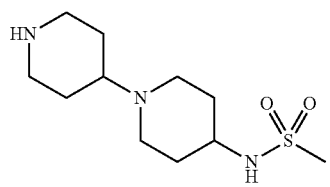 [SMILES: CS(=O)(=O)NC1CCN(C2CCNCC2)CC1]

Intermediate 10 (5 g, 13 mmol) was dissolved in 50 ml of methanol; acetic acid (1.5 ml, 25.3 mmol) and Pd/C 10% (500 mg) were added in sequence and the reaction mixture was stirred under a hydrogen atmosphere (3 bar) at room temperature for 5 days. The reaction mixture was filtered on a celite pad and the organic phase was loaded on a SCX cartridge (10 g). After washing with methanol, the desired compound was eluted with a 2M solution of ammonia in methanol. 3.7 g were obtained as a crude product.

Intermediate 12a

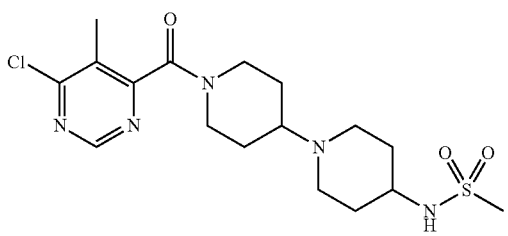 [SMILES: Cc1c(Cl)ncnc1C(=O)N1CCC(N2CCC(NS(C)(=O)=O)CC2)CC1]

The crude intermediate 11 (1.1 g) was suspended in 20 ml of dry dichloromethane, N,N-diisopropylethylamine (1.47 ml, 8.42 mmol) and DMF (137 μl, 1.67 mmol) were added and the reaction mixture was stirred under nitrogen atmosphere and cooled to 0° C. Intermediate 2 (812 mg, 4.21 mmol) in 5 ml of dichloromethane was added dropwise and the reaction mixture was allowed to warm to room temperature and stirred for 1.5 h; the reaction mixture was diluted with dichloromethane and washed with an aqueous saturated sodium bicarbonate solution. The organic phase was separated, dried over sodium sulfate and concentrated under vacuum. The crude product was purified by flash chromatography (isolute silica gel cartridge: 10 g; eluent: dichloromethane/methanol=95/5%). 1.0 g (2.41 mmol) of the desired compound were obtained.

The following intermediates were synthesized in analogy to Intermediate 12a.

| Piperidine Intermediate | Chloro-pyrimidine Intermediate | Core Intermediate | STRUCTURE |
|---|---|---|---|
| 7a | 2 | 12b | 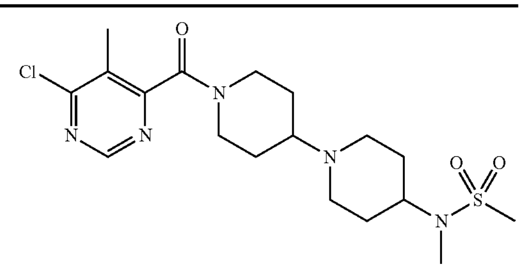 |

| Piperidine Intermediate | Chloro-pyrimidine Intermediate | Core Intermediate | STRUCTURE |
|---|---|---|---|
| 7b | 2 | 12c | 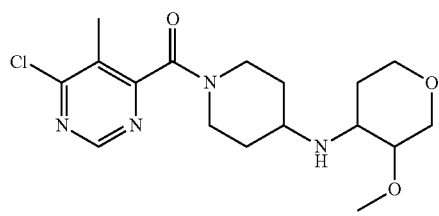 [SMILES: COC1COCCC1NC1CCN(C(=O)c2ncnc(Cl)c2C)CC1] |
| 7d | 2b | 12d | 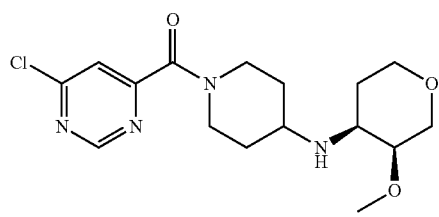 [SMILES: CO[C@@H]1COCC[C@@H]1NC1CCN(C(=O)c2cc(Cl)ncn2)CC1] |
| 7d | 2 | 12e | 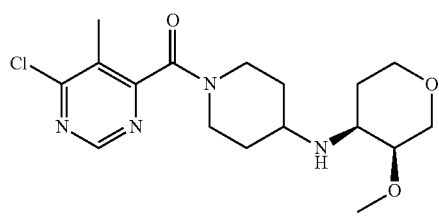 [SMILES: CO[C@@H]1COCC[C@@H]1NC1CCN(C(=O)c2ncnc(Cl)c2C)CC1] |

Intermediate 13a

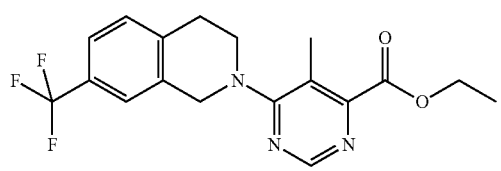 [SMILES: CCOC(=O)c1ncnc(N2CCc3ccc(C(F)(F)F)cc3C2)c1C]

Intermediate 3 (590 mg, 2.95 mmol) and N,N-diisopropylethylamine (0.63 ml, 3.68 mmol) were dissolved in 10 ml of dry 1,4-dioxane; commercially available 7-trifluoromethyl-1,2,3,4-tetrahydro-isoquinoline hydrochloride (350 mg, 1.47 mmol) was added and the reaction mixture was refluxed for 18 h. The reaction mixture was cooled to room temperature, water was added and the reaction mixture was extracted with dichloromethane; the organic phase was washed with an aqueous saturated sodium bicarbonate solution and concentrated under vacuum. 480 mg of the desired compound were obtained as crude product.

Intermediate 13af

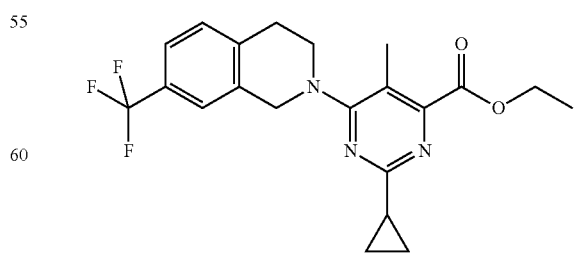

Was synthesised in analogy to Intermediate 13a starting from Intermediate 3c.

Intermediate 13ab

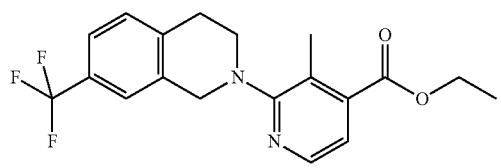

Commercially available 2-chloro-3-methylpyridine-4-carboxylic acid ethyl ester (300 mg, 1.5 mmol), commercially available 7-trifluoromethyl-1,2,3,4-tetrahydro-isoquinoline (357 mg, 1.5 mmol), palladium acetate (33 mg, 0.15 mmol), commercially available 2,2'-bis(diphenylphosphino)-1,1'-binaphthyl (467 mg, 0.75 mmol) and sodium tert-butoxide (202 mg, 2.10 mmol) were suspended in 20 ml of 1,2-dimethoxyethane and the reaction mixture was refluxed under nitrogen atmosphere for 12 h. The reaction mixture was diluted with dichloromethane and washed with an aqueous saturated sodium bicarbonate solution. The organic phase was separated, dried over sodium sulfate and concentrated under vacuum. The crude product was purified by flash chromatography (isolute silica gel cartridge: 10 g; eluent: dichloromethane/methanol=95/5%). 300 mg of a product were obtained and used in the following reaction without any purification.

Intermediate 14a

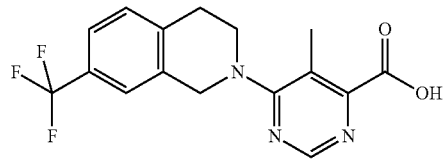 [SMILES: Cc1c(C(=O)O)ncnc1N1CCc2ccc(C(F)(F)F)cc2C1]

The crude intermediate 13a (480 mg) was dissolved in 5 ml of tetrahydrofurane and a solution of LiOH (193 mg, 4.60 mmol) in 5 ml of water was added. The reaction mixture was stirred at room temperature for 2 h and then concentrated under vacuum. 20 ml of water was added and the reaction mixture was acidified with 5 ml of a 4M solution of hydrochloric acid in water. The aqueous phase was extracted with dichloromethane (2×20 ml). The organic phase was dried over sodium sulfate and concentrated under vacuum. 320 mg (0.95 mmol) of the desired product were obtained.

Intermediate 14af

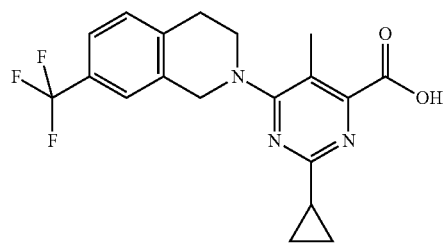 [SMILES: Cc1c(C(=O)O)nc(C2CC2)nc1N1CCc2ccc(C(F)(F)F)cc2C1]

Was synthesised in analogy to Intermediate 14a starting from Intermediate 13af.

The following intermediates were synthesized in analogy to intermediate 13a and 14a starting from the proper 1,2,3,4-tetrahydro-isoquinoline hydrochlorides:

| Starting amine (commercially available) | Ester intermediate | STRUCTURE | Acid intermediate | STRUCTURE |
|---|---|---|---|---|
| ![amine 13b] | 13b | ![ester 13b] | 14b | ![acid 14b] |
| ![amine 13c] | 13c | ![ester 13c] | 14c | ![acid 14c] |

-continued

| Starting amine (commercially available) | Ester intermediate | STRUCTURE | Acid intermediate | STRUCTURE |
|---|---|---|---|---|
| 7-methyl-1,2,3,4-tetrahydroisoquinoline | 13aa | ethyl 6-(7-methyl-3,4-dihydroisoquinolin-2(1H)-yl)-5-methylpyrimidine-4-carboxylate | 14aa | 6-(7-methyl-3,4-dihydroisoquinolin-2(1H)-yl)-5-methylpyrimidine-4-carboxylic acid |
| — | 13ab (see specific protocol) | ethyl 2-(7-(trifluoromethyl)-3,4-dihydroisoquinolin-2(1H)-yl)-3-methylpyridine-4-carboxylate | 14ab | 2-(7-(trifluoromethyl)-3,4-dihydroisoquinolin-2(1H)-yl)-3-methylpyridine-4-carboxylic acid |
| 7-fluoro-1,2,3,4-tetrahydroisoquinoline | 13ac | ethyl 6-(7-fluoro-3,4-dihydroisoquinolin-2(1H)-yl)-5-methylpyrimidine-4-carboxylate | 14ac | 6-(7-fluoro-3,4-dihydroisoquinolin-2(1H)-yl)-5-methylpyrimidine-4-carboxylic acid |
| — | 13ad (see specific protocol) | ethyl 6-(7-(trifluoromethyl)-3,4-dihydroisoquinolin-2(1H)-yl)-5-methyl-2-methoxypyrimidine-4-carboxylate | 14ad | 6-(7-(trifluoromethyl)-3,4-dihydroisoquinolin-2(1H)-yl)-5-methyl-2-methoxypyrimidine-4-carboxylic acid |
| 7-bromo-1,2,3,4-tetrahydroisoquinoline | 13ae | ethyl 6-(7-bromo-3,4-dihydroisoquinolin-2(1H)-yl)-5-methylpyrimidine-4-carboxylate | 14ae | 6-(7-bromo-3,4-dihydroisoquinolin-2(1H)-yl)-5-methylpyrimidine-4-carboxylic acid |

-continued

| Starting amine (commercially available) | Ester intermediate | STRUCTURE | Acid intermediate | STRUCTURE |
|---|---|---|---|---|
| 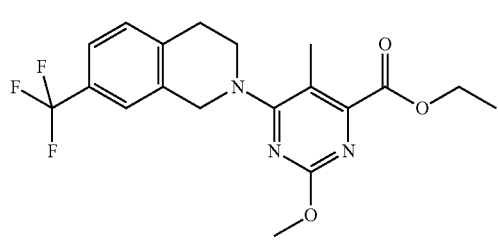 [SMILES: CCOC(=O)c1nc(OC)nc(N2CCc3ccc(C(F)(F)F)cc3C2)c1C] | 13ag | | 14ag | 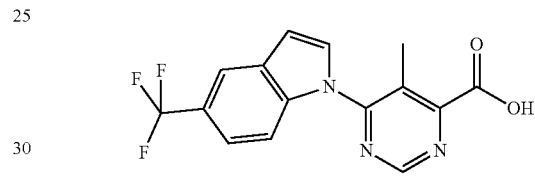 |

Intermediate 13ad

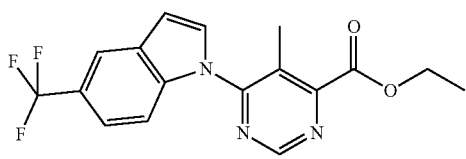 [SMILES: CCOC(=O)c1ncnc(-n2ccc3cc(C(F)(F)F)ccc32)c1C]

A mixture of intermediate 3d (290 mg, 0.81 mmol), palladium acetate (18 mg, 0.08 mmol), commercially available 1,1'-bis(diphenylphosphino)-ferrocene (45 mg, 0.08 mmol) and sodium acetate (199 mg, 2.4 mmol) in 8.5 ml methanol and 8.5 ml DMF was stirred under a carbon monoxide atmosphere (5 bar) for 18 h at 70° C. The reaction mixture was filtered and concentrated in vacuum. The residue was purified by reversed phase HPLC to give the corresponding ester (300 mg, 0.79 mmol).

Intermediate 13d

A mixture of intermediate 3 (161 mg, 802 µmol), commercially available 5-trifluoromethyl-indole (148 mg, 802 µmol) and potassium carbonate (222 mg, 1.6 mmol) in 2 ml DMF was stirred over night at 70° C. The reaction mixture was diluted with a saturated aqueous sodium bicarbonate solution and extracted with ethyl acetate (3×). The combined organic layers were washed with brine, dried over sodium sulfate and concentrated in vacuum. The residue was purified by reversed phase HPLC to give the desired product (128 mg, 276 µmol).

Intermediate 14d

1 M Sodium hydroxide (717 µl, 717 µmol) was added to a solution of intermediate 13d (166 mg, 358 µmol) in 5 ml methanol. The reaction mixture was stirred for 1 h. The mixture was acidified with trifluoroacetic acid and directly purified by reversed phase HPLC to give the desired product (122 mg, 280 µmol).

Intermediate 15

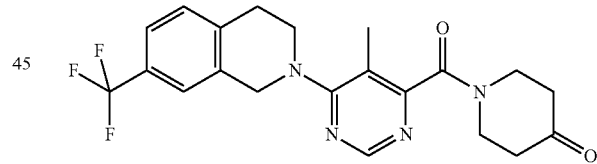

Intermediate 14a (220 mg, 0.65 mmol), TBTU (209 mg, 0.65 mmol) and N,N-diisopropylethylamine (0.34 ml, 1.96 mmol) were dissolved in 8 ml of DMF. The reaction mixture was stirred under nitrogen atmosphere at room temperature for 30 min; then piperidin-4-one hydrochloride (88 g, 0.65 mmol) was added and the reaction mixture was stirred at room temperature overnight. The reaction mixture was concentrated under vacuum and the crude product was dissolved in dichloromethane. The organic phase was washed with a saturated aqueous solution of sodium bicarbonate, with a 1M aqueous solution of sodium hydroxide, with brine, then dried over sodium sulfate, filtered and concentrated under vacuum. The crude product was purified by flash chromatography (Isolute silica gel cartridge: 10 g eluent: dichloromethane/methanol=95/5%). 250 mg (0.65 mmol) of the desired compound were obtained.

Intermediate 16a

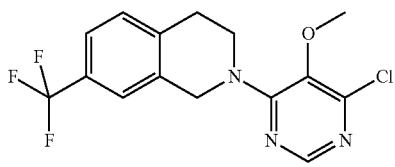 [SMILES: COc1c(Cl)ncnc1N1CCc2ccc(C(F)(F)F)cc2C1]

N,N-diisopropylethylamine (486 µl, 2.6 mmol) was added to a mixture of commercially available 7-trifluoromethyl-1,2,3,4-tetrahydroisoquinoline hydrochloride (250 mg, 1.1 mmol) and commercially available 4,6-dichloro-5-methoxy-pyrimidine (188 mg, 1.1 mmol) in 2 ml NMP. The reaction mixture was heated in the microwave at 120° C. for 30 min. Then, dichloromethane was added and the mixture was washed with water (2×). The organic layer was dried over sodium sulfate and concentrated in vacuum. The residue was purified by reversed phase HPLC to give the desired product (231 mg, 672 µmol).

Intermediate 17a

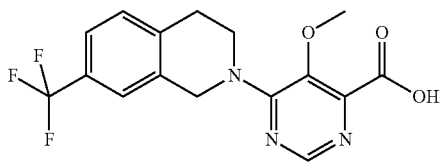 [SMILES: COc1c(C(=O)O)ncnc1N1CCc2ccc(C(F)(F)F)cc2C1]

A mixture of intermediate 16a (231 mg, 672 µmol), palladium acetate (15 mg, 67 µmol), commercially available 1,1'-bis(diphenylphosphino)-ferrocene (37 mg, 67 µmol), sodium acetate (165 mg, 2.0 mmol) in 10 ml methanol and 10 ml DMF was stirred under a carbon monoxide atmosphere (5 bar) for 23 h at 70° C. The mixture was filtered and concentrated in vacuum. The residue was purified by reversed phase HPLC to give the corresponding ester (177 mg, 482 µmol).

A 1 M aqueous solution of sodium hydroxide was added to a solution of the ester (177 mg, 482 µmol) in 5 ml methanol. The reaction mixture was stirred for 3 h at room temperature. The reaction mixture was concentrated, acidified with 1 M hydrochloric acid and extracted with diethyl ether (3×) and n-butanol (1×). The combined organic layers were dried over sodium sulfate and concentrated in vacuum to give the crude product (216 mg, 482 µmmol).

The following intermediates were synthesized in analogy to intermediate 16a and 17a starting from 4,6-dichloro-5-methoxypyrimidine:

| Starting amine | Cl-pyrimidine intermediate | STRUCTURE | Acid intermediate | STRUCTURE |
|---|---|---|---|---|
| 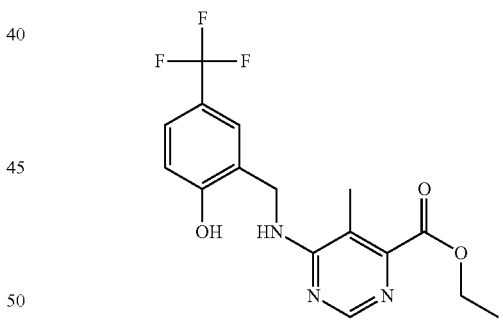 | 16b | | 17b | |

Intermediate 18

Intermediate 3 (400 mg, 1.99 mmol), commercially available 2-tert-butoxy-5-trifluoromethyl-benzylamine (492 mg, 1.99 mmol) and N,N-diisopropylethylamine (0.51 ml, 2.99 mmol) was dissolved in 15 ml of 1,4-dioxane and the reaction mixture was refluxed for 12 h. The reaction mixture was diluted with dichloromethane and washed with an aqueous saturated sodium bicarbonate solution. The organic phase was separated, dried over sodium sulfate and concentrated under vacuum. The crude product was purified by flash chromatography (isolute silica gel cartridge: 10 g; eluent: dichloromethane/methanol=98/2%). The product (680 mg) was dissolved in 3 ml of 1,4-dioxane; 5 ml of a 4M solution of hydrichloric acid in 1,4 dioxane was added and the reaction mixture was stirred at room temperature for 72 h. The reaction mixture was diluted with dichloromethane and washed with an aqueous saturated sodium bicarbonate solution. The organic phase was separated, dried over sodium sulfate and concentrated under vacuum. The crude product was purified by flash chromatography (isolute silica gel cartridge: 10 g; eluent: dichloromethane/methanol=90/10%). 310 mg (0.87 mmol) of the desired product were obtained.

Intermediate 19

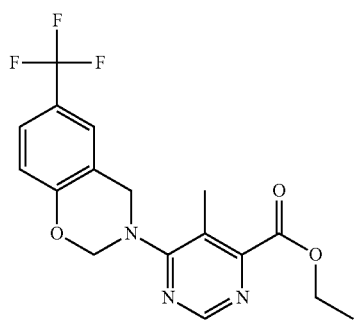 [SMILES: CCOC(=O)c1ncnc(N2COc3ccc(C(F)(F)F)cc3C2)c1C]

Intermediate 18 (310 mg, 0.87 mmol), parafolmaldehyde (10 ml) and p-toluensulfonic acid monohydrate (16.6 mg, 0.09 mmol) were dissolved in 10 ml of toluene. The reaction mixture was refluxed for 1 h, then additional 10 ml of paraformaldehyde were added. The reaction mixture was refluxed until gas evolution was finished. The reaction mixture was concentrated under vacuum and the crude product was purified by flash chromatography (isolute silica gel cartridge: 10 g; eluent: dichloromethane/ethyl acetate=80/20%). 50 mg (0.14 mmol) of the desired product were obtained.

Intermediate 20

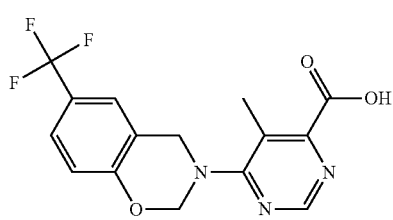 [SMILES: Cc1c(C(=O)O)ncnc1N1COc2ccc(C(F)(F)F)cc2C1]

Intermediate 20 was synthesized in analogy to the preparation of Intermediate 14a.

SYNTHESIS OF EXAMPLES

The examples of this invention are synthesized according to the following general synthetic procedures:

Synthetic Procedure A

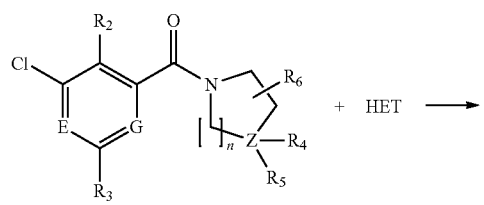

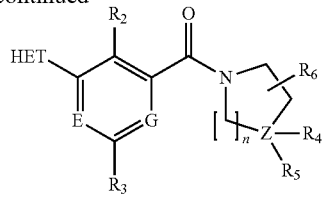

Examples: 1-62; 62a-62z, 62aa-62an

Synthetic Procedure B

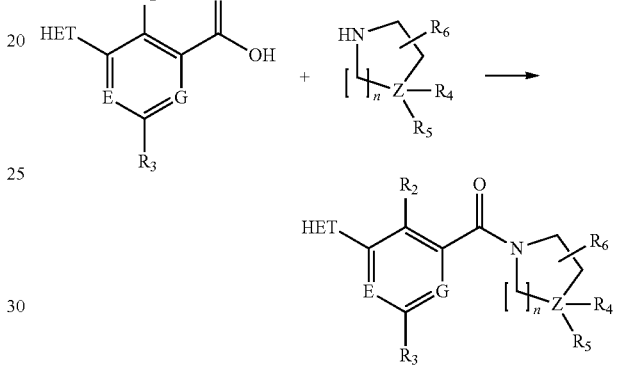

Examples: 63-82; 69a-69z, 69ab-69ac

Example 1

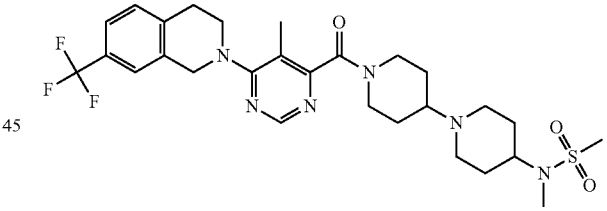

Intermediate 12b (100 mg, 0.19 mmol), commercially available 7-trifluoromethyl-1,2,3,4-tetrahydro-isoquinoline hydrochloride (66 mg, 0.28 mmol) and N,N-diisopropyl-ethyl amine (0.09 ml, 0.56 mmol) in 0.5 ml of dry 1,4-dioxane were mixed in a microwave vial and reacted in the following conditions: Power 100, Ramp 5 min, Hold 2 h, Temperature 150° C., Pressure 150 psi, Stirring. The reaction mixture was concentrated under vacuum and diluted with dichloromethane. The organic phase was washed with an aqueous saturated sodium bicarbonate solution, dried over sodium sulfate and concentrated under vacuum. The crude product was purified by reverse phase preparative HPLC. 21 mg (0.04 mmol) of the desired product were obtained.

HPLC (Method 1E Hydro): $R_t$. (min)=9.26

$[M+H]^+$=595

The following examples were synthesized in analogy to the preparation of Example 1

| Ex # | MOLSTRUCTURE | Intermediate | Amine (commercially available) | [M + H]⁺ | HPLC R_t (min) | Method |
|---|---|---|---|---|---|---|
| 2 | | 12c | 8-trifluoro-methyl-1,2,3,4-tetra-hydro-isoquinoline | 534 | 8.92 | 1 E Hydro |
| 3 | | 12b | 2-(4-Chloro-phenyl)-morpholine | 591 | 9.08 | 1 E Hydro |
| 4 | | 12c | 2-(4-Chloro-phenyl)-morpholine | 530 | 8.83 | 1 E Hydro |
| 5 | | 12c | 2-Phenyl-morpholine | 496 | 7.84 | 1 E Hydro |

-continued

| Ex # | MOLSTRUCTURE | Intermediate | Amine (commercially available) | [M + H]⁺ | HPLC R$_t$ (min) | Method |
|---|---|---|---|---|---|---|
| 6 | | 12b | 4-spiroindane-piperidine | 581 | 9.92 | 1 E Hydro |
| 7 | | 12c | 7-fluoro-1,2,3,4-tetrahydro-isoquinoline | 484 | 8.25 | 1 E Hydro |
| 8 | | 12c | 7-trifluoro-methoxy-1,2,3,4-tetra-hydro-isoquinoline | 550 | 9.44 | 1 E Hydro |
| 9 | | 12c | 3-(3-trifluoro-methyl-phenyl)-piperidine | 562 | 9.84 | 1 E Hydro |
| 10 | | 12c | 7-chloro-1,2,3,4-tetrahydro-isoquinoline | 500 | 8.94 | 1 E Hydro |

| Ex # | MOLSTRUCTURE | Intermediate | Amine (commercially available) | [M + H]⁺ | HPLC R$_t$ (min) | Method |
|---|---|---|---|---|---|---|
| 11 | | 12b | 4-spiroindene-piperidine | 579 | 9.58 | 1 E Hydro |
| 12 | | 12c | 3-(3-fluoro-phenyl)-piperidine | 512 | 9.14 | 1 E Hydro |
| 13 | | 12c | 4-(4-methyl-phenyl)-piperidine | 508 | 9.76 | 1 E Hydro |
| 14 | | 12c | 4-(4-methoxy-phenyl)-piperidine | 524 | 8.88 | 1 E Hydro |

-continued

| Ex # | MOLSTRUCTURE | Intermediate | Amine (commercially available) | [M + H]⁺ | HPLC R_t (min) | Method |
|---|---|---|---|---|---|---|
| 15 | | 12c | 4-(3-methyl-phenyl)-piperidine | 508 | 9.61 | 1 E Hydro |
| 16 | | 12c | 4-phenyl-piperidine | 494 | 9.04 | 1 E Hydro |
| 17 | | 12b | 4-(4-trifluoro-methyl-phenyl)-piperidine | 623 | 10.13 | 1 E Hydro |

-continued

| Ex # | MOLSTRUCTURE | Intermediate | Amine (commercially available) | [M + H]⁺ | HPLC R_t (min) | Method |
|---|---|---|---|---|---|---|
| 18 | | 12c | 4-(4-chloro-phenyl)-piperidine | 528 | 9.86 | 1 E Hydro |
| 19 | | 12c | 3H-spiro-isobenzofuran-1,4'-piperidine | 522 | 8.38 | 1 E Hydro |
| 20 | | 12b | 4-(3-trifluoro-methyl-phenyl)-piperidine | 623 | 10.04 | 1 E Hydro |
| 21 | | 12b | 4-(4-methoxy-phenyl)-piperidine | 585 | 9.16 | 1 E Hydro |

-continued

| Ex # | MOLSTRUCTURE | Intermediate | Amine (commercially available) | [M + H]+ | HPLC R_t (min) | Method |
|---|---|---|---|---|---|---|
| 22 | | 12b | 4-(3-fluoro-phenyl)-piperidine | 573 | 9.44 | 1 E Hydro |
| 23 | | 12c | 4-spiroindene-piperidine | 518 | 9.36 | 1 E Hydro |
| 24 | | 12b | 4-(4-methyl-phenyl)-piperidine | 569 | 10.03 | 1 E Hydro |

-continued
| Ex # | MOLSTRUCTURE | Intermediate | Amine (commercially available) | [M + H]+ | HPLC R$_t$ (min) | Method |
|---|---|---|---|---|---|---|
| 25 | 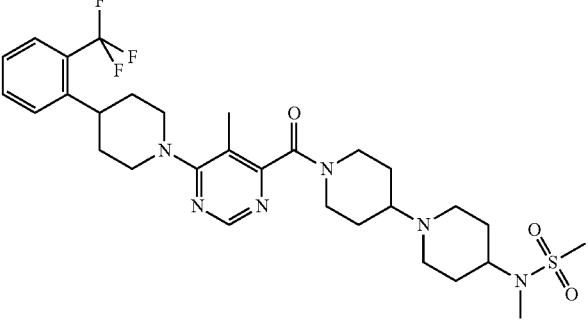 | 12b | 4-(2-trifluoro-methyl-phenyl)-piperidine | 623 | 10.06 | 1 E Hydro |
| 26 | 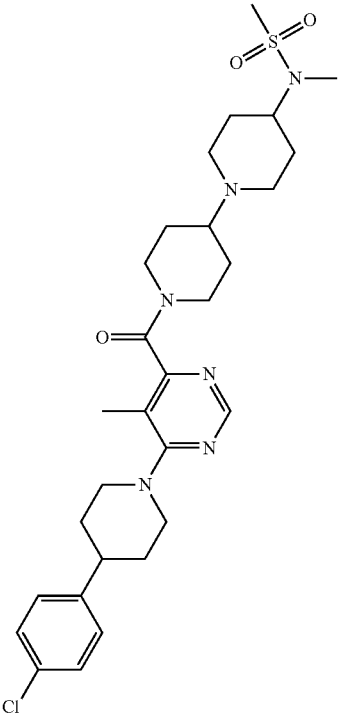 [SMILES: Cc1c(C(=O)N2CCC(N3CCC(N(C)S(C)(=O)=O)CC3)CC2)ncnc1N1CCC(c2ccc(Cl)cc2)CC1] | 12b | 4-(4-chloro-phenyl)-piperidine | 589 | 10.04 | 1 E Hydro |
| 27 | 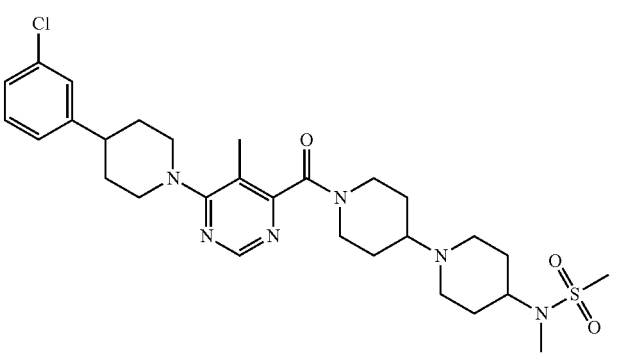 [SMILES: Cc1c(C(=O)N2CCC(N3CCC(N(C)S(C)(=O)=O)CC3)CC2)ncnc1N1CCC(c2cccc(Cl)c2)CC1] | 12b | 4-(3-chloro-phenyl)-piperidine | 589 | 9.94 | 1 E Hydro |

-continued

| Ex # | MOLSTRUCTURE | Intermediate | Amine (commercially available) | [M + H]+ | HPLC R$_t$ (min) | Method |
|---|---|---|---|---|---|---|
| 28 | | 12b | 4-phenyl-piperidine | 555 | 9.33 | 1 E Hydro |
| 29 | | 12c | 4-(2-trifluoro-methyl-phenyl)-piperidine | 562 | 9.88 | 1 E Hydro |
| 30 | | 12b | 4-(3-methyl-phenyl)-piperidine | 569 | 9.88 | 1 E Hydro |
| 31 | | 12c | 3-(3-chloro-phenyl)-piperidine | 528 | 7.23 | 2F |

-continued

| Ex # | MOLSTRUCTURE | Intermediate | Amine (commercially available) | [M + H]⁺ | HPLC R_t (min) | Method |
|---|---|---|---|---|---|---|
| 32 | | 12c | 3-(4-fluoro-phenyl)-piperidine | 512 | 6.91 | 2F |
| 33 | | 12c | 3-(4-methyl-phenyl)-piperidine | 508 | 7.11 | 2F |
| 34 | | 12b | 3-(4-trifluoro-methyl-phenyl)-piperidine | 623 | 7.63 | 2F |
| 35 | | 12b | 2-(3-chloro-phenyl)-piperidine | 589 | 7.34 | 2F |

-continued

| Ex # | MOLSTRUCTURE | Intermediate | Amine (commercially available) | [M + H]+ | HPLC R_t (min) | Method |
|---|---|---|---|---|---|---|
| 36 | | 12c | 3-(4-trifluoro-methyl-phenyl)-piperidine | 562 | 7.49 | 2F |
| 37 | | 12a | 7-trifluoro-methyl-1,2,3,4-tetrahydro-isoquinoline | 581 | 9.1 | 1 E Hydro |
| 38 | | 12c | 5-chloro-1,2,3,4-tetrahydro-isoquinoline | 500 | 9.16 | 1 E Hydro |
| 39 | | 12c | 5,7-dichloro-1,2,3,4-tetrahydro-isoquinoline | 534 | 10.22 | 1 E Hydro |

-continued

| Ex # | MOLSTRUCTURE | Intermediate | Amine (commercially available) | [M + H]⁺ | HPLC R_t (min) | Method |
|---|---|---|---|---|---|---|
| 40 | | 12c | 3-bromo-5,6,7,8-tetrahydro-[1,6]-naphthyridine | 545 | 6.06 | 2F |
| 41 | | 12c | 4-(4-trifluoro-methyl-phenyl)-piperidine | 562 | 7.67 | 2F |
| 42 | | 12c | 4-(3-trifluoro-methyl-phenyl)-piperidine | 562 | 7.67 | 2F |
| 43 | | 12c | 5-Trifluoro-methyl-2,3-dihydro-1H-isoindole | 520 | 9.02 | 1 E Hydro |

-continued

| Ex # | MOLSTRUCTURE | Intermediate | Amine (commercially available) | [M + H]+ | HPLC R_t (min) | Method |
|---|---|---|---|---|---|---|
| 44 | | 12b | 3-(2-fluoro-phenyl)-pyrrolidine | 559 | 6.27 | 2F |
| 45 | | 12b | 3-(4-trifluoro-methyl-phenyl)-pyrrolidine | 609 | 6.97 | 2F |
| 46 | | 12b | 3-(3-trifluoro-methyl-phenyl)-pyrrolidine | 609 | 6.9 | 2F |

-continued

| Ex # | MOLSTRUCTURE | Intermediate | Amine (commercially available) | [M + H]+ | HPLC R$_t$ (min) | Method |
|---|---|---|---|---|---|---|
| 47 | | 12b | 3-(4-chloro-phenyl)-pyrrolidine | 575 | 6.69 | 2F |
| 48 | | 12c | 3-(4-trifluoro-methyl-phenyl)-pyrrolidine | 548 | 6.76 | 1 E Hydro |
| 49 | | 12c | 3-(2-trifluoro-methyl-phenyl)-pyrrolidine | 548 | 6.86 | 2F |
| 50 | | 12c | 3-phenyl-pyrrolidine | 480 | 6.64 | 1 E Hydro |
| 51 | | 12c | 3-(2-fluoro-methyl-phenyl)-pyrrolidine | 498 | 8.71 | 1 E Hydro |
| 52 | | 12c | 3-(3-trifluoro-methyl-phenyl)-pyrrolidine | 548 | 6.71 | 2F |

-continued

| Ex # | MOLSTRUCTURE | Intermediate | Amine (commercially available) | [M + H]+ | HPLC R_t (min) | Method |
|---|---|---|---|---|---|---|
| 53 | | 12c | 3-(4-chloro phenyl)-pyrrolidine | 514 | 6.46 | 2F |
| 54 | | 12c | 2,3,4,5-tetra-hydro-1H-benzo[d]azepine | 480 | 8.55 | 1 E Hydro |
| 55 | | 12c | 1,2,3,4-tetra-hydro-isoquinoline-7-carbonitrile | 491 | 7.7 | 1 E Hydro |
| 56 | | 12c | 1-(5-trifluoro-methyl-pyridin-2-yl)-piperazine | 564 | 8.87 | 2F |
| 57 | | 12c | 1-(3-trifluoro-methyl-phenyl)-piperazine | 563 | 7.59 | 2F |

| Ex # | MOLSTRUCTURE | Intermediate | Amine (commercially available) | [M + H]+ | HPLC R$_t$ (min) | Method |
|---|---|---|---|---|---|---|
| 58 | | 12c | 2,3,4,5-tetrahydro-1H-benzo[c]azepine | 480 | 8.52 | 1 E Hydro |
| 59 | | 12c | 7-methyl-1,2,3,4-tetrahydro-isoquinoline | 480 | 9.22 | 1E f |
| 60 | | 12c | 7-trifluoromethyl-1,2,3,4-tetrahydro-isoquinoline | 533 | 3.37 | 2G |
| 61 | | 12c | 3-trifluoromethyl-5,6,7,8-tetrahydro-[1,6]-naphthyridine | 534 | 2.83 | 2G |
| 62 | | 12c | 4-spiroindane-piperidine | 519 | 3.48 | 2G |

| Ex # | MOLSTRUCTURE | Intermediate | Amine (commercially available) | [M + H]+ | HPLC R<sub>t</sub> (min) | Method |
|---|---|---|---|---|---|---|
| 62a | | 12d | 7-trifluoro-methyl-1,2,3,4-tetrahydro-isoquinoline | 520 | 1.76 | 2Ha |
| 62b | | 12c | 1-(3-trifluoro-methyl-phenyl)-3-azabi-cyclo[3.1.0]hexane | 560 | 9.73 | 1 E Hydro |
| 62c | | 12c | 1-(3,5-bis-tri-fluoromethyl-phenyl)-3-aza-bicyclo[3.1.0]hexane* | 628 | 10.57 | 1 E Hydro |
| 62d | | 12c | 1-o-tolyl-[1,4]diazepane | 523 | 6.65 | 2F |

-continued

| Ex # | MOLSTRUCTURE | Intermediate | Amine (commercially available) | [M + H]+ | HPLC R$_t$ (min) | Method |
|---|---|---|---|---|---|---|
| 62e | | 12c | 3-(2-chloro-phenyl)-pyrrolidine | 514 | 7.13 | 2F |
| 62f | | 12c | 2-aza-spiro[5.5]undecane | 486 | 7.32 | 2F |
| 62g | | 12c | 6-fluoro-spiro[chroman-2,4'-piperidine]-4-one | 568 | 7.13 | 2F |
| 62h | | 12c | spiro[chromene-2,4'-piperidin]-4(3H)-one | 550 | 6.89 | 2F |

-continued

| Ex # | MOLSTRUCTURE | Intermediate | Amine (commercially available) | [M + H]+ | HPLC R_t (min) | Method |
|---|---|---|---|---|---|---|
| 62i | | 12c | 6-bromo-spiro[chroman-2,4'-piperidine]-4-one | 627 | 1.45 | 2Ga |
| 62j | | 12c | 1-(4-chlorophenyl)-[1,4]diazepane | 542 | 1.42 | 2Ga |
| 62k | | 12c | 7-Isopropyl-1,2,3,4-tetrahydro-isoquinoline | 508 | 7.5 | 2F |
| 62l | | 12c | 2',3'-dihydro-1'H-spiro[cyclopropane-1,4'-isoquinoline] hydrochloride | 492 | 6.85 | 2f |
| 62m | | 12c | 1-o-Tolyl-piperazine | 509 | 9.53 | 1 E Hydro |

| Ex # | MOLSTRUCTURE | Intermediate | Amine (commercially available) | [M + H]+ | HPLC R$_t$ (min) | Method |
|---|---|---|---|---|---|---|
| 62n | | 12c | 4-Phenyl-azepane | 507 | 1.42 | 2Ga |
| 62o | | 12c | 1-(4-Bromo-phenyl)-3-aza-bicyclo[4.1.0]heptane** | 583 | 1.64 | 2Ga |
| 62p | | 12c | 1-(4-Trifluoro-methyl-phenyl)-piperazine | 563 | 1.48 | 2Ga |
| 62q | | 12c | 1-Benzo[1,3]dioxol-5-yl-piperazine | 539 | 7.77 | 1 E Hydro |

-continued

| Ex # | MOLSTRUCTURE | Intermediate | Amine (commercially available) | [M + H]+ | HPLC R$_t$ (min) | Method |
|---|---|---|---|---|---|---|
| 62r | | 12c | 5-Methyl-4-piperazin-1-yl-thieno[2,3-d]pyrimidine | 567 | 8.1 | 1 E Hydro |
| 62s | | 12c | 3-Phenyl-5,6,7,8-tetrahydro-imidazo[1,2-a]pyrazine | 532 | 8 | 1 E Hydro |
| 62t | | 12c | 1-(3,5-Dichloro-phenyl)-piperazine | 563 | 10.37 | 1 E Hydro |
| 62u | | 12c | 1-(3-Chloro-4-fluoro-phenyl)-piperazine | 547 | 9.37 | 1 E Hydro |
| 62w | | 12c | 1-(4-Chloro-3-trifluoromethyl-phenyl)-piperazine | 597 | 10.22 | 1 E Hydro |

-continued

| Ex # | MOLSTRUCTURE | Intermediate | Amine (commercially available) | [M + H]+ | HPLC R_t. (min) | Method |
|---|---|---|---|---|---|---|
| 62y | | 12c | 1-(4-Chloro-2-methyl-phenyl)-piperazine | 543 | 10.23 | 1 E Hydro |
| 62x | | 12c | 1-(2,3-Dichloro-phenyl)-piperazine | 563 | 10.15 | 1 E Hydro |
| 62z | | 12c | 1-(2-trifluoro-methyl-phenyl)-piperazine | 563 | 9.83 | 1 E Hydro |
| 62aa | | 12c | 1-(2-Chloro-phenyl)-piperazine | 529 | 9.18 | 1 E Hydro |

-continued

| Ex # | MOLSTRUCTURE | Intermediate | Amine (commercially available) | [M + H]+ | HPLC R$_t$ (min) | Method |
|---|---|---|---|---|---|---|
| 62ab | | 12c | 6-bromo-spiro[chroman-2,4'-piperidine] | 614 | 7.75 | 2F |
| 62ac | | 12c | 2-Trifluoro-methyl-5,6,7,8-tetrahydro-imidazo[1,2-a]pyrazine | 5.24 | 6.93 | 1 E Hydro |
| 62ad | | 12c | 1-(2,3-Dihydro-benzo[1,4]dioxin-6-yl)-piperazine | 553 | 7.88 | 1 E Hydro |

| Ex # | MOLSTRUCTURE | Intermediate | Amine (commercially available) | [M + H]+ | HPLC R$_t$ (min) | Method |
|---|---|---|---|---|---|---|
| 62ae | 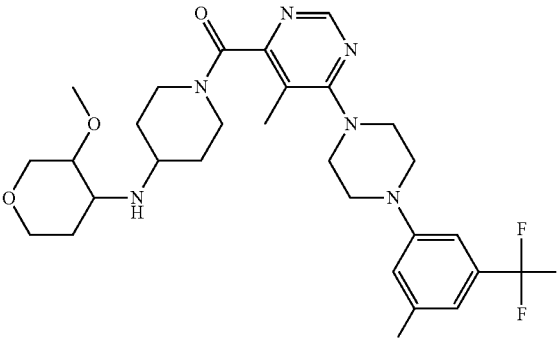 | 12c | 1-(3-Methoxy-5-trifluoro-methyl-phenyl)-piperazine | 593 | 9.75 | 1 E Hydro |
| 62af | 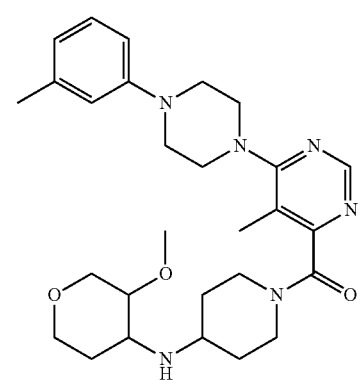 [SMILES: COC1COCCC1NC1CCN(C(=O)c2ncnc(N3CCN(c4cccc(C)c4)CC3)c2C)CC1] | 12c | 1-(3-Methyl-phenyl)-piperazine | 508 | 9 | 1 E Hydro |
| 62ag | 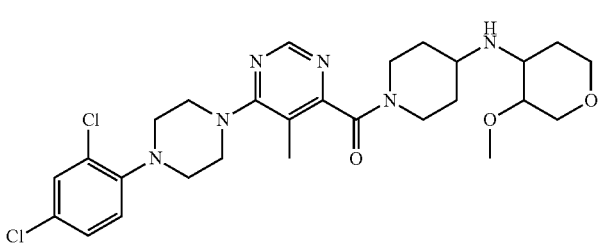 [SMILES: COC1COCCC1NC1CCN(C(=O)c2ncnc(N3CCN(c4ccc(Cl)cc4Cl)CC3)c2C)CC1] | 12c | 1-(2,4-Dichloro-phenyl)-piperazine | 563 | 10.18 | 1 E Hydro |
| 62ah | 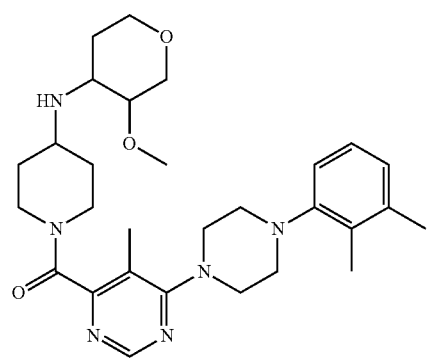 [SMILES: COC1COCCC1NC1CCN(C(=O)c2ncnc(N3CCN(c4cccc(C)c4C)CC3)c2C)CC1] | 12c | 1-(2,3-dimethyl-phenyl)-piperazine | 523 | 10.08 | 1 E Hydro |

-continued

| Ex # | MOLSTRUCTURE | Intermediate | Amine (commercially available) | [M + H]+ | HPLC R$_t$ (min) | Method |
|---|---|---|---|---|---|---|
| 62ai | | 12c | 1-(2,6-dimethyl-phenyl)-piperazine | 523 | 10.18 | 1 E Hydro |
| 62aj | | 12c | 1-(3,5-Dichloro-pyridin-4-yl)-piperazine | 564 | 8.58 | 1 E Hydro |
| 62ak | | 12c | 1-(3,5-Difluoro-phenyl)-piperazine | 531 | 9.12 | 1 E Hydro |
| 62al | | 12c | 1-(3,4-Dichloro-phenyl)-piperazine | 563 | 10.08 | 1 E Hydro |

| Ex # | MOLSTRUCTURE | Intermediate | Amine (commercially available) | [M + H]⁺ | HPLC R$_t$ (min) | Method |
|---|---|---|---|---|---|---|
| 62am | | 12c | 6-bromo-spiro[chroman-2,4'-piperidine] | 614 | 9.68 | 1 E Hydro |
| 62an | | 12c | 6-chloro-spiro[chroman-2,4'-piperidine] | 570 | 9.65 | 1 E Hydro |

(Ex 62c) *Synthesised in analogy as described in literature for the preparation of 1-(3-trifluoromethyl-phenyl)-3-azabicyclo[3.1.0]hexane (WO 2007113232).
(Ex 62o) **Synthesised in analogy as described in literature for the preparation of 3-azabicyclo[4.1.0]heptanes (WO 2008031771).

Example 63

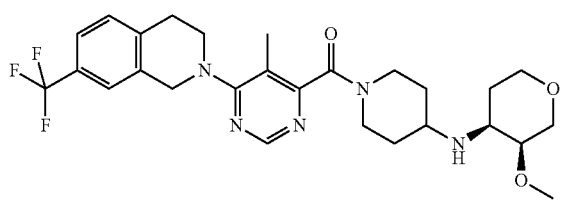 [SMILES: CO[C@@H]1COCC[C@@H]1NC1CCN(C(=O)c2ncnc(N3CCc4ccc(C(F)(F)F)cc4C3)c2C)CC1]

Intermediate 14a (135 mg, 0.40 mmol), TBTU (128 mg, 0.40 mmol) and N,N-diisopropyl-ethylamine (0.21 ml, 1.21 mmol) in 5 ml DMF were stirred at room temperature for 5 min. Intermediate 7d (114 mg, 0.40 mmol) was added and the reaction mixture was stirred at room temperature overnight. The reaction mixture was concentrated under vacuum and the crude product was dissolved in dichloromethane. The organic phase was washed with an aqueous saturated sodium bicarbonate solution, dried over sodium sulfate and concentrated under vacuum. The crude product was purified by flash chromatography (Si Isolute cartridge (20 g); eluent: dichloromethane/MeOH=95/5%). 105 mg (0.20 mmol) of the desired product were obtained.

HPLC (Method 1E Hydro): R$_t$ (min)=9.23

[M+H]⁺=534

The following examples were synthesized in analogy to the preparation of Example 63.

| Ex # | STRUCTURE | Intermediate | Amine | [M + H]+ | HPLC R$_t$ (min) | Method |
|---|---|---|---|---|---|---|
| 64 | 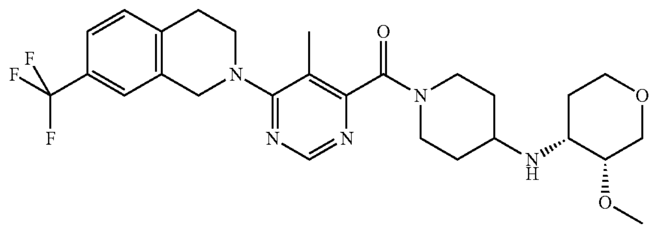 [SMILES: CO[C@H]1COCC[C@H]1NC1CCN(C(=O)c2ncnc(N3CCc4ccc(C(F)(F)F)cc4C3)c2C)CC1] | 14a | 7c | 534 | 9.21 | 1E Hydro |
| 65 | 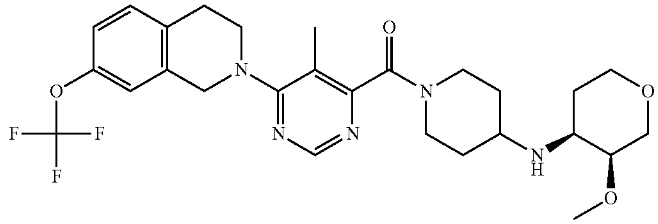 [SMILES: CO[C@@H]1COCC[C@@H]1NC1CCN(C(=O)c2ncnc(N3CCc4ccc(OC(F)(F)F)cc4C3)c2C)CC1] | 14b | 7d | 550 | 9.58 | 1E Hydro |
| 66 | 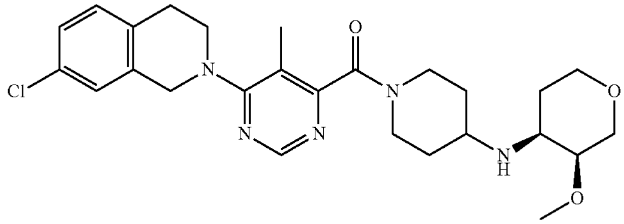 [SMILES: CO[C@@H]1COCC[C@@H]1NC1CCN(C(=O)c2ncnc(N3CCc4ccc(Cl)cc4C3)c2C)CC1] | 14c | 7d | 500 | 9.57 | 1Ef |
| 67 | 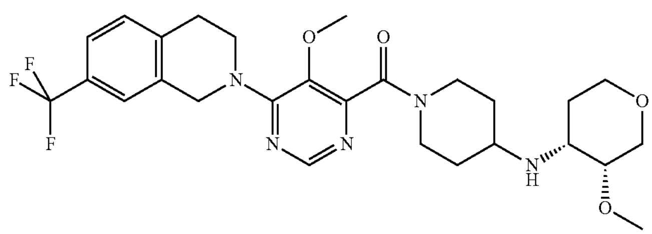 [SMILES: COc1c(C(=O)N2CCC(N[C@@H]3CCOC[C@@H]3OC)CC2)ncnc1N1CCc2ccc(C(F)(F)F)cc2C1] | 17a | 7c | 550 | 1.88 | 2Ha |
| 68 | 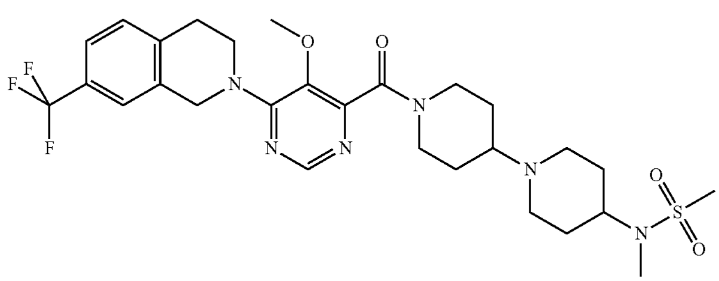 [SMILES: COc1c(C(=O)N2CCC(N3CCC(N(C)S(C)(=O)=O)CC3)CC2)ncnc1N1CCc2ccc(C(F)(F)F)cc2C1] | 17a | 7a | 611 | 1.90 | 2Ha |
| 69 | 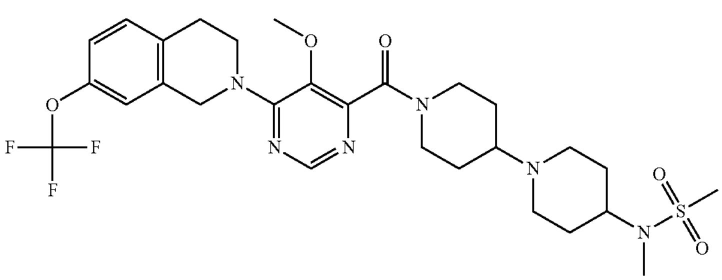 [SMILES: COc1c(C(=O)N2CCC(N3CCC(N(C)S(C)(=O)=O)CC3)CC2)ncnc1N1CCc2ccc(OC(F)(F)F)cc2C1] | 17b | 7a | 627 | 1.22 | 2Hb |

-continued

| Ex # | STRUCTURE | Intermediate | Amine | [M + H]+ | HPLC R$_t$ (min) | Method |
|---|---|---|---|---|---|---|
| 69a | 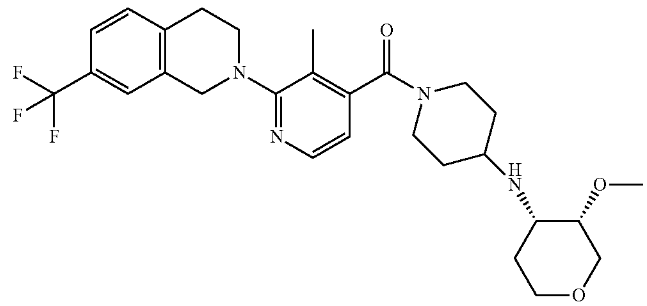 [SMILES: CO[C@@H]1COCC[C@@H]1NC1CCN(C(=O)c2ccnc(N3CCc4ccc(C(F)(F)F)cc4C3)c2C)CC1] | 14ab | 7d | 533 | 9.68 | 1E Hydro |
| 69b | 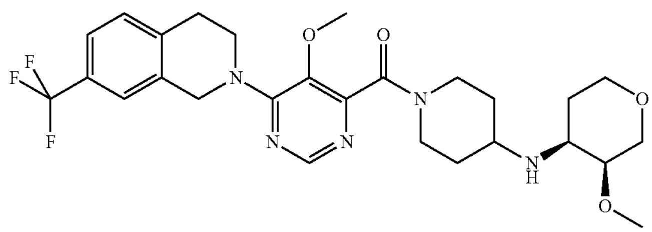 [SMILES: COc1c(C(=O)N2CCC(N[C@H]3CCOC[C@H]3OC)CC2)ncnc1N1CCc2ccc(C(F)(F)F)cc2C1] | 17a | 7d | 550 | 1.86 | 2Ha |
| 69c | 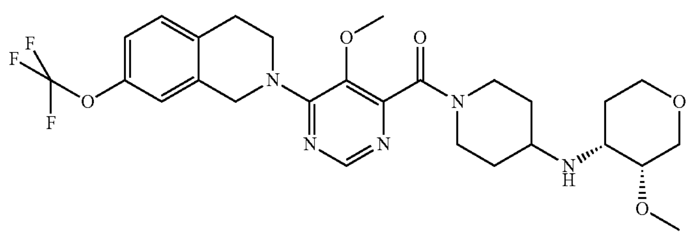 [SMILES: COc1c(C(=O)N2CCC(N[C@@H]3CCOC[C@@H]3OC)CC2)ncnc1N1CCc2ccc(OC(F)(F)F)cc2C1] | 17b | 7c | 566 | 1.9 | 2Ha |
| 69d | 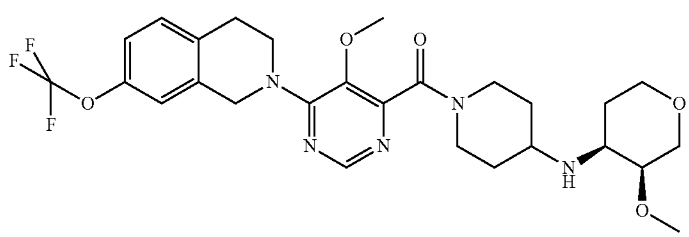 [SMILES: COc1c(C(=O)N2CCC(N[C@H]3CCOC[C@H]3OC)CC2)ncnc1N1CCc2ccc(OC(F)(F)F)cc2C1] | 17b | 7d | 566 | 1.9 | 2Ha |
| 69e | 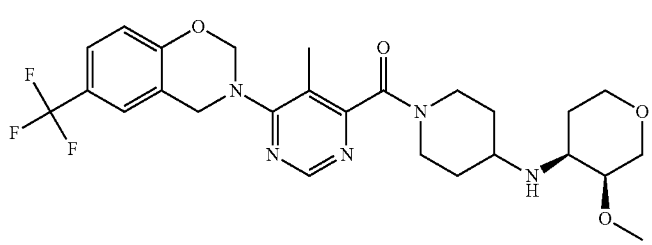 [SMILES: CO[C@@H]1COCC[C@@H]1NC1CCN(C(=O)c2ncnc(N3COc4ccc(C(F)(F)F)cc4C3)c2C)CC1] | 20 | 7d | 536 | 8.78 | 2Ha |
| 69f | 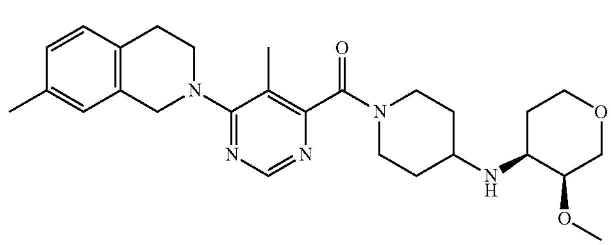 | 14aa | 7d | 480 | 8.9 | 1E Hydro |

-continued

| Ex # | STRUCTURE | Intermediate | Amine | [M + H]+ | HPLC R_t (min) | Method |
|---|---|---|---|---|---|---|
| 69g | 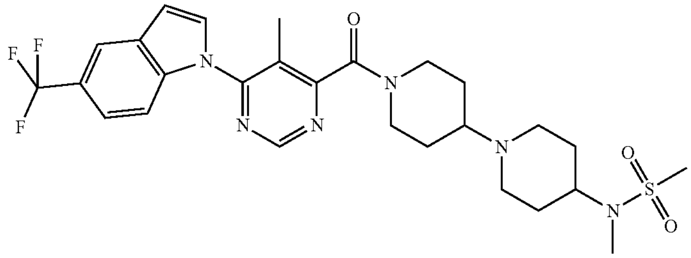 [SMILES: Cc1c(C(=O)N2CCC(N3CCC(N(C)S(C)(=O)=O)CC3)CC2)ncnc1-n1ccc2cc(C(F)(F)F)ccc21] | 14d | 7a | 579 | 1.98 | 2Ha |
| 69h | 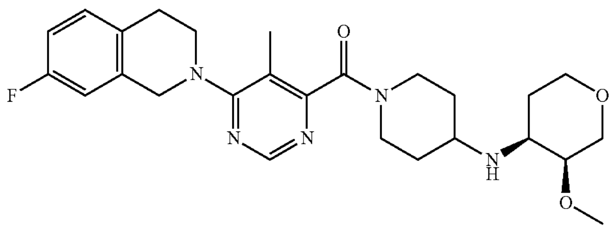 [SMILES: CO[C@@H]1COCC[C@@H]1NC1CCN(C(=O)c2ncnc(N3CCc4ccc(F)cc4C3)c2C)CC1] | 14ac | 7d | 484 | 9.02 | 1E Hydro |
| 69i | 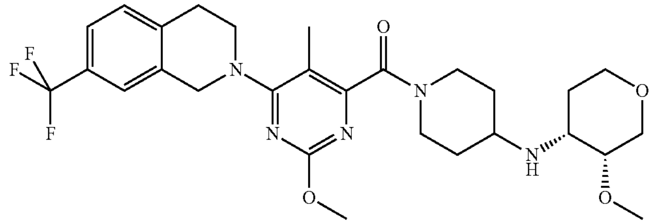 [SMILES: COc1nc(C(=O)N2CCC(N[C@@H]3CCOC[C@@H]3OC)CC2)c(C)c(N2CCc3ccc(C(F)(F)F)cc3C2)n1] | 14ad | 7c | 564 | 1.953 | 2Ha |
| 69j | 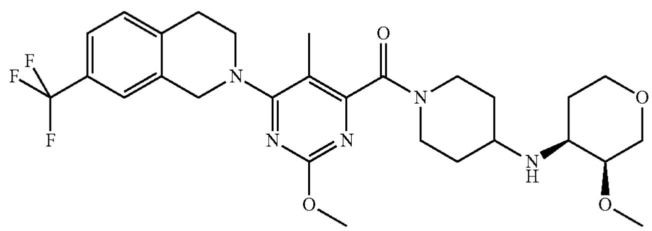 [SMILES: COc1nc(C(=O)N2CCC(N[C@H]3CCOC[C@H]3OC)CC2)c(C)c(N2CCc3ccc(C(F)(F)F)cc3C2)n1] | 14ad | 7d | 564 | 1.959 | 2Ha |
| 69k | 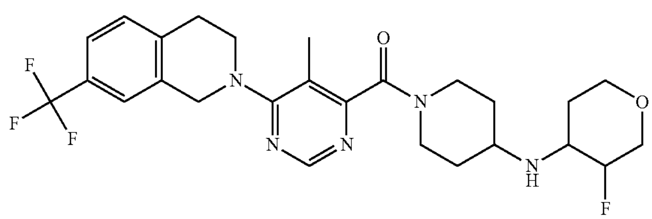 [SMILES: Cc1c(C(=O)N2CCC(NC3CCOCC3F)CC2)ncnc1N1CCc2ccc(C(F)(F)F)cc2C1] | 14a | 7e | 522 | 8.33 | 1E Hydro |
| 69l | 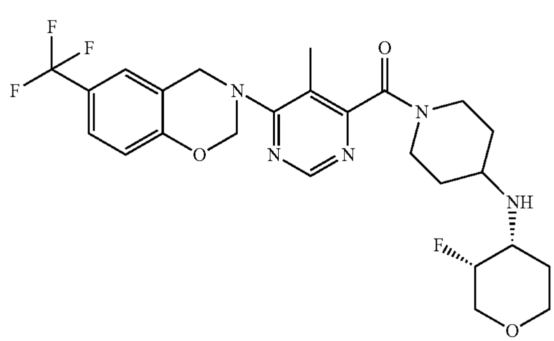 [SMILES: Cc1c(C(=O)N2CCC(N[C@@H]3CCOC[C@@H]3F)CC2)ncnc1N1COc2ccc(C(F)(F)F)cc2C1] | 20 | 7g | 524 | 8.38 | 1E Hydro |

-continued

| Ex # | STRUCTURE | Intermediate | Amine | [M + H]+ | HPLC Rt (min) | Method |
|---|---|---|---|---|---|---|
| 69m | 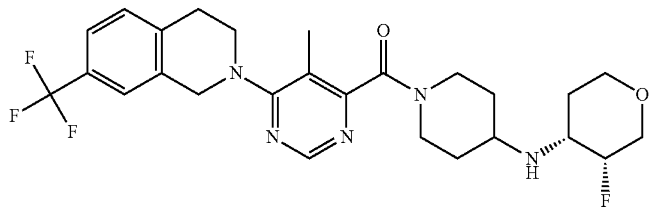 [SMILES: Cc1c(C(=O)N2CCC(N[C@@H]3CCOC[C@@H]3F)CC2)ncnc1N1CCc2ccc(C(F)(F)F)cc2C1] | 14a | 7g | 522 | 8.8 | 1E Hydro |
| 69n | 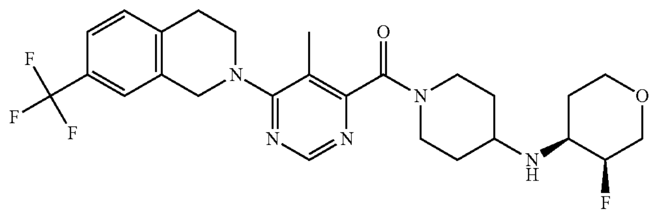 [SMILES: Cc1c(C(=O)N2CCC(N[C@H]3CCOC[C@H]3F)CC2)ncnc1N1CCc2ccc(C(F)(F)F)cc2C1] | 14a | 7f | 522 | 8.5 | 1E Hydro |
| 69o | 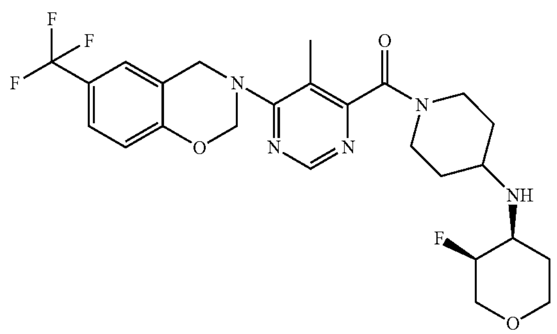 [SMILES: Cc1c(C(=O)N2CCC(N[C@H]3CCOC[C@H]3F)CC2)ncnc1N1COc2ccc(C(F)(F)F)cc2C1] | 20 | 7f | 524 | 8.16 | 1E Hydro |
| 69p | 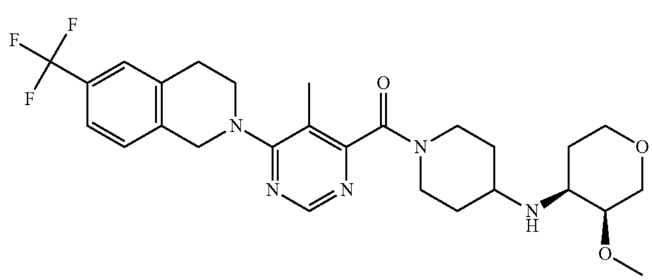 [SMILES: CO[C@@H]1COCC[C@@H]1NC1CCN(C(=O)c2ncnc(N3CCc4cc(C(F)(F)F)ccc4C3)c2C)CC1] | 14ag | 7d | 534 | 9.12 | 1E Hydro |
| 69q | 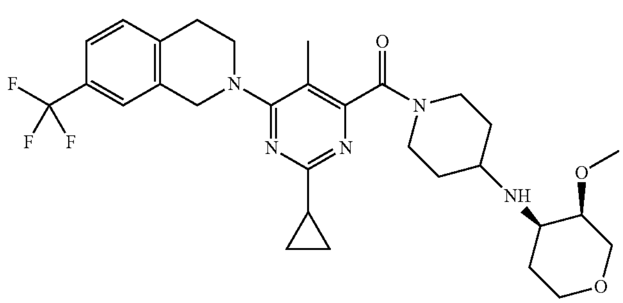 [SMILES: CO[C@H]1COCC[C@H]1NC1CCN(C(=O)c2nc(C3CC3)nc(N3CCc4ccc(C(F)(F)F)cc4C3)c2C)CC1] | 14af | 7c | 574 | 7.32 | 2FF |

-continued

| Ex # | STRUCTURE | Intermediate | Amine | [M + H]+ | HPLC R_t (min) | Method |
|---|---|---|---|---|---|---|
| 69r | 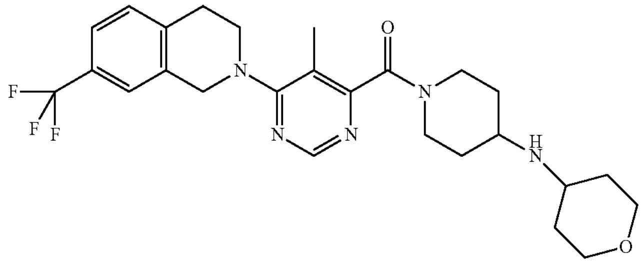 [SMILES: Cc1c(C(=O)N2CCC(NC3CCOCC3)CC2)ncnc1N1CCc2ccc(C(F)(F)F)cc2C1] | 14a | 7h | 504 | 6.96 | 2FF |
| 69s | 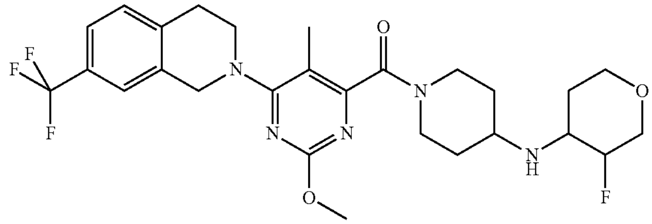 [SMILES: COc1nc(C(=O)N2CCC(NC3CCOCC3F)CC2)c(C)c(N2CCc3ccc(C(F)(F)F)cc3C2)n1] | 14ad | 7e | 552 | 1.101 | Z1_2 |
| 69t | 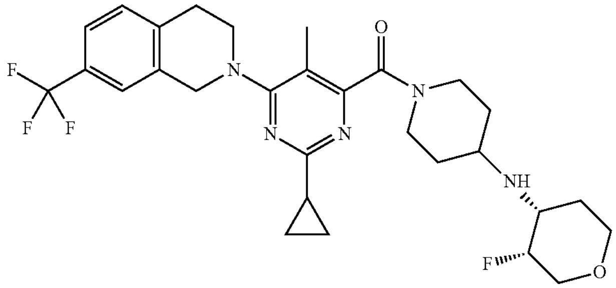 [SMILES: Cc1c(C(=O)N2CCC(N[C@@H]3CCOC[C@@H]3F)CC2)nc(C2(C)CC2)nc1N1CCc2ccc(C(F)(F)F)cc2C1] | 14af | 7g | 562 | 7.46 | 2FF |
| 69u | 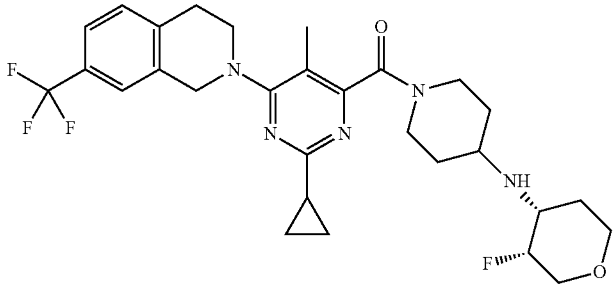 [SMILES: Cc1c(C(=O)N2CCC(N[C@@H]3CCOC[C@@H]3F)CC2)nc(C2(C)CC2)nc1N1CCc2ccc(C(F)(F)F)cc2C1] | 14af | 7g | 562 | 7.47 | 2FF |
| 69w | 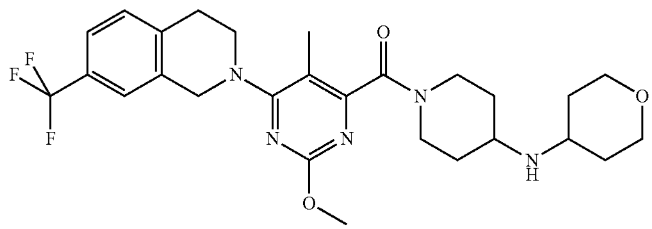 [SMILES: COc1nc(C(=O)N2CCC(NC3CCOCC3)CC2)c(C)c(N2CCc3ccc(C(F)(F)F)cc3C2)n1] | 14ad | 7h | 534 | 1.17 | Z1_5 |

-continued

| Ex # | STRUCTURE | Intermediate | Amine | [M + H]+ | HPLC R_t (min) | Method |
|---|---|---|---|---|---|---|
| 69x | 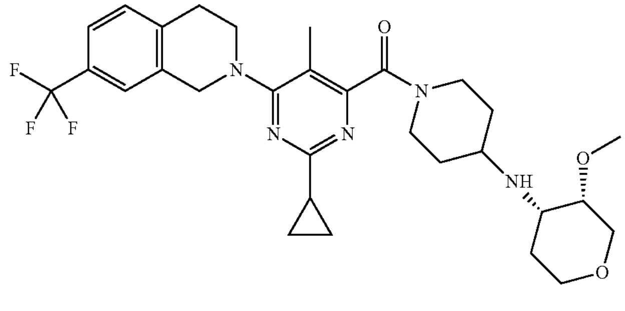 [SMILES: CO[C@@H]1COCC[C@@H]1NC1CCN(C(=O)c2nc(C3CC3)nc(N3CCc4ccc(C(F)(F)F)cc4C3)c2C)CC1] | 14af | 7d | 574 | 7.45 | 2FF |
| 69y | 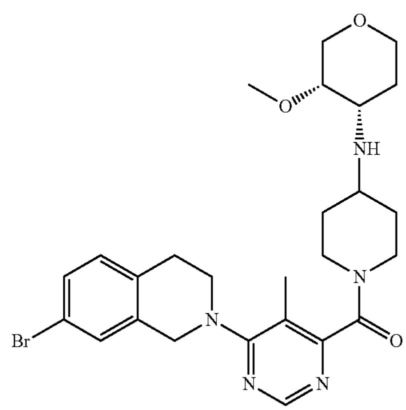 [SMILES: CO[C@@H]1COCC[C@@H]1NC1CCN(C(=O)c2ncnc(N3CCc4ccc(Br)cc4C3)c2C)CC1] | 14ae | 7d | 544 | 8.98 | 1E Hydro |
| 69z | 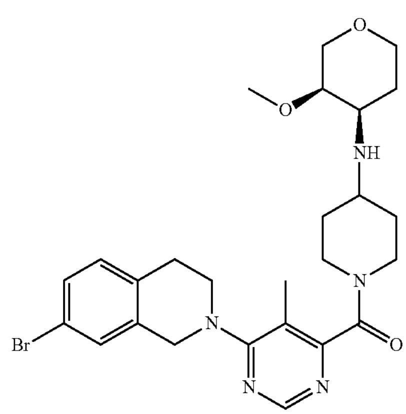 [SMILES: CO[C@H]1COCC[C@H]1NC1CCN(C(=O)c2ncnc(N3CCc4ccc(Br)cc4C3)c2C)CC1] | 14ae | 7c | 544 | 9.03 | 1E Hydro |
| 69ab | 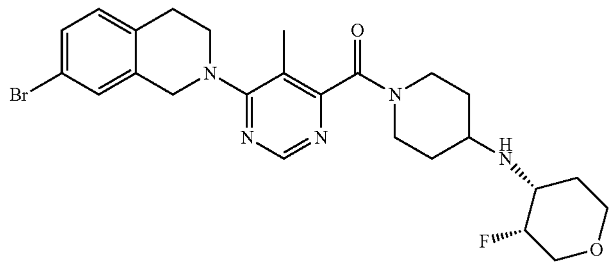 [SMILES: Cc1c(C(=O)N2CCC(N[C@@H]3CCOC[C@@H]3F)CC2)ncnc1N1CCc2ccc(Br)cc2C1] | 14ae | 7g | 532 | 8.72 | 1E Hydro |

-continued

| Ex # | STRUCTURE | Intermediate | Amine | [M + H]+ | HPLC Rt (min) | Method |
|---|---|---|---|---|---|---|
| 69ac | 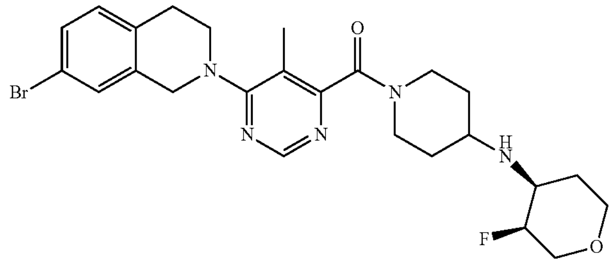 [SMILES: Cc1c(C(=O)N2CCC(N[C@H]3CCOC[C@H]3F)CC2)ncnc1N1CCc2ccc(Br)cc2C1] | 14ae | 7f | 532 | 8.72 | 1E Hydro |

Example 70

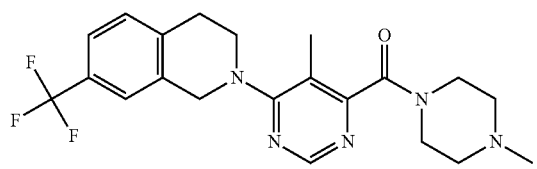 [SMILES: Cc1c(C(=O)N2CCN(C)CC2)ncnc1N1CCc2ccc(C(F)(F)F)cc2C1]

Intermediate 14a (6.8 mg, 0.020 mmol), HATU (8.6 mg, 0.020 mmol) and N,N-diisopropyl-ethylamine (0.01 ml) in 0.45 ml DMF were stirred at room temperature for 5 min. 1-methyl-piperazine (1.5 mg, 0.020 mmol) was added and the reaction mixture was stirred at room temperature for 18 h. The reaction mixture was filtered on ALOX B, washed with a solution of DMF/MeOH=90/10% and concentrated under vacuum. 4.2 mg (0.010 mmol) of the desired product were obtained.

HPLC (2G): R$_r$ (min)=3.28

[M+H]+=502

The following examples were synthesized in analogy to the preparation of Example 70

| Ex # | STRUCTURE | Intermediate | Amine | [M + H]+ | HPLC Rt (min) | Method |
|---|---|---|---|---|---|---|
| 71 | 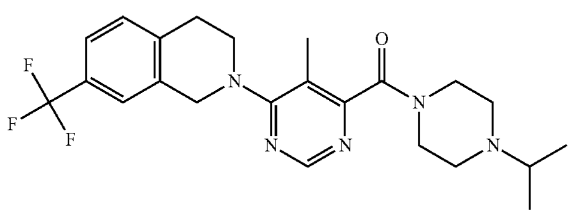 [SMILES: Cc1c(C(=O)N2CCN(C(C)C)CC2)ncnc1N1CCc2ccc(C(F)(F)F)cc2C1] | 14a | 1-isopropyl-piperazine | 447 | 3.85 | 2G |
| 72 | 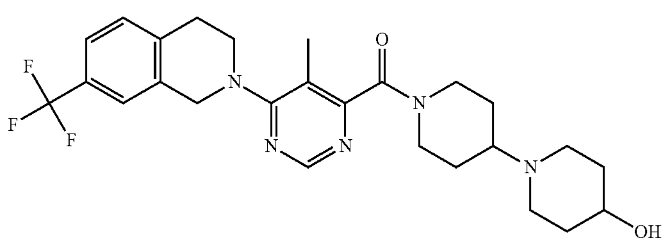 [SMILES: Cc1c(C(=O)N2CCC(N3CCC(O)CC3)CC2)ncnc1N1CCc2ccc(C(F)(F)F)cc2C1] | 14a | [1,4']-bipiperidinyl-4-ol | 503 | 3.24 | 2G |
| 73 | 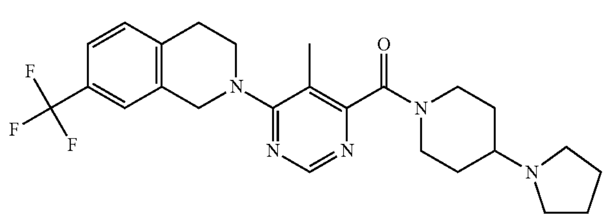 [SMILES: Cc1c(C(=O)N2CCC(N3CCCC3)CC2)ncnc1N1CCc2ccc(C(F)(F)F)cc2C1] | 14a | 4-pyrrolidin-1-yl-piperidine | 473 | 3.37 | 2G |

-continued

| Ex # | STRUCTURE | Intermediate | Amine | [M + H]+ | HPLC R$_t$ · (min) | Method |
|---|---|---|---|---|---|---|
| 74 | 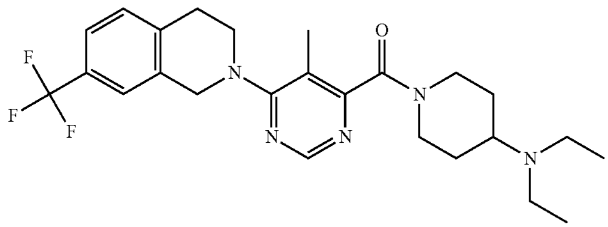 [SMILES: CCN(CC)C1CCN(C(=O)c2ncnc(N3CCc4ccc(C(F)(F)F)cc4C3)c2C)CC1] | 14a | Diethyl-piperidin-4-yl-amine | 475 | 3.39 | 2G |
| 75 | 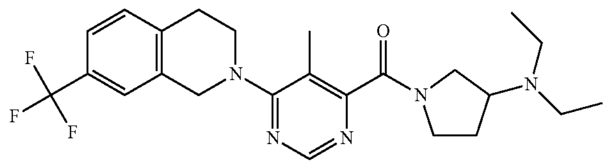 [SMILES: CCN(CC)C1CCN(C(=O)c2ncnc(N3CCc4ccc(C(F)(F)F)cc4C3)c2C)C1] | 14a | Diethyl-pyrrolidin-3-yl-amine | 461 | 3.60 | 2G |
| 76 | 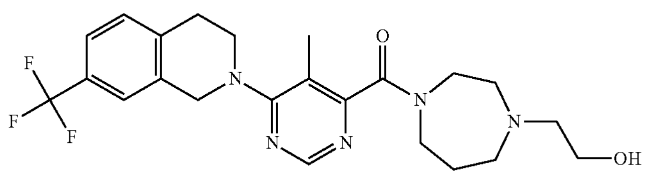 [SMILES: Cc1c(C(=O)N2CCCN(CCO)CC2)ncnc1N1CCc2ccc(C(F)(F)F)cc2C1] | 14a | 2-[1,4]diazepan-1-yl-ethanol | 463 | 3.36 | 2G |
| 77 | 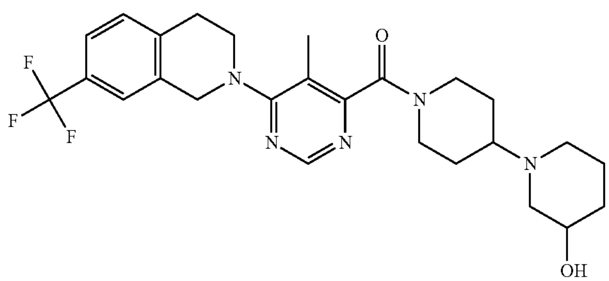 [SMILES: Cc1c(C(=O)N2CCC(N3CCCC(O)C3)CC2)ncnc1N1CCc2ccc(C(F)(F)F)cc2C1] | 14a | [1,4']-bipiperidinyl-3-ol | 503 | 3.31 | 2G |
| 78 | 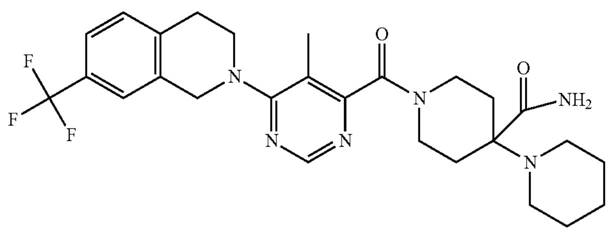 [SMILES: Cc1c(C(=O)N2CCC(C(N)=O)(N3CCCCC3)CC2)ncnc1N1CCc2ccc(C(F)(F)F)cc2C1] | 14a | [1,4']-bipiperidinyl-4'-carboxylic acid amide | 530 | 4.00 | 2G |
| 79 | 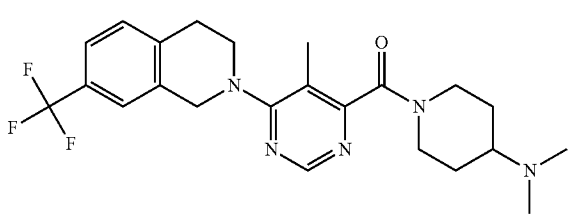 [SMILES: Cc1c(C(=O)N2CCC(N(C)C)CC2)ncnc1N1CCc2ccc(C(F)(F)F)cc2C1] | 14a | Dimethyl-piperidin-4-yl-amine | 447 | 3.28 | 2G |

| Ex # | STRUCTURE | Intermediate | Amine | [M + H]+ | HPLC $R_t$ · (min) | Method |
|---|---|---|---|---|---|---|
| 80 | 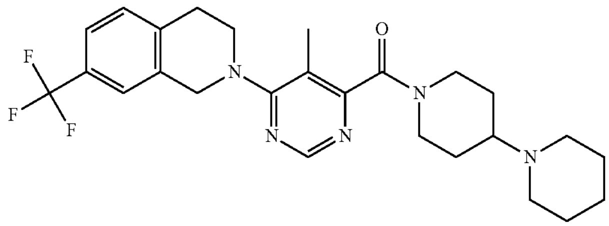 [SMILES: Cc1c(C(=O)N2CCC(N3CCCCC3)CC2)ncnc1N1CCc2ccc(C(F)(F)F)cc2C1] | 14a | [1,4']-bipiperidinyl | 487 | 3.43 | 2G |
| 81 | 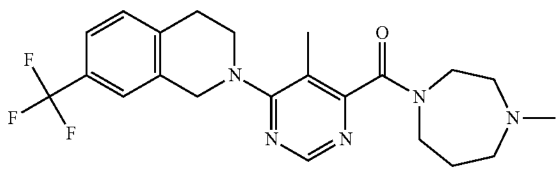 [SMILES: Cc1c(C(=O)N2CCCN(C)CC2)ncnc1N1CCc2ccc(C(F)(F)F)cc2C1] | 14a | 1-methyl-[1,4]diazepane | 433 | 3.39 | 2G |
| 82 | 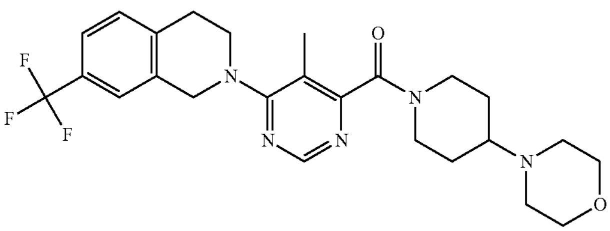 [SMILES: Cc1c(C(=O)N2CCC(N3CCOCC3)CC2)ncnc1N1CCc2ccc(C(F)(F)F)cc2C1] | 14a | 4-piperidin-4-yl-morpholine | 489 | 3.60 | 2G |

Example 83

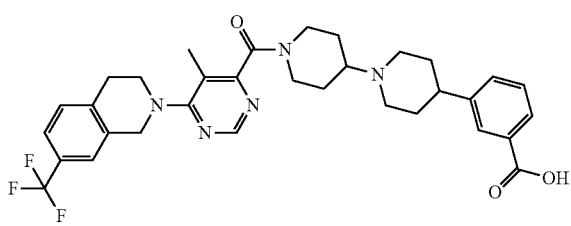 [SMILES: Cc1c(C(=O)N2CCC(N3CCC(c4cccc(C(=O)O)c4)CC3)CC2)ncnc1N1CCc2ccc(C(F)(F)F)cc2C1]

Example 84

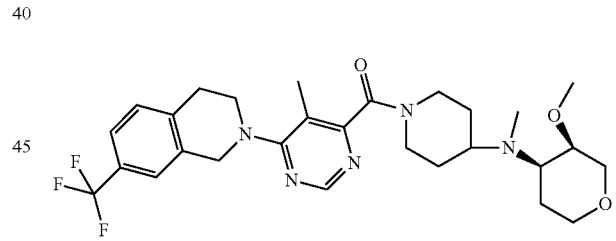

Intermediate 15 (250 mg, 0.6 mmol), commercially available 3-piperidin-4-yl-benzoic acid (144 mg, 0.6 mmol) and N,N-diisopropyl-ethyl-amine (0.30 ml, 1.79 mmol) were added to 3 ml of dry THF. Then, sodium triacetoxyborohydride (253 mg, 1.19 mmol) was added and the reaction mixture was stirred at room temperature for 72 h. The reaction mixture was concentrated under vacuum, diluted with dichloromethane and washed with an aqueous saturated sodium bicarbonate solution. The organic layer was dried over sodium sulfate and concentrated in vacuum. The crude product was purified by flash chromatography (Isolute silica gel cartridge: 10 g eluent: ethyl acetate/methanol=70/30%). 215 mg (0.35 mmol) of the desired compound were obtained.

HPLC (Method 1E f): $R_t$ (min)=8.13

[M+H]+=608

Example 64 (40 mg, 0.07 mmol), formaldehyde (0.015 ml of a 37% solution in water, 0.19 mmol), N,N-diisopropyl-ethylamine (0.019 ml, 0.011 mmol) and trifluoroacetic acid (0.009 ml, 0.12 mmol) in 3 ml methanol were stirred at room temperature for 5 min. Sodium cyanoborohydride (23 mg, 0.37 mmol) was added and the reaction mixture was stirred at room temperature overnight. The reaction mixture was concentrated under vacuum, diluted with dichloromethane and washed with an aqueous saturated sodium bicarbonate solution. The organic layer was dried over sodium sulfate and concentrated in vacuum. 32 mg (0.06 mmol) of the desired product were obtained.

HPLC (Method 1E Hydro): $R_t$ (min)=9.39; [M+H]+548

The following example was synthesized in analogy to the preparation of example 84 starting from Example 63.

| Ex # | STRUCTURE | [M + H]+ | HPLC Rt · (min) | Method |
|---|---|---|---|---|
| 85 | 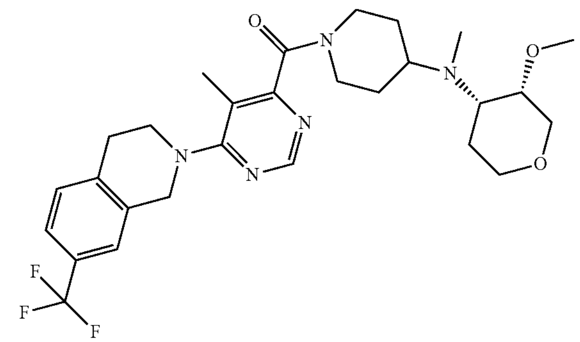 [SMILES: CO[C@@H]1COCC[C@@H]1N(C)C1CCN(C(=O)c2ncnc(N3CCc4ccc(C(F)(F)F)cc4C3)c2C)CC1] | 548 | 9.38 | 1E Hydro |

The invention claimed is:
1. A compound according to formula (I),

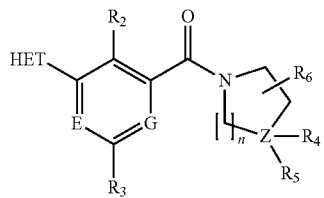

wherein HET is a group selected from among

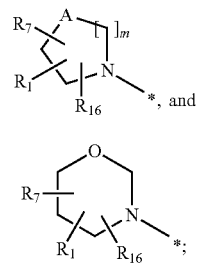

wherein the group of the structure (IIa) denotes saturated or unsaturated or partly unsaturated heterocyclyl,
wherein A is a group selected from among $CH_2$, NH, $NR_{12}$ and O,
wherein m is 1, 2 or 3,
wherein $R_{12}$ is a group selected from among $-C_5$-$C_{10}$-aryl, and $-C_5$-$C_{10}$-heteroaryl,
wherein the ring $R_{12}$ is optionally substituted with one or more groups selected from among $-CF_3$, $-O-CF_3$, $-CN$, $-C_1$-$C_6$-alkyl, $-O-C_1$-$C_4$-alkyl, and -halogen,
or wherein $R_{12}$ is optionally substituted with a bivalent group of the structure $-C_3$-$C_4$-alkylene group, which is linked on two neighbouring ring atoms of the ring $R_{12}$ such that an annellated ring is formed, in which one or two carbon centers of the -alkylene group may optionally be replaced by 1 or 2 hetero atoms selected from N, O, and S,
wherein such annelated ring is optionally substituted with one or more groups selected from among -halogen, $-CF_3$, $-O-CF_3$, $-CN$ and $-C_1$-$C_3$-alkyl, or wherein $R_{12}$ is optionally substituted with a bivalent group of the
structure $-C_3$-$C_4$-alkenylene group, which is linked on two neighbouring ring atoms of the ring $R_{12}$ such that an annellated aromatic ring is formed, in which one or two carbon centers of the -alkenylene group may optionally be replaced by 1 or 2 hetero atoms selected from N, O, and S, wherein such ring is optionally substituted with one or more groups selected from among -halogen, $-CF_3$, $-O-CF_3$, $-CN$ and $-C_1$-$C_3$-alkyl;
wherein $R_1$ is a group selected from among $-H$, -halogen, $-CN$, $-O-C_1$-$C_4$-alkyl, $-C_1$-$C_4$-alkyl, $-CH=CH_2$, $-C\equiv CH$, $-CF_3$, $-OCF_3$, $-OCF_2H$, $=O$, and $-OCFH_2$,
and wherein $R_7$ is a ring selected from among $-C_5$-$C_{10}$-aryl, and $-C_5$-$C_{10}$-hetero aryl,
and wherein the ring $R_7$ is optionally substituted with one or more groups selected from among $-CF_3$, $-O-CF_3$, $-CN$, $-C_1$-$C_6$-alkyl, $-O-C_1$-$C_6$-alkyl, and -halogen;
or wherein $R_7$ and $R_1$ on two neighbouring ring atoms together form a $-C_3$-$C_6$-alkenylene group, such that an annellated aromatic ring is formed, in which one or two or three carbon centers may optionally be replaced by 1 or 2 or 3 hetero atoms selected from N, O, and S,
wherein the resulting annelated ring being optionally substituted by one or more groups selected from among $-OH$, $-NH_2$, $-C_1$-$C_3$-alkyl, $-O-C_1$-$C_6$-alkyl, $-CN$, $-CF_3$, $-OCF_3$, halogen, $-C_6$-aryl, and $=O$;
or wherein $R_7$ and $R_1$ on two neighbouring ring atoms together form a $-C_1$-$C_6$-alkylene group such that an annellated ring is formed, in which one or two or three carbon centers may optionally be replaced by 1 or 2 or 3 hetero atoms selected from N, O, and S,
wherein the resulting annelated ring being optionally substituted by one or more groups selected from $-OH$, $-NH_2$, $-C_1$-$C_3$-alkyl, $-O-C_1$-$C_6$-alkyl, $-CN$, $-CF_3$, $-OCF_3$, -halogen, $=O$, and a group of the structure $-C_5$-$C_{10}$-aryl, wherein such $-C_5$-$C_{10}$-aryl ring is optionally substituted by one or more groups selected from among $-OH$, $-NH_2$, $-C_1$-$C_3$-alkyl, $-O-C_1$-$C_6$-alkyl, $-CN$, $-CF_3$, $-OCF_3$, halogen, and $=O$;
wherein $R_{16}$ is a group selected from among -hydrogen, and $=O$;
wherein $R_2$ is selected from among $-H$, $-O-C_1$-$C_4$-alkyl and $-C_1$-$C_4$-alkyl;

wherein $R_3$ is selected from among —H, -methyl, -ethyl, -propyl, -i-propyl, -cyclopropyl, —OCH$_3$, and —CN;
wherein n is 2;
wherein G and E are N;
wherein Z is C;
wherein $R_4$ and $R_5$ are independently selected from among an electron pair, —H, and a group of the structure —C$_1$-C$_6$-alkyl,
and wherein $R_4$ and $R_5$ if different from an electron pair or —H are optionally independently substituted with one or more groups selected from among -halogen, —OH, —CF$_3$, and —CN;
or wherein $R_4$ and $R_5$ are independently selected from among an electron pair, —H, and a group of the structure -L$_1$-R$_{13}$,
wherein $L_1$ is selected from among —NH— and —N(C$_1$-C$_4$-alkyl)-,
wherein $R_{13}$ is —C$_3$-C$_8$-heterocyclyl,
wherein $R_{13}$ is optionally substituted by one or more groups selected from among halogen, —CF$_3$, —OCF$_3$, —CN, —OH, —O—C$_1$-C$_4$-alkyl, —C$_1$-C$_6$-alkyl;
or wherein $R_4$ and $R_5$ are independently selected from among an electron pair, —H, —CONH$_2$, and a group selected from among —NR$_8$R$_9$, and —N(R$_{10}$,R$_{10'}$),
wherein $R_8$, $R_9$, are independently selected from among —H, —C$_1$-C$_6$-alkyl, and a group of the structure —C$_3$-C$_6$-cycloalkyl, wherein such ring is optionally substituted by one or more groups selected from among —F, and —OCH$_3$,
and wherein $R_{10}$ and $R_{10'}$, together form a —C$_2$-C$_6$-alkylene group such that a ring is formed, wherein such ring is optionally substituted with one or more groups selected from among —OH, —OCH$_3$, —CF$_3$, —OCF$_3$, —CN, -halogen, —C$_1$-C$_4$-alkyl, =O, and —N(C$_0$-C$_3$-alkyl)-SO$_2$—C$_1$-C$_3$-alkyl,
or wherein $R_{10}$ and $R_{10'}$ together form a —C$_2$-C$_6$-alkylene group such that a ring is formed, wherein such ring is optionally substituted by the group -C$_5$-C$_{10}$-aryl, wherein such —C$_5$-C$_{10}$-aryl ring is optionally substituted by a group of the structure —C$_0$-C$_4$-alkylene-COOH;
or wherein $R_4$ and $R_5$ are independently selected from among an electron pair, —H, and a group selected from among —N(R$_{11}$,R$_{11'}$), and wherein $R_{11}$ and $R_{11'}$ together form a —C$_2$-C$_6$-alkylene group such that a ring is formed, in which one ore two carbon centers of the —C$_2$-C$_6$-alkylene group may optionally be replaced by one or two hetero atoms selected from among N, O, and S,
wherein such ring is optionally be substituted by one or more groups on one ring atom or on two neighbouring ring atoms selected from among —OH, —NH$_2$, —C$_1$-C$_3$-alkyl, —O—C$_1$-C$_6$-alkyl, —CN, —CF$_3$, —OCF$_3$, =O, and halogen;
wherein $R_6$ is —H;
as well as in form of their acid addition salts with pharmacologically acceptable acids.

2. The compound of formula (I) according to claim 1,
wherein HET is a group according to formula (IIa),
wherein $R_1$ is —H, and wherein $R_7$ is —C$_6$-aryl,
and wherein the ring $R_7$ is optionally substituted with one or more groups selected from among —CF$_3$, —C$_1$-C$_6$-alkyl, —O—C$_1$-C$_6$-alkyl, and -halogen
and wherein $R_{16}$ is -hydrogen;
or wherein $R_7$ and $R_1$ on two neighbouring ring atoms together form a —C$_4$-alkenylene group, such that an annellated aromatic ring is formed, in which one carbon center may optionally be replaced by 1 nitrogen atom,
wherein the resulting annelated ring being optionally substituted by one or more groups selected from among —C$_1$-C$_3$-alkyl, —CN, —CF$_3$, —OCF$_3$, and -halogen,
and wherein $R_{16}$ is a group selected from -hydrogen, and =O;
or wherein $R_7$ and $R_1$ on two neighbouring ring atoms together form a —C$_1$-alkylene group such that an annellated ring is formed,
wherein the resulting annelated ring being optionally substituted by a group of the structure —C$_5$-C$_{10}$-aryl,
and wherein $R_{16}$ is -hydrogen;
wherein A is a group selected from among CH$_2$, NR$_{12}$, and O,
wherein $R_{12}$ is a group selected from among —C$_6$-aryl, and —C$_6$-heteroaryl, and
wherein the ring $R_{12}$ is optionally substituted by —CF$_3$.

3. The compound of formula (I) according to claim 1,
wherein HET is a group according to formula (IIa),
wherein $R_1$ is —H, and wherein $R_7$ is —C$_6$-aryl,
and wherein the ring $R_7$ is optionally substituted with one or more groups selected from among —CF$_3$, and —Cl,
and wherein $R_{16}$ denotes -hydrogen,
and wherein A is CH$_2$ or NR$_{12}$,
and wherein $R_{12}$ is a group of the structure —C$_6$-aryl, wherein the ring $R_{12}$ is optionally substituted by —CF$_3$;
or wherein $R_7$ and $R_1$ on two neighbouring ring atoms together form a —C$_4$-alkenylene group, such that an annellated aromatic ring is formed, in which one carbon center may optionally be replaced by 1 nitrogen atom,
wherein the resulting annelated ring being optionally substituted by one or more groups selected from —C$_1$-C$_3$-alkyl, —CN, —CF$_3$, —OCF$_3$, —Cl, —F, and, —Br,
and wherein $R_{16}$ denotes -hydrogen,
and wherein A denotes CH$_2$.

4. The compound of formula (I) according to claim 1,
wherein HET is a group according to formula (IId),
and wherein $R_7$ and $R_1$ on two neighbouring ring atoms together form a —C$_4$-alkenylene group, such that an annellated aromatic ring is formed, in which one carbon center may optionally be replaced by 1 nitrogen atom,
wherein the resulting annelated ring being optionally substituted by a group selected from —CF$_3$, and wherein $R_{16}$ denotes —H.

5. The compound of formula (I) according to claim 1,
wherein $R_4$ and $R_5$ are independently selected from among an electron pair, —H, and a group of the structure —C$_1$-C$_3$-alkyl, wherein $R_4$ and $R_5$ if different from an electron pair or —H are optionally independently substituted with one or more groups selected from —OH;
or wherein $R_4$ and $R_5$ are independently selected from among —H, and a group of the structure -L$_1$-R$_{13}$,
wherein $L_1$ is selected from among —NH—, and —N(C$_1$-C$_3$-alkyl)-,
wherein $R_{13}$ is —C$_6$-heterocyclyl comprising 1 hetero atom selected from O,
wherein $R_{13}$ is optionally substituted by one or more groups selected from among halogen, —CF$_3$, —OCF$_3$, —CN, —OH, and —O—C$_1$-C$_4$-alkyl;
or wherein $R_4$ and $R_5$ are independently selected from among —H, —CONH$_2$, and a group selected from among —NR$_8$R$_9$, and —N(R$_{10}$,R$_{10'}$),
wherein $R_8$, $R_9$, are independently selected from among —H, and —C$_1$-C$_6$-alkyl,
wherein $R_{10}$ and $R_{10'}$ together form a —C$_4$-C$_5$-alkylene group such that a ring is formed, wherein such ring is optionally substituted with one or more groups selected from among —OH, and —N(C$_0$-C$_3$-alkyl)-SO$_2$—C$_1$-C$_3$-alkyl, or wherein R$_{10}$ and R$_{10'}$ together form a —C$_4$-C$_5$-alkylene group such that a ring is formed, wherein such ring is optionally substituted by the group —C$_6$-aryl, wherein such —C$_6$-aryl ring is optionally substituted by —COOH;

or wherein R$_4$ and R$_5$ are independently selected from among —H, and a group of the structure —N(R$_{11}$,R$_{11'}$), and wherein R$_{11}$ and R$_{11'}$ together form a —C$_4$-C$_5$-alkylene group such that a ring is formed, in which one ore two carbon centers of the —C$_4$-C$_5$-alkylene group may optionally be replaced by one or two hetero atoms selected from among N, and O, wherein such ring is optionally substituted by —C$_1$-C$_3$-alkyl on one ring atom.

6. The compound of formula (I) according to claim 1, wherein R$_2$ is selected from among -methyl, and —OCH$_3$.

7. The compound of formula (I) according to claim 1, wherein R$_3$ denotes -hydrogen.

8. The compound of formula (I) according to claim 1, wherein m is 1 or 2.

9. The compound of formula (I) according to claim 1, wherein R$_4$ denotes —H, and wherein R$_5$ denotes a group of the structure —L$_1$-R$_{13}$, wherein L$_1$ is a group selected from among —NH—, and —N(CH$_3$)—, wherein R$_{13}$ is —C$_6$-heterocyclyl comprising 1 hetero atom selected from O, wherein R$_{13}$ is optionally substituted by —O—CH$_3$;

or wherein R$_4$ denotes —H and R$_5$ denotes a group of the structure —N(R$_{10}$,R$_{10'}$), wherein R$_{10}$ and R$_{10'}$ together form a —C$_4$-C$_5$-alkylene group such that a ring is formed, wherein such ring is optionally substituted with one or more groups selected from among —OH, and —N(C$_0$-C$_1$-alkyl)-SO$_2$—CH$_3$;

or wherein R$_4$ denotes —H, and wherein R$_5$ denotes a group of the structure —N(R$_{11}$,R$_{11'}$), wherein R$_{11}$ and R$_{11'}$ together form a —C$_5$-alkylene group such that a ring is formed, in which one carbon center of the —C$_5$-alkylene group is replaced by one hetero atom selected from O.

10. The compound according to claim 1 selected from the group consisting of

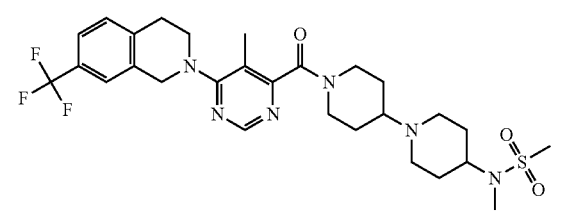

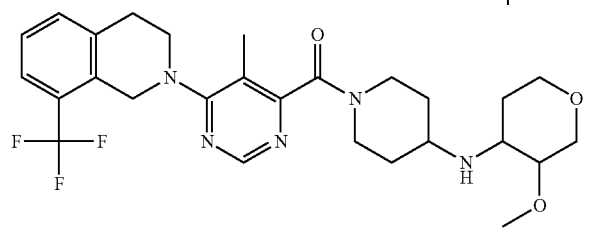

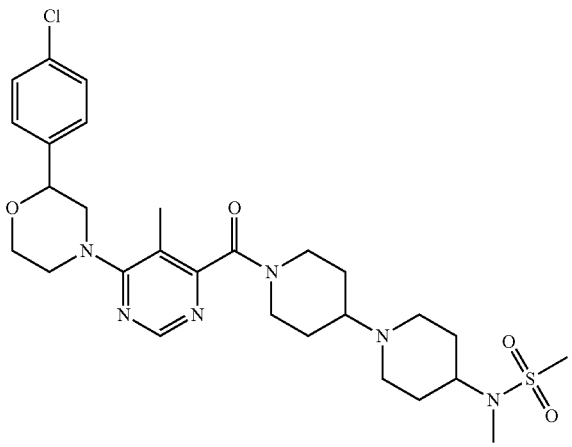

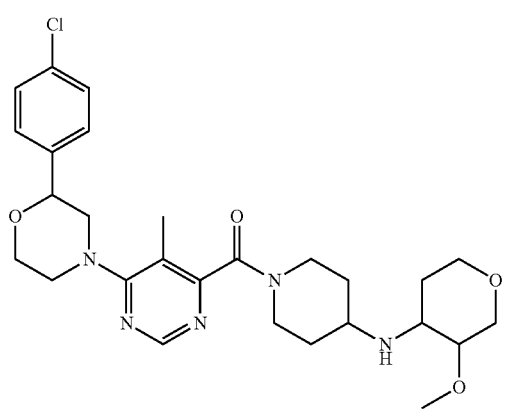

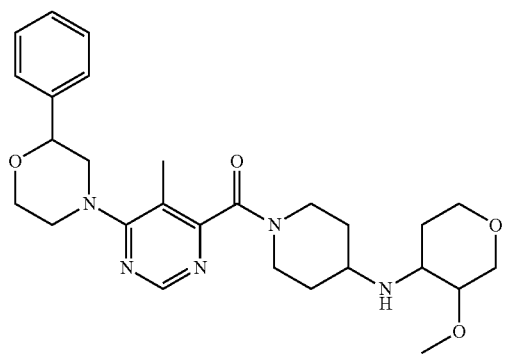

173
-continued
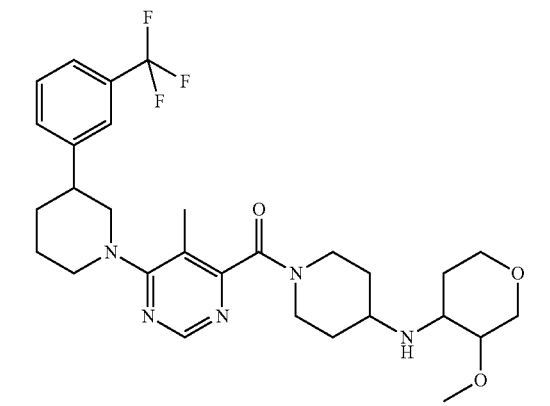
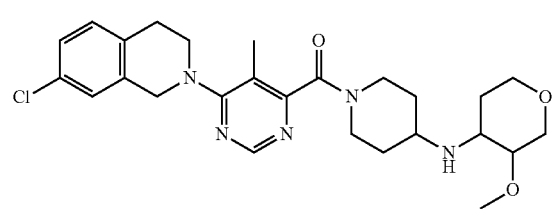
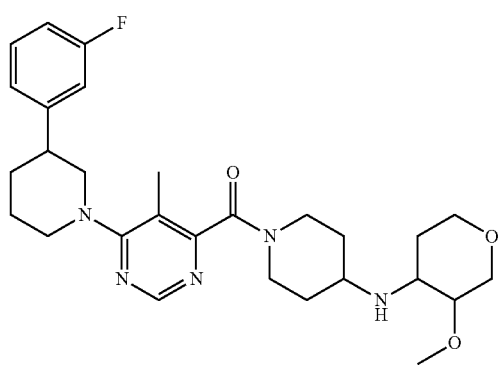
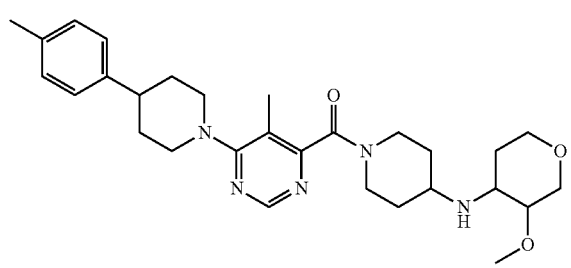
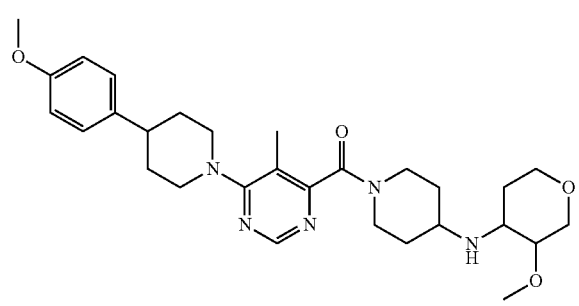
174
-continued
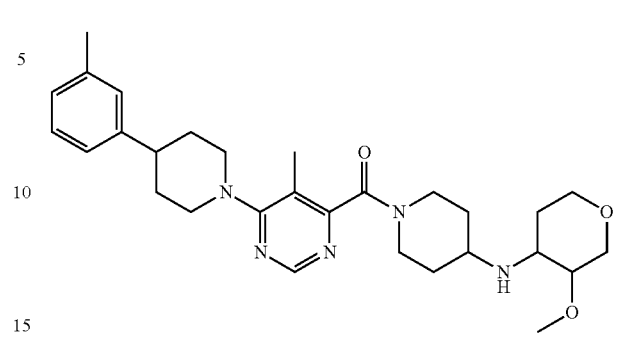
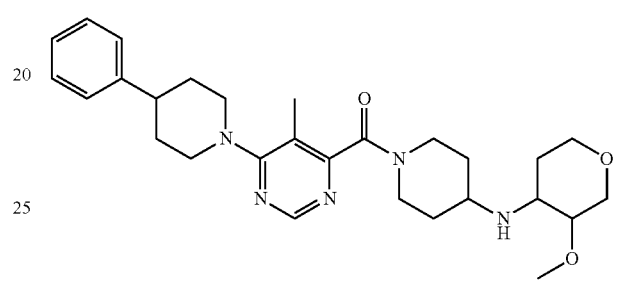
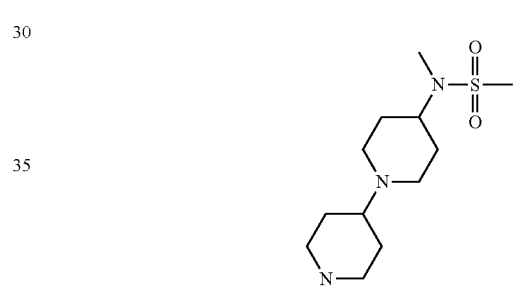
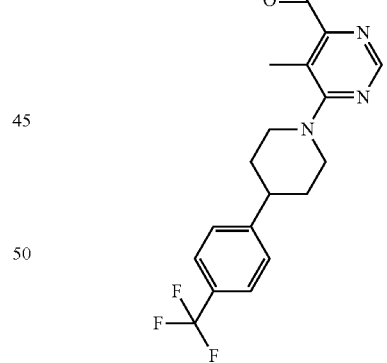
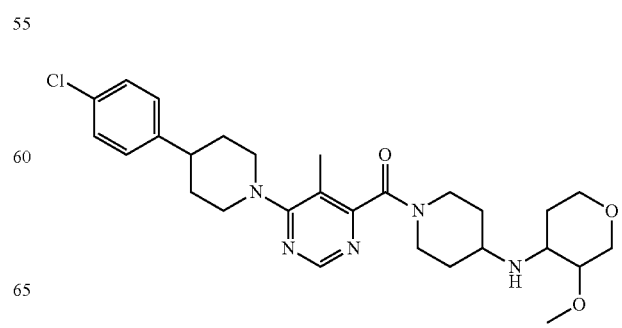

175
-continued
176
-continued
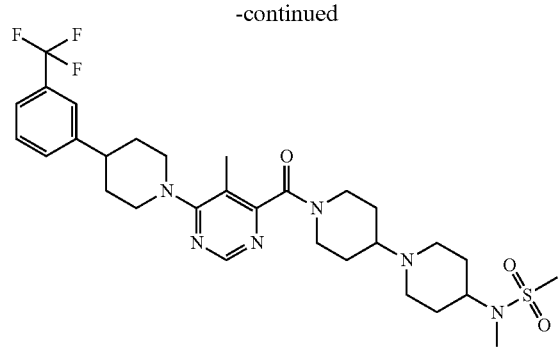
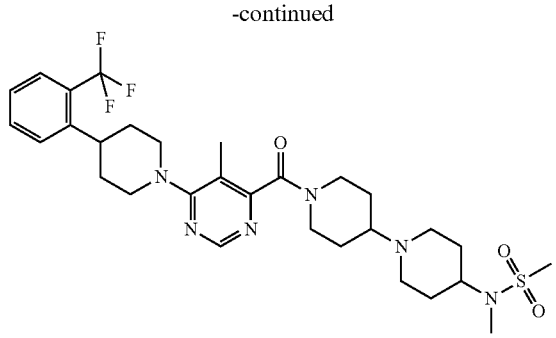

177
-continued
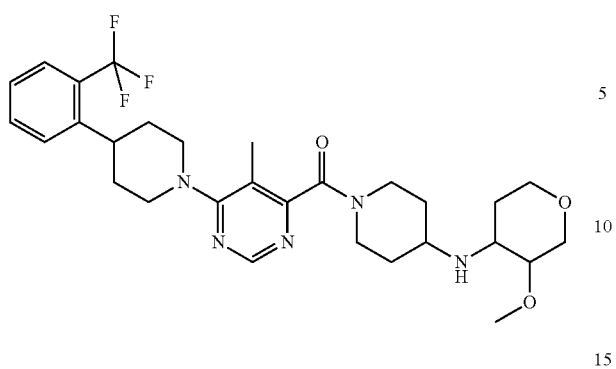
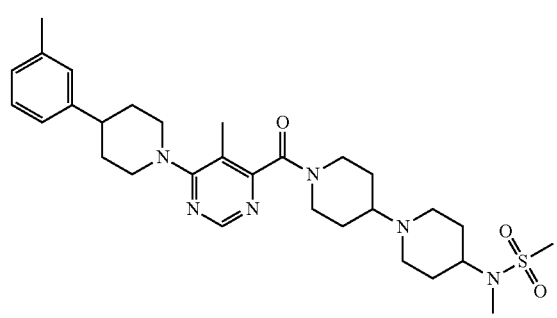
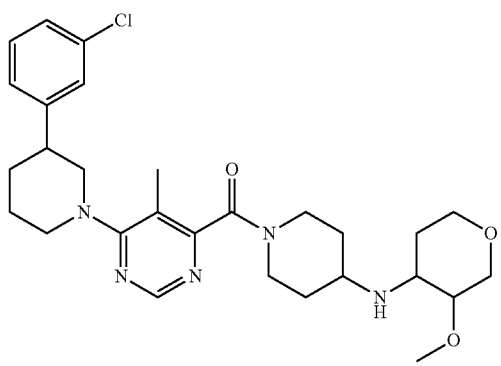
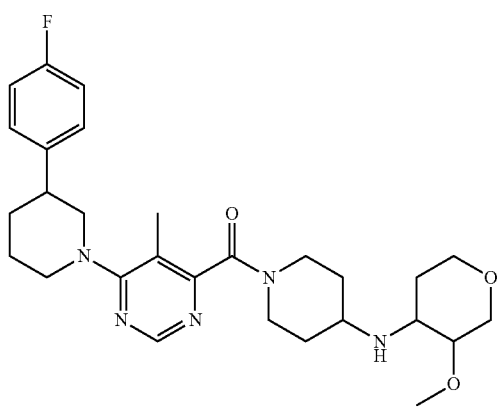
178
-continued
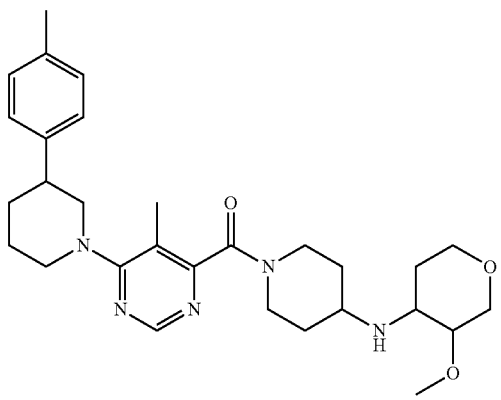
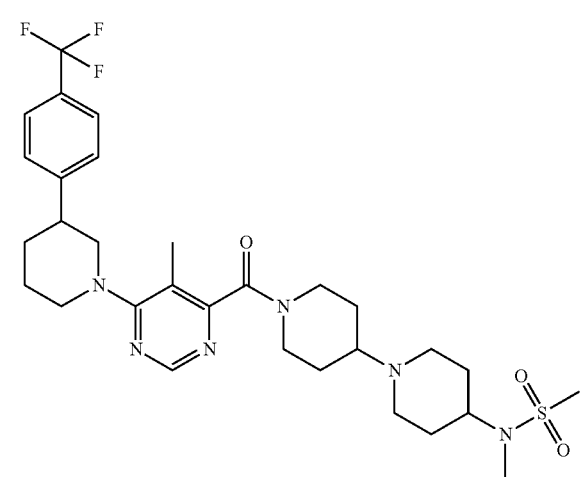
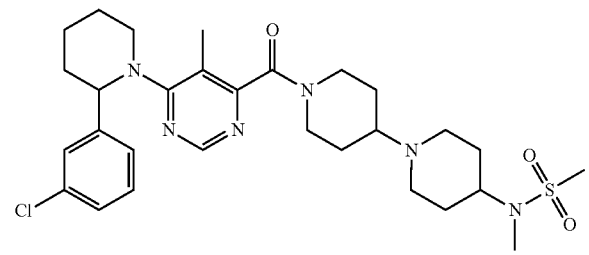
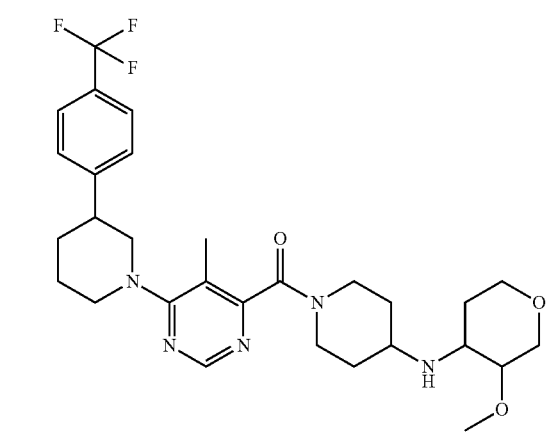

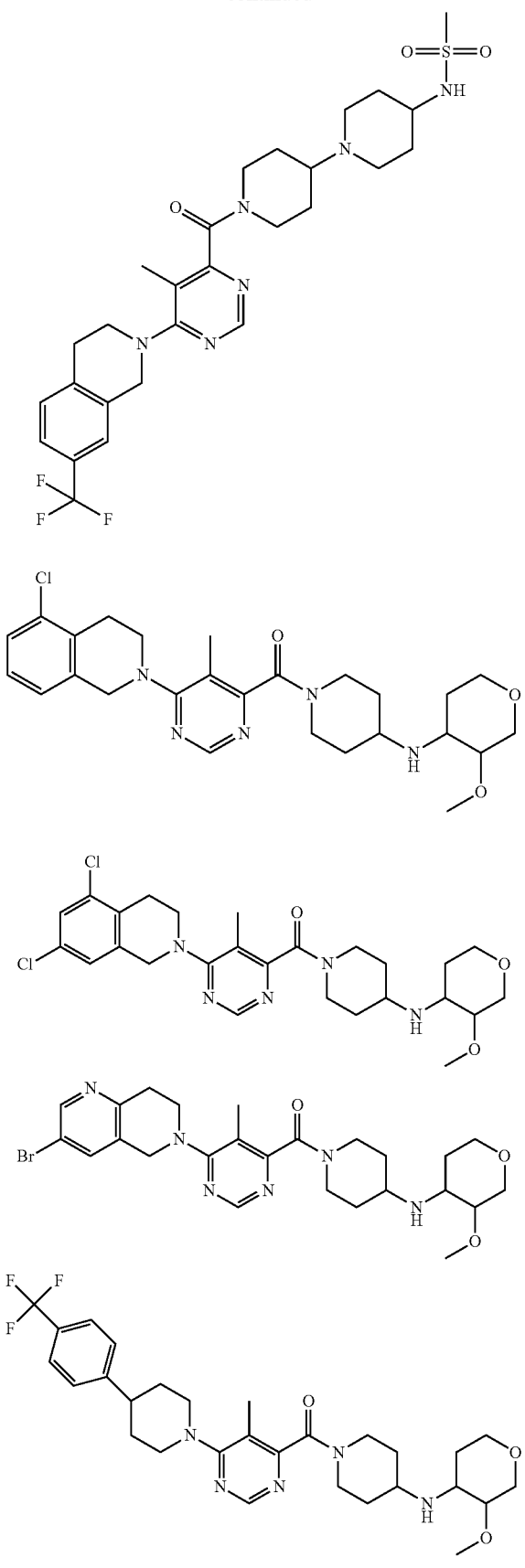
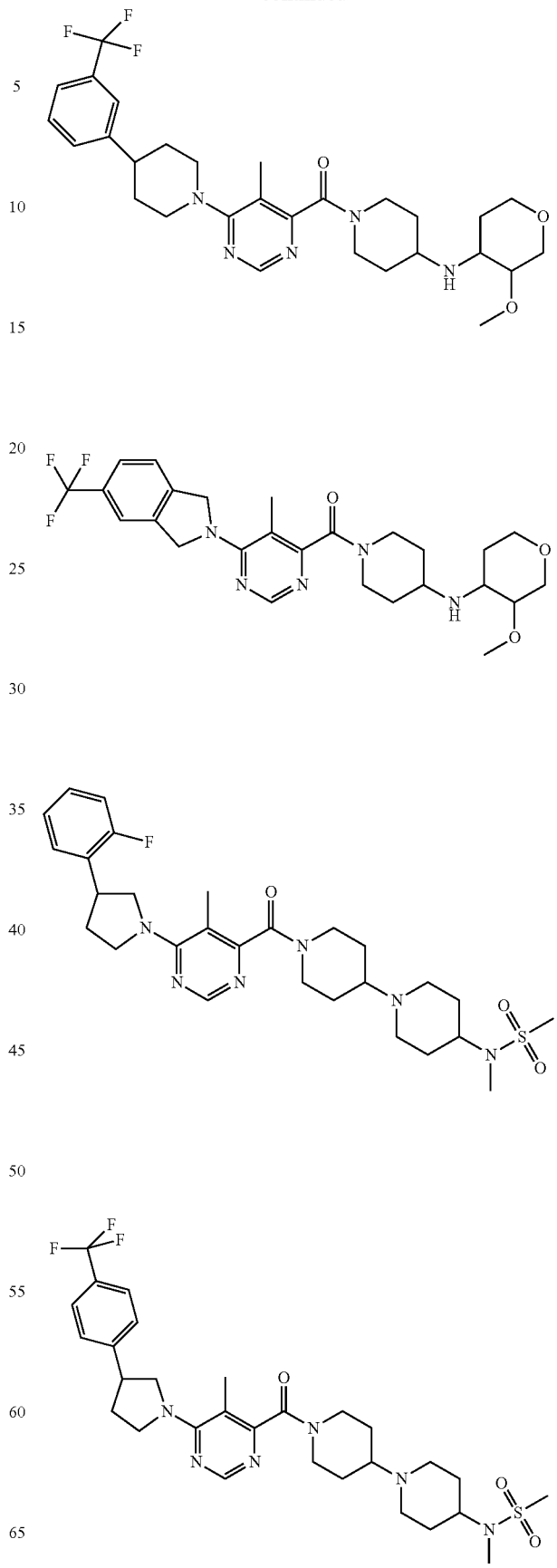

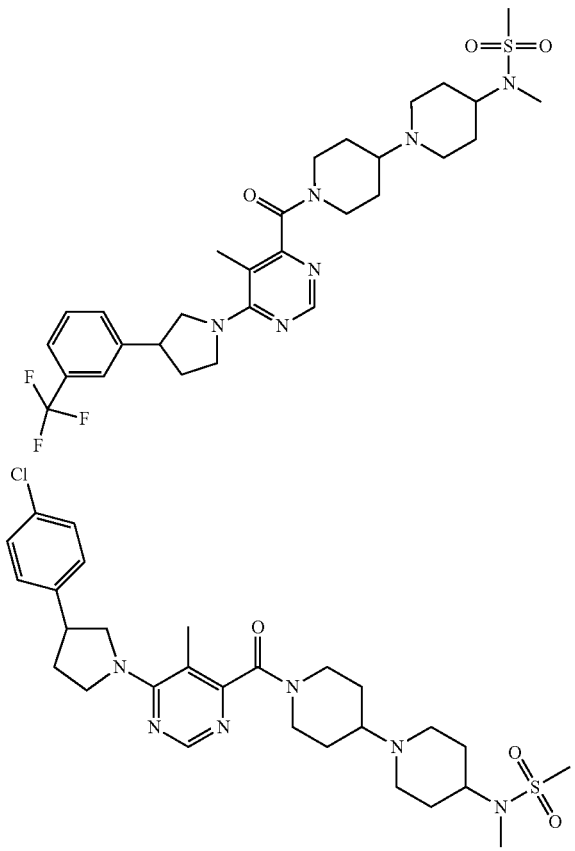
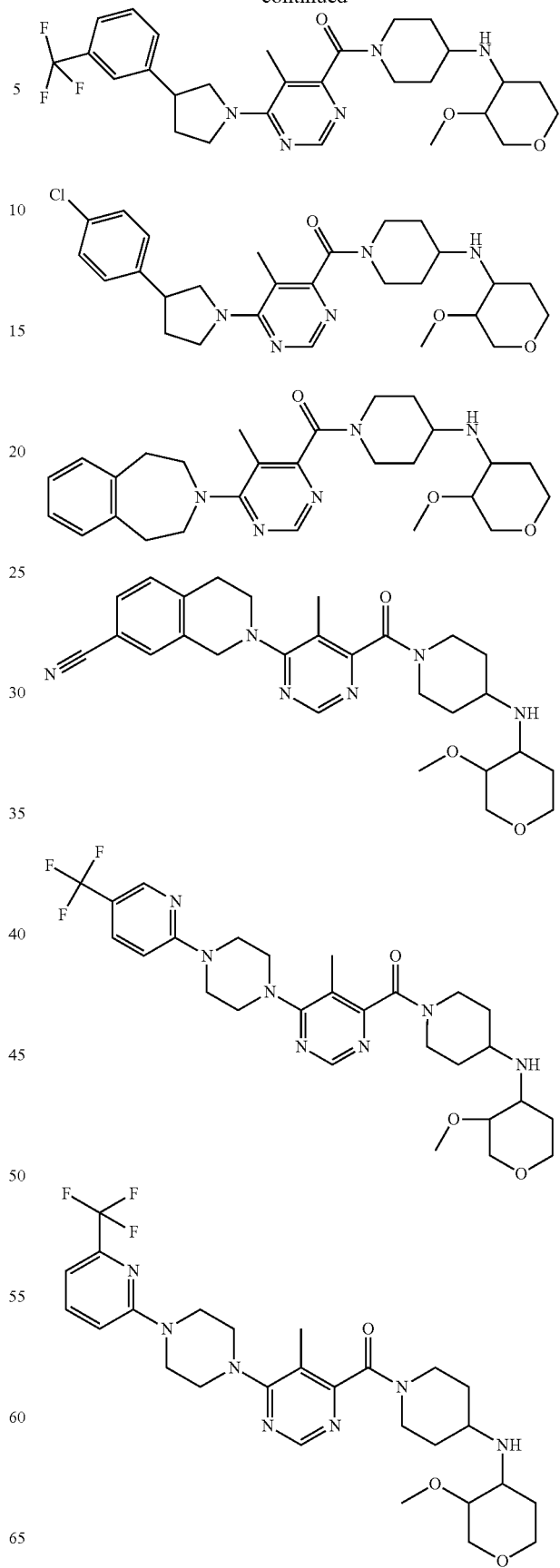

183
-continued
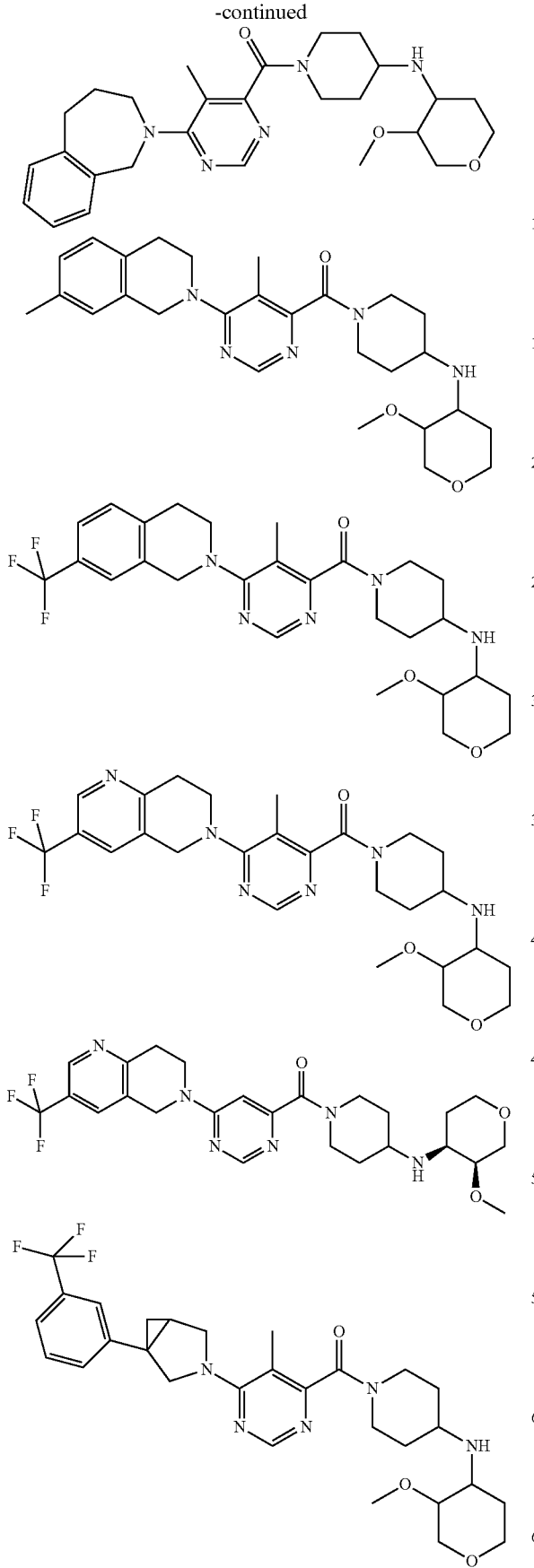
184
-continued
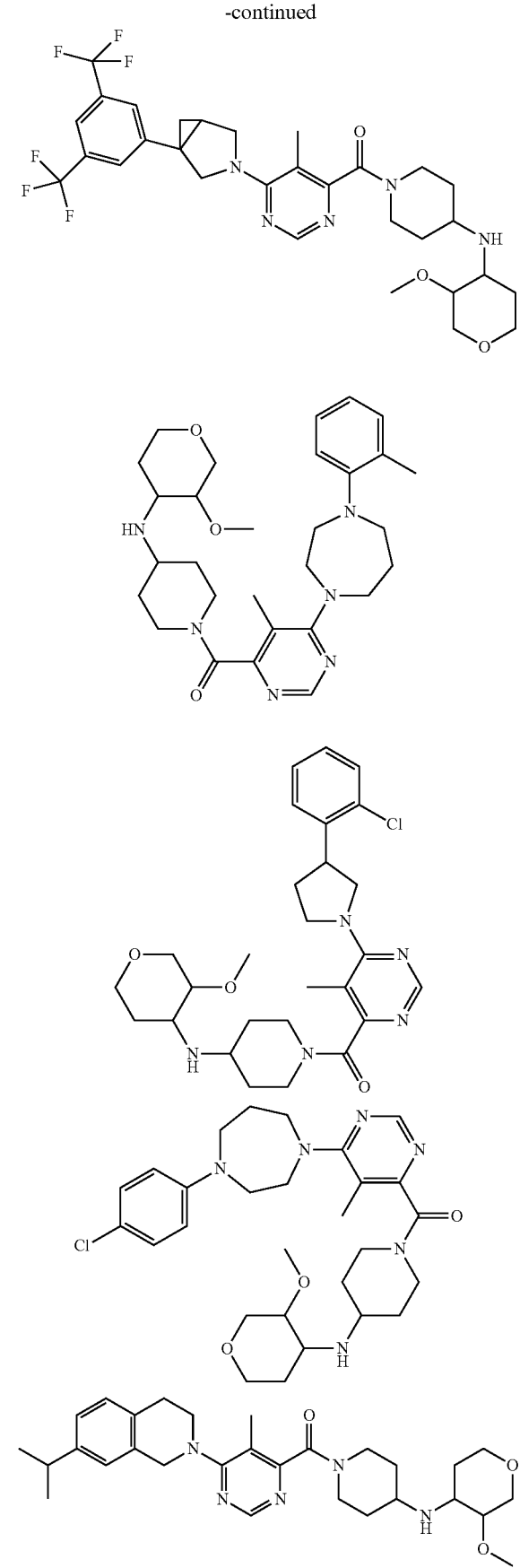

185
-continued
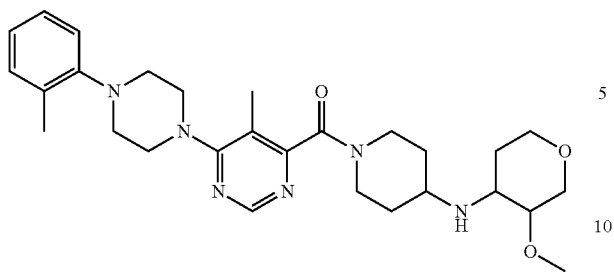
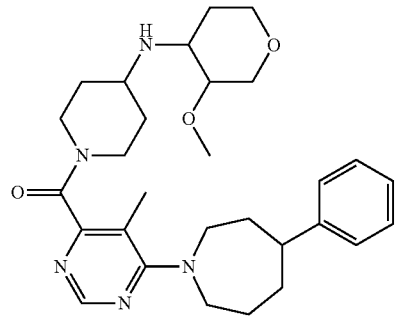
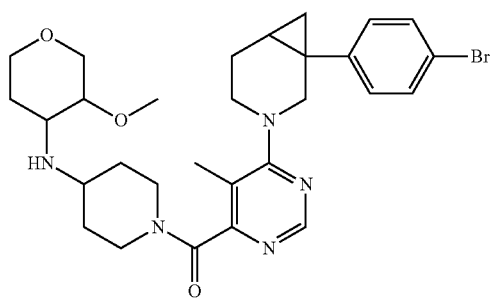
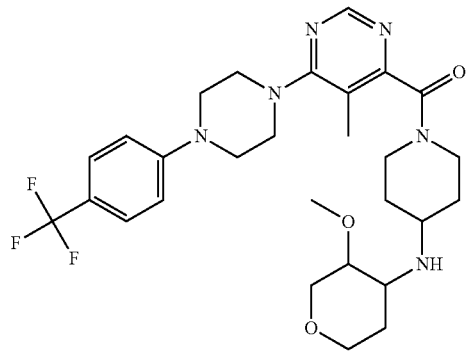
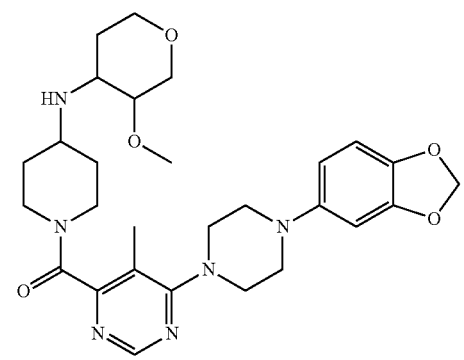
186
-continued
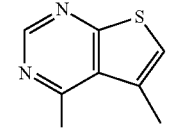
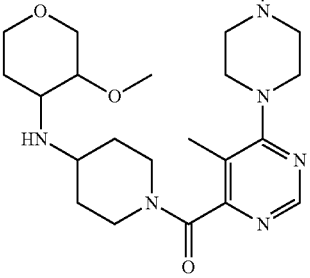
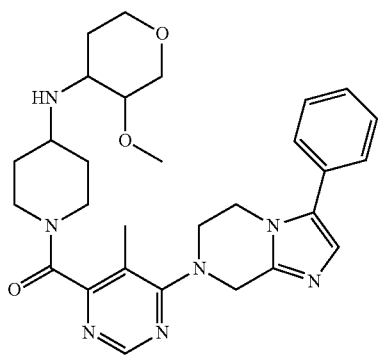
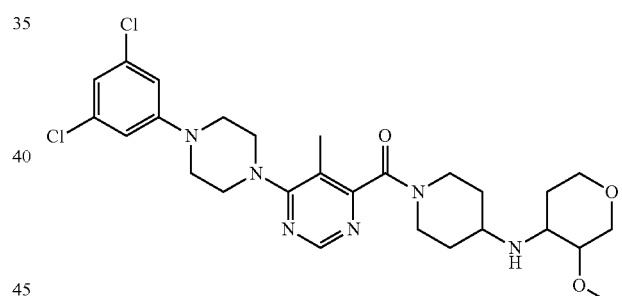
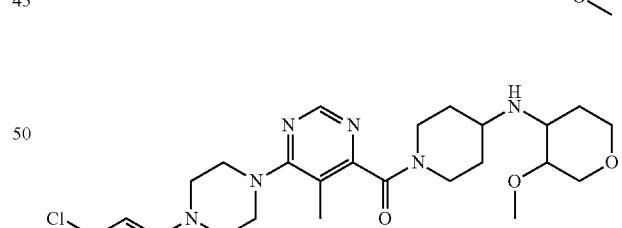
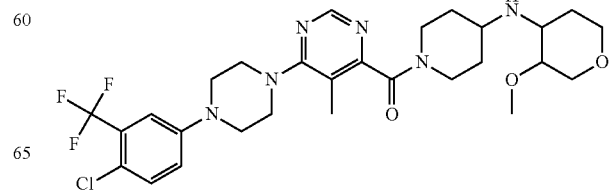

187
-continued
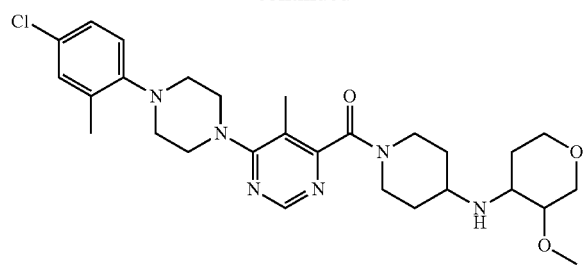
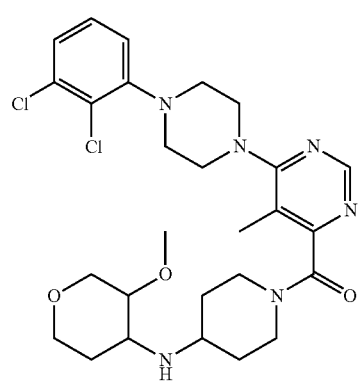
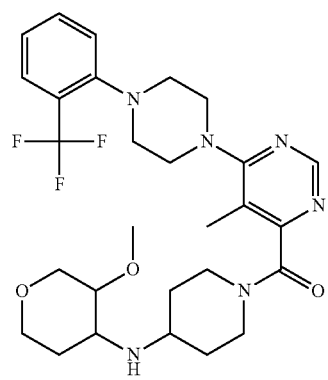
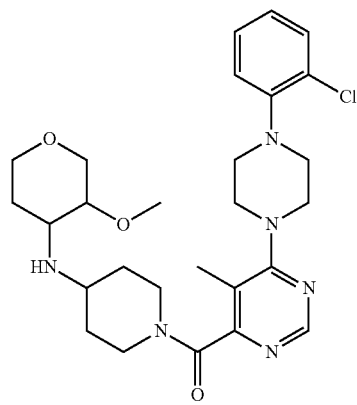
188
-continued
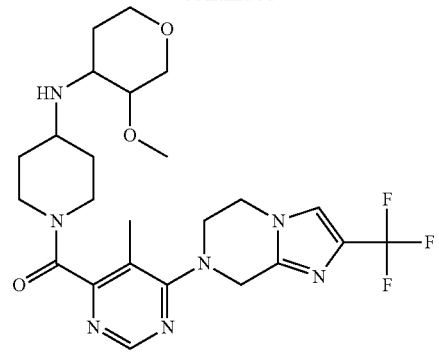
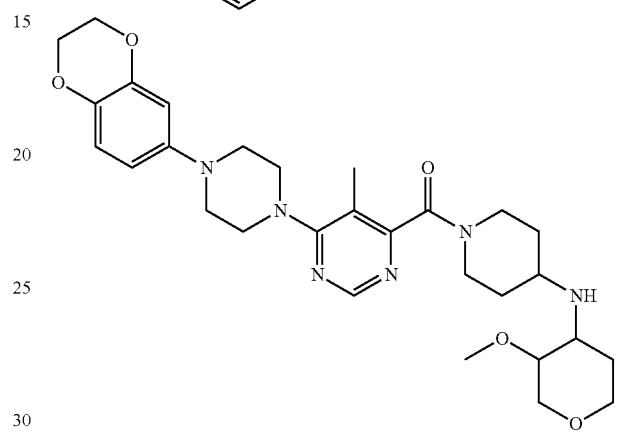
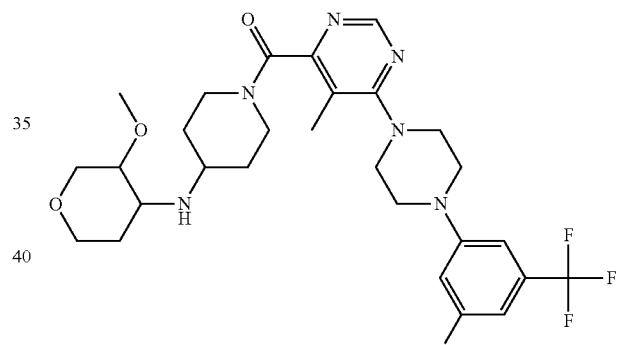
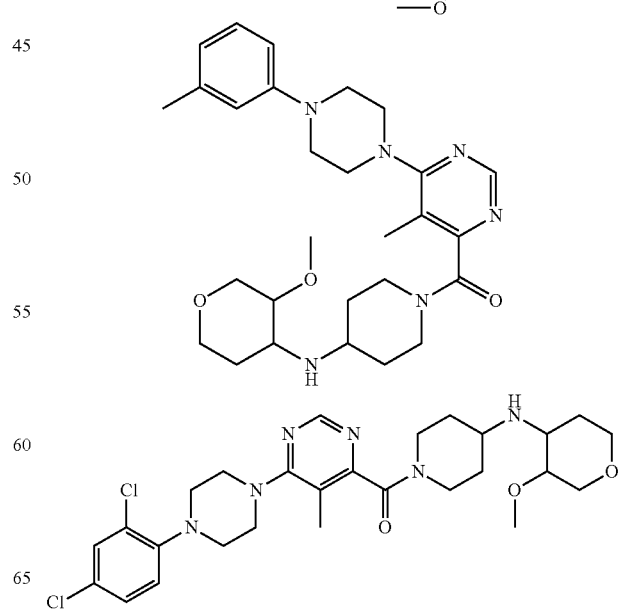

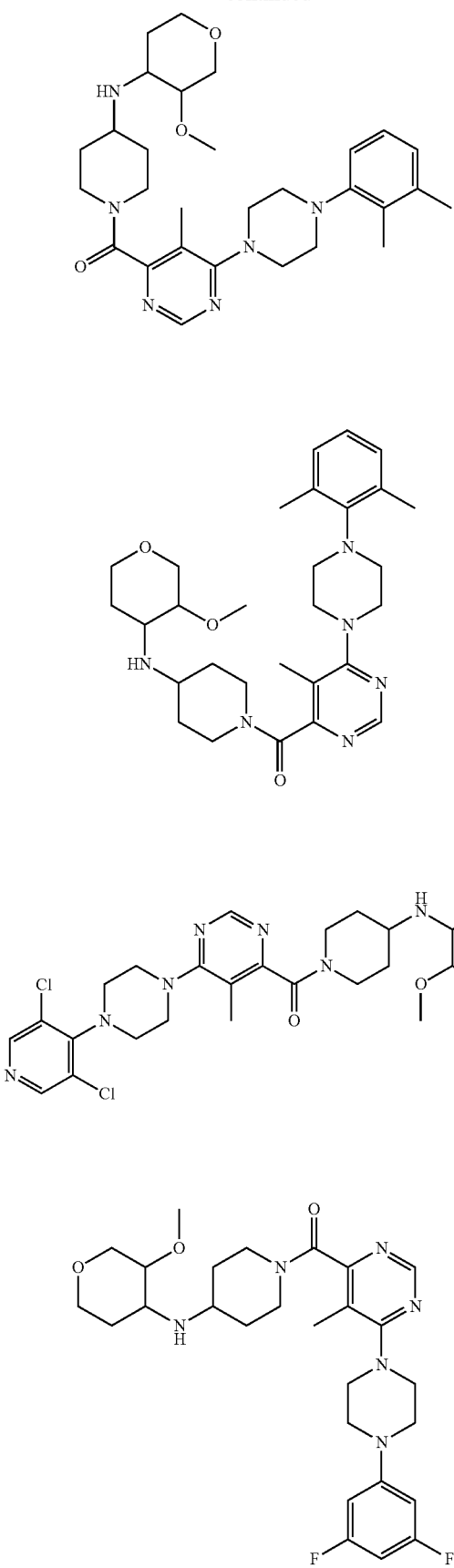

191
-continued
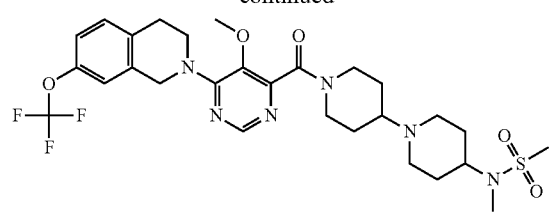
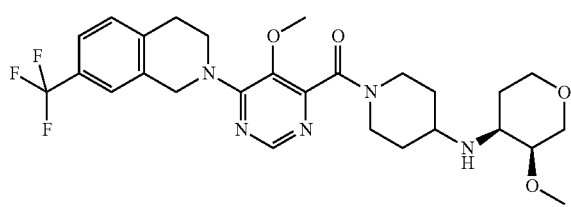
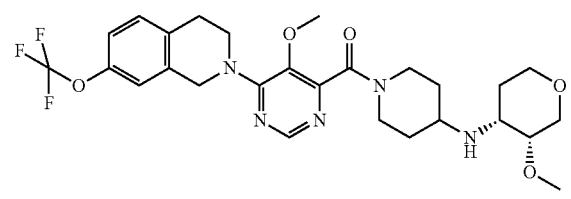
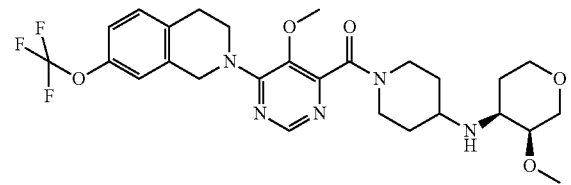
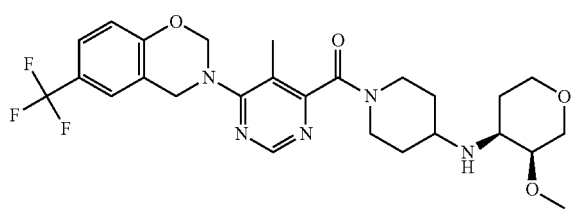
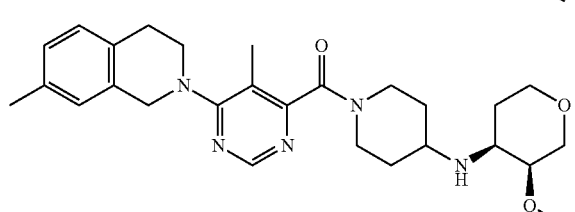
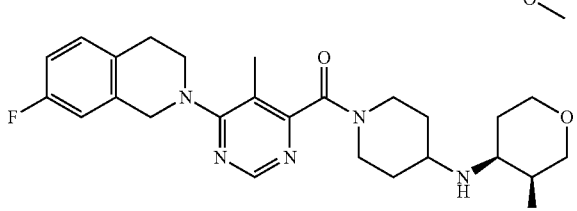
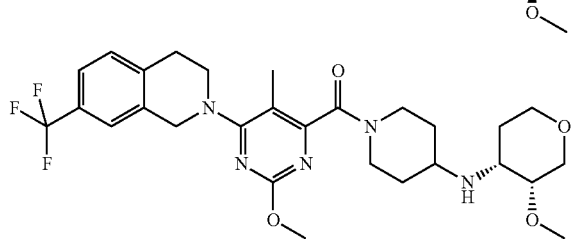
192
-continued
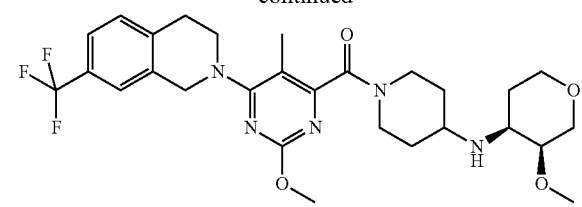
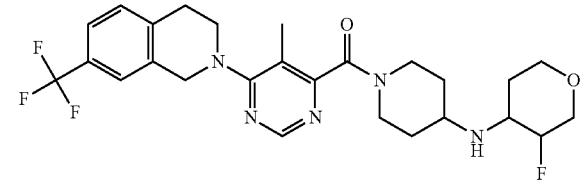
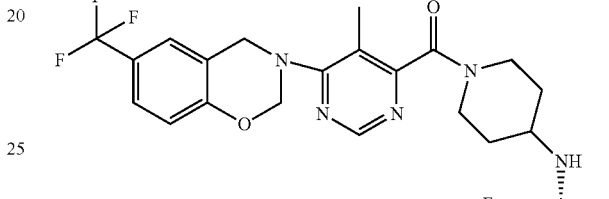
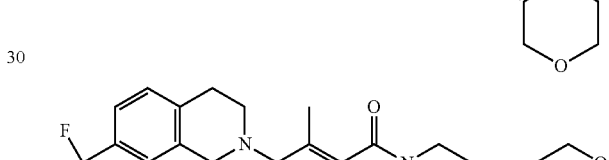
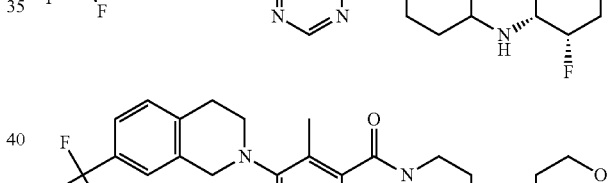
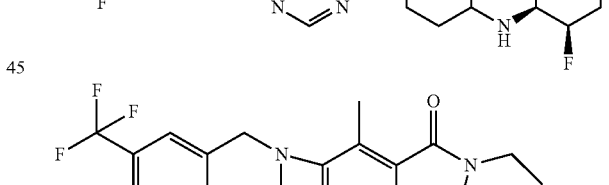
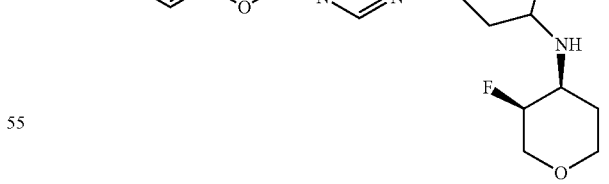
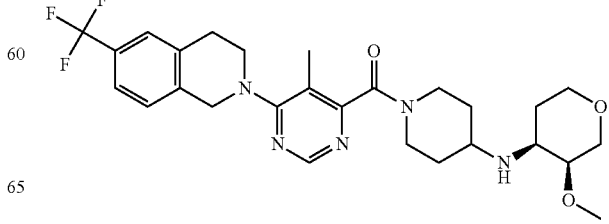

193
-continued
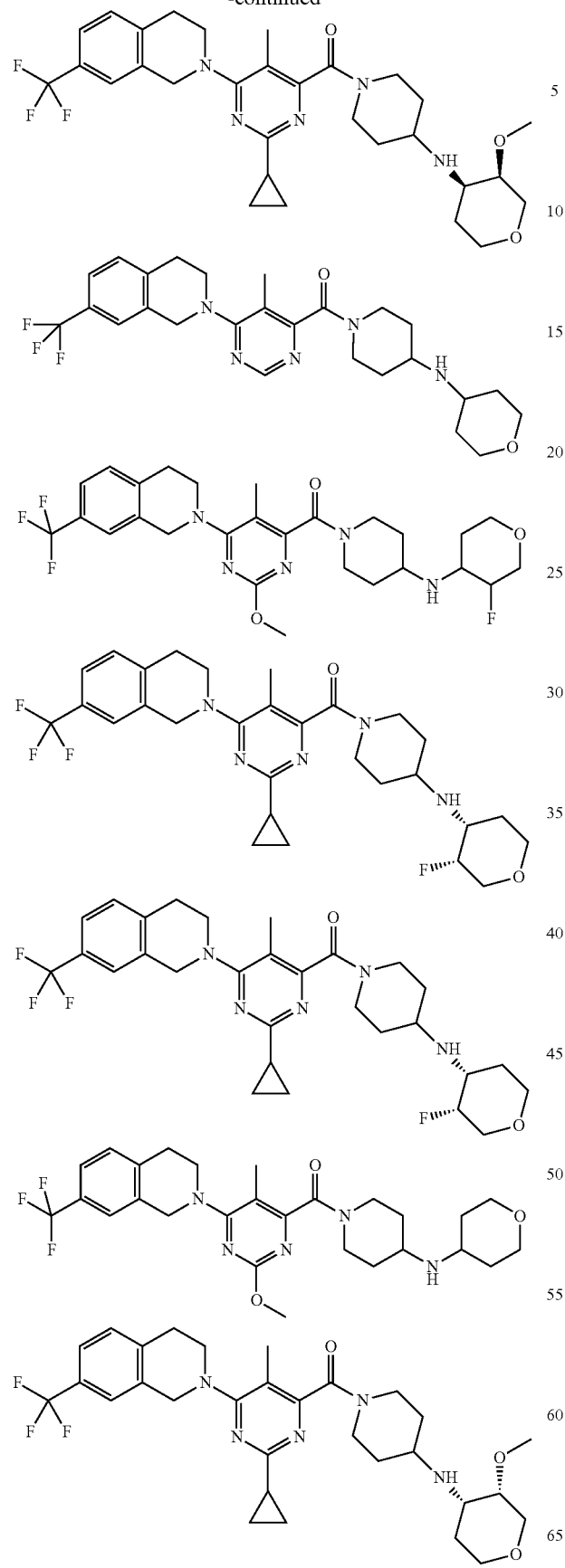
194
-continued
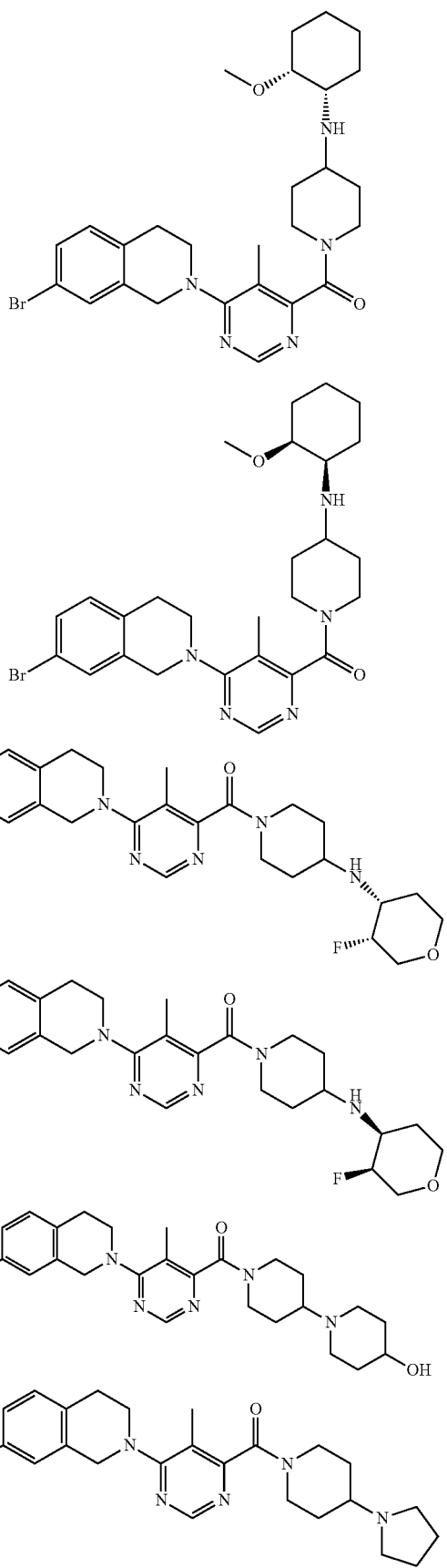

195
-continued
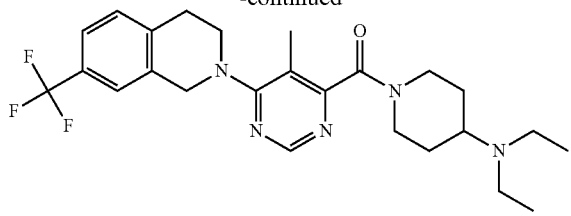
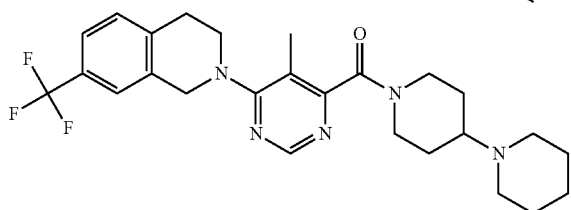
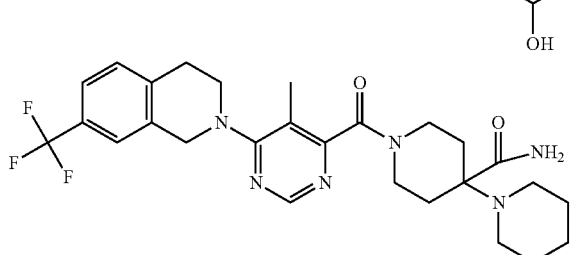
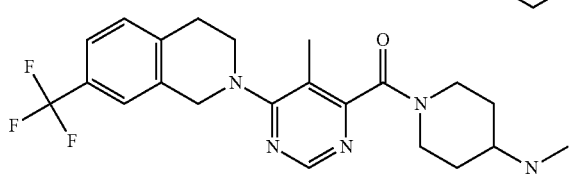
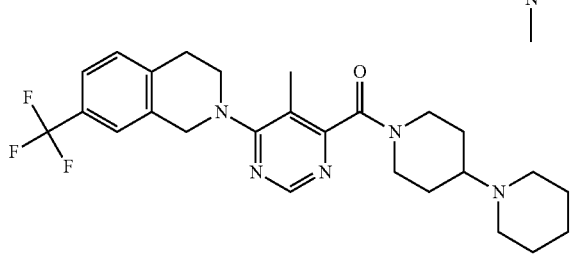
196
-continued
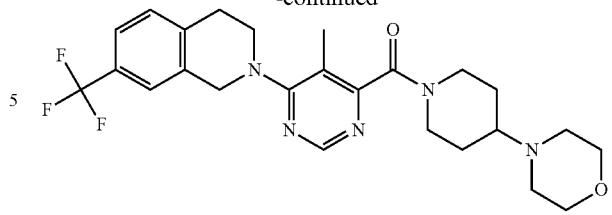
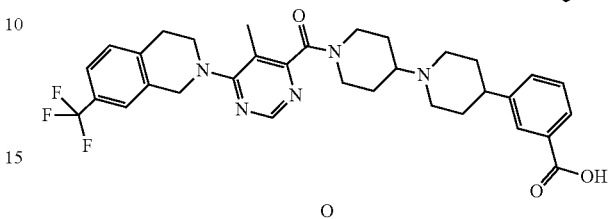
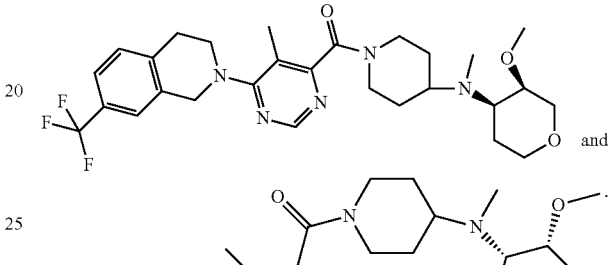
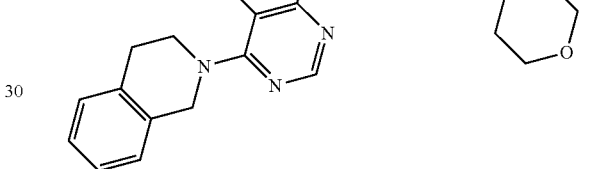
and
11. A method for the treatment of a disease selected from osteoarthritis, diabetic nephropathy, low back pain, neuropathic pain or a pain disease, comprising administering to a patient in need thereof a therapeutic amount of compound according to claim 1.
* * * * *